United States Patent
Fan et al.

(10) Patent No.: US 11,246,910 B2
(45) Date of Patent: Feb. 15, 2022

(54) METHODS OF TREATING IMMUNOLOGICAL DISORDERS USING IMMUNOSUPPRESSIVE COMPOSITIONS

(71) Applicant: Singapore Health Services Pte Ltd, Singapore (SG)

(72) Inventors: Xiubo Fan, Singapore (SG); William Ying Khee Hwang, Singapore (SG); Hsiu Ling Low, Singapore (SG); Julian Thumboo, Singapore (SG); Chin Teck Ng, Singapore (SG)

(73) Assignee: Singapore Health Services Pte Ltd, Singapore (SG)

( * ) Notice: Subject to any disclaimer, the term of this patent is extended or adjusted under 35 U.S.C. 154(b) by 0 days.

(21) Appl. No.: 16/282,461

(22) Filed: Feb. 22, 2019

(65) Prior Publication Data

US 2019/0262424 A1    Aug. 29, 2019

Related U.S. Application Data

(63) Continuation-in-part of application No. 16/326,417, filed as application No. PCT/SG2017/050408 on Aug. 18, 2017.

(30) Foreign Application Priority Data

Aug. 19, 2016  (SG) ........................... 10201606949Q

(51) Int. Cl.
*A61K 38/19* (2006.01)
*A61K 39/395* (2006.01)
*A61P 37/06* (2006.01)

(52) U.S. Cl.
CPC ........ *A61K 38/195* (2013.01); *A61K 39/3955* (2013.01); *A61P 37/06* (2018.01)

(58) Field of Classification Search
None
See application file for complete search history.

(56) References Cited

U.S. PATENT DOCUMENTS 8,541,564 B2 * 9/2013 Lillard, Jr. .............. A61P 17/00
536/23.4
2007/0071675 A1   3/2007 Wu et al.
2011/0280800 A1  11/2011 Wu et al.

FOREIGN PATENT DOCUMENTS

| JP | 2013-18756 A | 1/2013 |
|---|---|---|
| WO | WO-93/17698 A1 | 9/1993 |
| WO | WO-02/43758 A2 | 6/2002 |
| WO | WO-02/081521 A2 | 10/2002 |
| WO | WO-2006/081139 A2 | 8/2006 |
| WO | WO-2010/086854 A1 | 8/2010 |
| WO | WO-2011/072119 A2 | 6/2011 |
| WO | WO-2013/068902 A1 | 5/2013 |
| WO | WO-2015/133668 A1 | 9/2015 |

OTHER PUBLICATIONS

Shi et al., Clin. Rheumatol. (2012) vol. 31: 841-846 (Year: 2012).*
Aggarwal et al., Blood 2005, vol. 105, pp. 1815-1822. (Year: 2005).*
Search Report and Written Opinion in International Application No. PCT/SG2017/050408 dated Nov. 15, 2017, 15 pages.
Bassi et al., "Exploring the Role of Soluble Factors Associated with Immune Regulatory Properties of Mesenchymal Stem Cells", Stem Cell Rev and Rep, vol. 8, No. 2, Sep. 1, 2011, pp. 329-342.
Fan et al., "A Two Factor-cocktail: Potential Substitute for Mesenchymal Stromal Cells in Suppressing Graft Versus Host Disease", European Journal of Immunology, vol. 46, No. Supplement 1, Aug. 19, 2016, 1 page.
Supplementary European Search Report in EP Application No. 17841766 dated Mar. 3, 2020, 9 pages.
Introna et al., "Treatment of graft versus host disease with mesenchymal stromal cells: a phase I study on 40 adult and pediatric patients", Biology of Blood and Marrow Transplantation: Journal of the American Society for Blood and Marrow Transplantation 20, 2014, pp. 375-381.
Baron et al., "Cotransplantation of mesenchymal stem cells might prevent death from graft-versus-host disease (GVHD) without abrogating graft-versus-tumor effects after HLA-mismatched allogeneic transplantation following nonmyeloablative conditioning", Biology of Blood and Marrow Transplantation: Journal of the American Society for Blood and Marrow Transplantation 16, 2010, pp. 838-847.
Arima et al., "Single intra-arterial injection of mesenchymal stromal cells for treatment of steroid-refractory acute graft-versus-host disease: a pilot study", Cytotherapy 12, 2010, pp. 265-268.
Zhou et al., "Efficacy of bone marrow-derived mesenchymal stem cells in the treatment of sclerodermatous chronic graft-versus-host disease: clinical report", Biology of Blood and Marrow Transplantation: Journal of the American Society for Blood and Marrow Transplantation, 16, 2010, pp. 403-412.
Xiong et al., "Mesenchymal stem cells versus mesenchymal stem cells combined with cord blood for engraftment failure after autologous hematopoietic stem cell transplantation: a pilot prospective, open-label, randomized trial", Biology of Blood and Marrow Transplantation: Journal of the American Society for Blood and Marrow Transplantation, 20, 2014, pp. 236-242.

(Continued)

*Primary Examiner* — Gary B Nickol
*Assistant Examiner* — Jegatheesan Seharaseyon
(74) *Attorney, Agent, or Firm* — Marshall, Gerstein & Borun LLP

(57) ABSTRACT

The present disclosure describes a method of treating immunological disorders, for example alloimmune and autoimmune diseases, using a pharmaceutical composition comprising at least one mesenchymal stromal cell-derived protein Further disclosed herein is the use of the pharmaceutical composition for immunomodulation.

6 Claims, 27 Drawing Sheets

(56) References Cited

OTHER PUBLICATIONS

Sanchez-Guijo et al., "Sequential third-party mesenchymal stromal cell therapy for refractory acute graft-versus-host disease", Biology of Blood and Marrow Transplantation, 20, 2014, pp. 1580-1585.
Wang et al., "Allogeneic mesenchymal stem cell transplantation in severe and refractory systemic lupus erythematosus: 4 years of experience", Cell transplantation vol. 22, 2013, pp. 2267-2277.
Wang et al., "Umbilical cord mesenchymal stem cell transplantation in active and refractory systemic lupus erythematosus: a multicenter clinical study", Arthritis Research & Therapy, 16:R79, 2014, 14 pages.
Sun et al., "Umbilical cord mesenchymal stem cell transplantation in severe and refractory systemic lupus erythematosus", Arthritis and Rheumatism, vol. 62, No. 8, 2010, pp. 2467-2475.
Li et al., "Mesenchymal SCT ameliorates refractory cytopenia in patients with systemic lupus erythematosus", Bone Marrow Transplantation, 48, 2013, pp. 544-550.
Woodworth et al., "Safety and feasibility of umbilical cord mesenchymal stem cells in treatment-refractory systemic lupus erythematosus nephritis: time for a double-blind placebo-controlled trial to determine efficacy", Arthritis Research & Therapy, 16:113, 2014, 3 pages.
Cai et al., "Umbilical Cord Mesenchymal Stromal Cell With Autologous Bone Marrow Cell Transplantation in Established Type 1 Diabetes: A Pilot Randomized Controlled Open-Label Clinical Study to Assess Safety and Impact on Insulin Secretion", Diabetes Care, vol. 39, 2016, pp. 149-157.
Forbes et al., "A phase 2 study of allogeneic mesenchymal stromal cells for luminal Crohn's disease refractory to biologic therapy", Clinical Gastroenterology and Hepatology, 12, 2014, pp. 64-71.
Walsh et al., "Infection with a helminth parasite attenuates autoimmunity through TGF-beta-mediated suppression of Th17 and Th1 responses", The Journal of Immunology, 183, 2009, pp. 1577-1586.
Di Nicola et al., "Human bone marrow stromal cells suppress T-lymphocyte proliferation induced by cellular or nonspecific mitogenic stimuli", Blood, vol. 99, No. 10, 2002, pp. 3838-3843.
Masteller et al., "Expansion of functional endogenous antigen-specific $CD4^+CD25^+$ regulatory T cells from nonobese diabetic mice", The Journal of Immunology, 175, 2005, pp. 3053-3059.
Aggarwal et al., "Human mesenchymal stem cells modulate allogeneic immune cell responses", Blood, vol. 105, No. 4, 2005, pp. 1815-1822.
Meisel et al., "Human bone marrow stromal cells inhibit allogeneic T-cell responses by indoleamine 2,3-dioxygenase-mediated tryptophan degradation", Blood 2004, vol. 103, No. 12, pp. 4619-4621.
Su et al., "Phylogenetic distinction of iNOS and IDO function in mesenchymal stem cell-mediated immunosuppression in mammalian species", Cell Death and Differentiation, 21, 2014, pp. 388-396.
Meisel et al., "Human but not murine multipotent mesenchymal stromal cells exhibit broad-spectrum antimicrobial effector function mediated by indoleamine 2,3-dioxygenase", Leukemia, 25, 2011, pp. 648-654.
Jui et al., "Autologous mesenchymal stem cells prevent transplant arteriosclerosis by enhancing local expression of interleukin-10, interferon-gamma, and indoleamine 2,3-dioxygenase", Cell Transplantation, vol. 21, 2012, pp. 971-984.
Ge et al., "Regulatory T-cell generation and kidney allograft tolerance induced by mesenchymal stem cells associated with indoleamine 2,3-dioxygenase expression", Transplantation, vol. 90, No. 12, 2010, pp. 1312-1320.
Nemeth et al., "Bone marrow stromal cells attenuate sepsis via prostaglandin $E_2$-dependent reprogramming of host macrophages to increase their interleukin-10 production", Nature Medicine, 15(1), 2009, pp. 42-49.
Ren et al., "Mesenchymal stem cell-mediated immunosuppression occurs via concerted action of chemokines and nitric oxide", Cell Stem Cell, 2, 2008, pp. 141-150.
Oh et al., "Intravenous mesenchymal stem cells prevented rejection of allogeneic corneal transplants by aborting the early inflammatory response", Molecular Therapy: The Journal of the American Society of Gene Therapy, vol. 20, No. 11, 2012, pp. 2143-2152.
Mougiakakos et al., "The impact of inflammatory licensing on heme oxygenase-1-mediated induction of regulatory T cells by human mesenchymal stem cells", Blood, vol. 117, No. 18, 2011, pp. 4826-4835.
Liang et al., "Mesenchymal stromal cells expressing heme oxygenase-1 reverse pulmonary hypertension", Stem Cells 29(1), 2011, pp. 99-107.
Hou et al., "The effect of heme oxygenase-1 complexed with collagen on MSC performance in the treatment of diabetic ischemic ulcer", Biomaterials, 34, 2013, pp. 112-120.
Hall et al., "Mesenchymal stromal cells improve survival during sepsis in the absence of heme oxygenase-1: the importance of neutrophils", Stem Cells 31(2), 2013, pp. 397-407.
Burgess et al., "Epoxyeicosatrienoic acids and heme oxygenase-1 interaction attenuates diabetes and metabolic syndrome complications", Prostaglandins & Other Lipid Mediators, 97(0), 2012, 34 pages.
Gieseke et al., "Human multipotent mesenchymal stromal cells use galectin-1 to inhibit immune effector cells", Blood, vol. 116, No. 19, 2010, pp. 3770-3779.
Yang et al., "Enhancement of the immunosuppressive effect of human adipose tissue-derived mesenchymal stromal cells through HLA-G1 expression", Cytotherapy, 14, 2012, pp. 70-79.
Selmani et al., "HLA-G is a crucial immunosuppressive molecule secreted by adult human mesenchymal stem cells", Transplantation, vol. 87, No. 9S, 2009, pp. S62-S66.
Montespan et al., "Osteodifferentiated mesenchymal stem cells from bone marrow and adipose tissue express HLA-G and display immunomodulatory properties in HLA-mismatched settings: implications in bone repair therapy", Journal of Immunology Research, Article ID 230346, 2014, 10 pages.
Fan et al., "Mesenchymal stromal cell supported umbilical cord blood ex vivo expansion enhances regulatory T cells and reduces graft versus host disease", Cytotherapy, 15, 2013, pp. 610-619.
Beyrau et al., "Neutrophil heterogeneity in health and disease: a revitalized avenue in inflammation and immunity", Open Biology, 120134, 2012, 10 pages.
Hotchkiss et al., "The sepsis seesaw: tilting toward immunosuppression", Nature Medicine, 15(5), 2009, pp. 496-497.
Kamp et al., "Human suppressive neutrophils $CD16^{bright}/CD62L^{dim}$ exhibit decreased adhesion", Journal of Leukocyte Biology, vol. 92, 2012, pp. 1011-1020.
Pillay et al., "A subset of neutrophils in human systemic inflammation inhibits T cell responses through Mac-1", The Journal of Clinical Investigation, vol. 122, No. 1, 2012, pp. 327-336.
Forssmann et al., "Eotaxin-2, a novel CC chemokine that is selective for the chemokine receptor CCR3, and acts like eotaxin on human eosinophil and basophil leukocytes", J Exp Med., vol. 185, No. 12, Jun. 16, 1997, pp. 2171-2176.
Eum et al., "Inhibition of allergic airways inflammation and airway hyperresponsiveness in mice by dexamethasone: role of eosinophils, IL-5, eotaxin, and IL-13", The Journal of Allergy and Clinical Immunology, vol. 111, No. 5, 2003, pp. 1049-1061.
Dent et al., "Contribution of eotaxin-1 to eosinophil chemotactic activity of moderate and severe asthmatic sputum", American Journal of Respiratory and Critical Care Medicine, vol. 169, 2004, pp. 1110-1117.
Radinger et al., "Eotaxin-2 regulates newly produced and CD34 airway eosinophils after allergen exposure", The Journal of Allergy and Clinical Immunology, 113, 2004, pp. 1109-1116.
Lezcano-Meza et al., "Interleukin (IL)-4 and to a lesser extent either IL-13 or interferon-gamma regulate the production of eotaxin-2/CCL24 in nasal polyps", Allergy, 58, 2003, pp. 1011-1017.
Chae et al., "The suggestive association of eotaxin-2 and eotaxin-3 gene polymorphisms in Korean population with allergic rhinitis", Immunogenetics, 56, 2005, pp. 760-764.
De Corso et al., "Nasal lavage CCL24 levels correlate with eosinophils trafficking and symptoms in chronic sino-nasal eosinophilic inflammation", Rhinology, 49, 2011, pp. 174-179.
Cavallari et al., "Expression of RANTES, eotaxin-2, ICAM-1, LFA-1 and CCR-3 in chronic rhinosinusitis patients with nasal

(56) References Cited

OTHER PUBLICATIONS polyposis", Acta cirurgica brasileira / Sociedade Brasileira para Desenvolvimento Pesquisa em Cirurgia, vol. 27 (9), 2012, pp. 645-649.

De Corso et al., "Nasal fluid release of eotaxin-3 and eotaxin-2 in persistent sinonasal eosinophilic inflammation", International Forum of Allergy & Rhinology, vol. 4, No. 8, 2014, pp. 617-624.

Chen et al., "Increased serum levels of eotaxin in patients with inflammatory bowel disease," Scandinavian Journal of Gastroenterology, 36, 2001, pp. 515-520.

Manousou et al., "Increased expression of chemokine receptor CCR3 and its ligands in ulcerative colitis: the role of colonic epithelial cells in in vitro studies", Clinical and Experimental Immunology, 162, 2010, pp. 337-347.

Kagami et al., "Significant elevation of serum levels of eotaxin-3/CCL26, but not of eotaxin-2/CCL24, in patients with atopic dermatitis: serum eotaxin-3/CCL26 levels reflect the disease activity of atopic dermatitis", Clinical and Experimental Immunology, 134, 2003, pp. 309-313.

Owczarek et al., "Analysis of eotaxin 1/CCL11, eotaxin 2/CCL24 and eotaxin 3/CCL26 expression in lesional and non-lesional skin of patients with atopic dermatitis", Cytokine, 50, 2010, pp. 181-185.

Owczarek et al., "Relationship between serum eotaxins level and their genes expression in skin of atopic dermatitis patients", Annals of Allergy, Asthma & Immunology: Official Publication of the American College of Allergy, Asthma, & Immunology, 110, 2013, pp. 462-463.

Amerio et al., "Expression of eotaxin, interleukin 13 and tumour necrosis factor-alpha in dermatitis herpetiformis", The British Journal of Dermatology, 143, 2000, pp. 974-978.

Elsner et al., "Eotaxin-2 activates chemotaxis-related events and release of reactive oxygen species via pertussis toxin-sensitive G proteins in human eosinophils", Eur J Immunol., 28(7), Jul. 1998, pp. 2152-2158.

Simmons et al., "Potent inhibition of HIV-1 infectivity in macrophages and lymphocytes by a novel CCR5 antagonist", Science (New York, NY), vol. 276, 1997, pp. 276-279.

Nibbs et al., "C-C chemokine receptor 3 antagonism by the beta-chemokine macrophage inflammatory protein 4, a property strongly enhanced by an amino-terminal alanine-methionine swap", Journal of Immunology (Baltimore, Md : 1950), 164, 2000, pp. 1488-1497.

Supplementary European Search Report in EP Application No. 17841766.3 dated Jan. 24, 2020, 6 pages.

Fan et al., "Application of a Mesenchymal Stromal Cell-Derived Two-factor Cocktail in Graft Versus Host Disease Therapy", Cytotherapy, vol. 19, No. 5, May 1, 2017, Supplement, p. 36.

Yap C. Sun et al., "Substitute Mesenchymal Stromal Cells Therapy in Graft Versus Host Disease With a Chemically Defined Cocktail", J. Clin Cell Immunol, vol. 8, No. 3, Jul. 1, 2017, Supplement, p. 78.

\* cited by examiner

A

B

C

D

METHODS OF TREATING IMMUNOLOGICAL DISORDERS USING IMMUNOSUPPRESSIVE COMPOSITIONS

CROSS-REFERENCE TO RELATED APPLICATIONS

This is a continuation-in-part of U.S. application Ser. No. 16/326,417, which is the U.S. national phase of PCT/SG2017/050408 filed Aug. 18, 2017, which claims priority to SG 10201606949Q filed Aug. 19, 2016, the entire respective disclosures of which are incorporated herein by reference.

FIELD OF THE INVENTION

The present invention relates generally to the field of molecular biology. In particular, the present invention relates to compositions for the treatment of immunological disorders.

BACKGROUND OF THE INVENTION

Mesenchymal stromal cell (MSC) therapy has been shown to be effective in, for example, modulating immunological disorders, alloimmune disease (graft versus host disease (GVHD) after allogeneic hematopoietic cell transplantations) and autoimmune diseases systemic lupus erythematosus (SLE), lupus nephritis, type-I diabetes mellitus, systemic sclerosis, inflammatory bowel disease (IBD), Crohn's disease, etc.). However, MSC therapy trials still face challenges regarding unforeseen long-term complications, potential tumorigenicity and uncontrolled differentiation to unwanted cells or tissue types. Also, the use of human mesenchymal stromal cells raises the question of the equivalence of cells isolated from different sources and using different expansion methods.

Therefore, there is a need for a replacement for mesenchymal stromal cell (MSC) therapy for the treatment of immunological diseases.

SUMMARY

In one aspect, the present invention refers to a method of treating an immunological disorder, the method comprising administration of a pharmaceutical composition comprising CXCL5 (ENA-78).

In one example, the immunological disorder is an alloimmune disease or an autoimmune disease.

In another example, the alloimmune disease is selected from the group consisting of graft versus host disease (GVHD) after allogeneic hematopoietic cell transplantations, alloimmune disease resulting from skin transplant, alloimmune disease resulting from kidney transplant, alloimmune disease resulting from liver transplant, and hemolytic disease of the fetus and newborn.

In yet another example, the autoimmune disease is selected from the group consisting of systemic lupus erythematosus (SLE), diffuse alveolar haemorrhage, lupus nephritis, type-I diabetes mellitus, systemic sclerosis, rheumatoid arthritis, inflammatory bowel disease (IBD) and Crohn's disease.

In a further example, the autoimmune disease is selected from the group consisting of systemic lupus erythematosus (SLE), diffuse alveolar haemorrhage, systemic sclerosis, and rheumatoid arthritis.

In yet another example, the pharmaceutical composition results in a decrease in the concentration of one or more of the circulating pro-inflammatory cytokines selected from the group consisting of IFN-γ, IL-6, IL-17A, IL-8, MIP-1β and MCP-1 in the subject.

In one example, the pharmaceutical composition results an increase or a decrease in the concentration of at least one mesenchymal stromal cell-derived protein in a subject results in an immunosuppressive effect, wherein the mesenchymal stromal cell-derived protein is selected from the group consisting of PGE2 (prostaglandin E2), OPG, CCL7, CCL8, IL-10, CCL20, CXCL5, CXCL6, M-CSF, IL-1β, CCL-1 and CCL24.

In another aspect, the present invention refers to a method of modulating the immune system, the method comprising administration of a pharmaceutical composition to a subject, wherein the pharmaceutical composition comprises CXCL5.

In yet another aspect, the present invention refers to a kit for use in the method disclosed herein, the kit comprising CXCL5.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
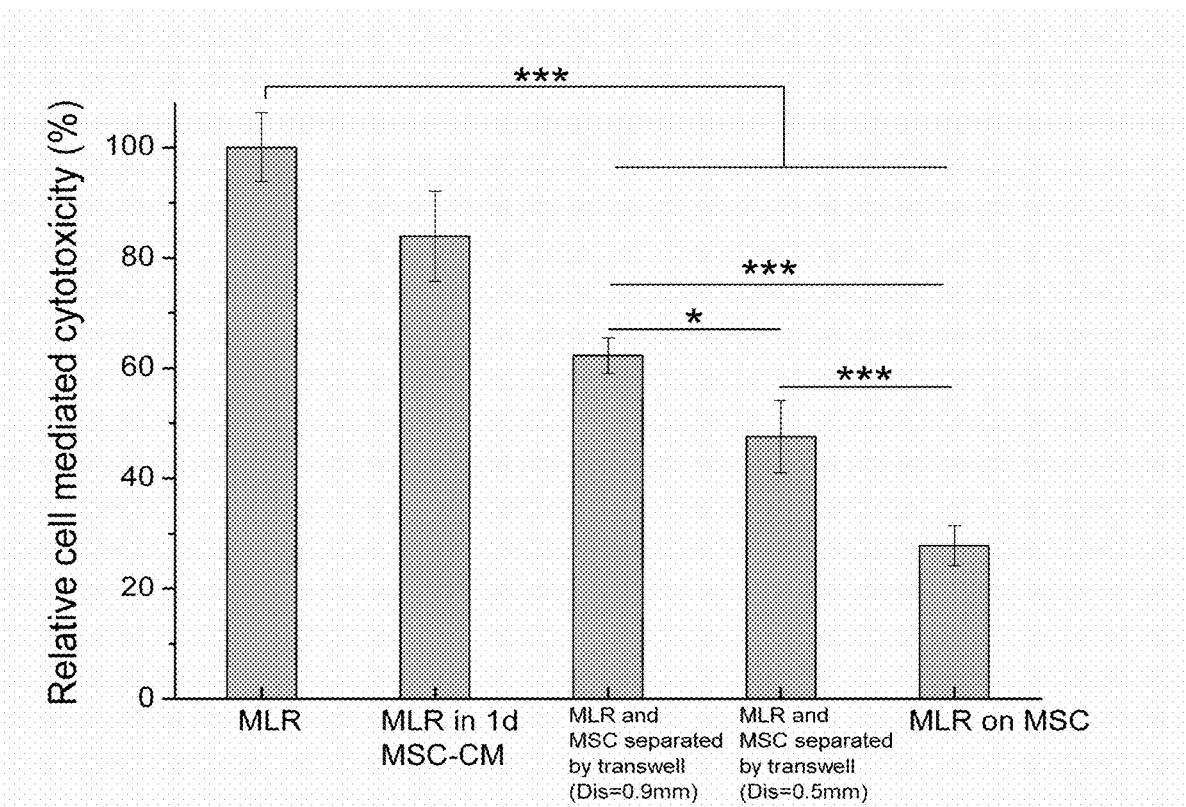
FIG. 1 shows a column graph with data indicating that the immunosuppressive effect of BM-MSC is mainly attributable to soluble factors. Mixed lymphocyte reaction (MLR) experiments were initiated with $1.6 \times 10^5$ of two HLA-mismatched UCB-MNCs at 15:1 E/T ratio for 20 hours. Cell mediated cytotoxicity was determined by LDH detection. Transwell inserts with a pore size of 8 μm were used. The different distance between insert and well bottom was varied. Results were expressed as mean±S.D. For multiple comparisons, Bonferroni's test was used to correct the p-value for t-test (*$p<0.05$; $p<0.01$; *$p<0.001$).

While shown to be effective in modulating or treating immunological disorders, mesenchymal stromal cell (also known as mesenchymal stem cell) therapies come with their own distinct set of unwanted side effects. Disclosed herein are methods and compositions for modulating immune responses, for example unforeseen long-term complications, potential tumorigenicity and uncontrolled differentiation to unwanted cells or tissues.

As used herein, the term "immunological disorder" refers to disorders pertaining to an abnormal reaction of the immune system. Immunological disorders can be classified into immunodeficiency, autoimmune disease and hypersensitivity. Thus, in one example, the immunological disorder is an alloimmune disease or an autoimmune disease.

As used herein, the terms "alloimmune" or "alloimmunity" refer to an immune response to non-self antigens from members of the same species, which are called alloantigens or isoantigens. Two major types of alloantigens are blood group antigens and histocompatibility antigens. In alloimmunity, the body creates antibodies against the alloantigens, attacking transfused blood, allotransplanted tissue, and even the fetus in some cases. Alloimmune (isoimmune) response results in graft rejection, which is manifested as deterioration or complete loss of graft function. In contrast, autoimmunity is an immune response to the self's own antigens. (The allo- prefix means "other", whereas the auto- prefix means "self".) Alloimmunization (isoimmunization) is the process of becoming alloimmune, that is, developing the relevant antibodies for the first time. Without being bound by theory, alloimmunity is thought to be caused by the difference between products of highly polymorphic genes, primarily genes of the major histocompatibility complex, of the donor and graft recipient. These products are recognized by T-lymphocytes and other mononuclear leukocytes which infiltrate the graft and damage it.

The terms "autoimmune" or "autoimmunity" refer to the scenario wherein the system of immune responses of an organism turns against its own healthy cells and tissues. Any disease that results from such an aberrant immune response is termed an autoimmune disease. Prominent examples include, but are not limited to, celiac disease, diabetes mellitus type 1, sarcoidosis, systemic lupus erythematosus (SLE), systemic sclerosis, scleroderma, Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM).

Autoimmune diseases, or immunological disorders in general, are often treated with steroids, among others. The intent is to suppress the aberrant immune response, commonly using immunosuppressants, to which steroid compounds below. The term "immune suppressive", "immunosuppressive" or "immunosuppression" refers to a reduction in the efficacy or the activation/initiation of the immune system. This may or may not influence the immune system's capability of fighting infections. Immunosuppression may result from certain diseases, such as AIDS or lymphoma, or can be induced or caused by using certain drugs, such as some of those used to treat cancer. Immunosuppression may also be deliberately induced with drugs, for example, in preparation for a bone marrow transplant or other organ transplantation, with the view of preventing the rejection of a transplant by the host. Immunosuppression can also be known as immunodepression.

Further examples of autoimmune diseases are, but are not limited to, myocarditis, post-myocardial infarction syndrome, post-pericardiotomy syndrome, sub-acute bacterial endocarditis (SBE), systemic lupus erythematosus (SLE), diffuse alveolar haemorrhage, lupus nephritis, type-I diabetes mellitus, anti-glomerular basement membrane nephritis, interstitial cystitis, autoimmune hepatitis, primary biliary cirrhosis (PBC), primary sclerosing cholangitis, anti-synthetase syndrome, alopecia areata, autoimmune angioedema, autoimmune progesterone dermatitis, autoimmune urticarial, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease (LAD), morphea, pemphigus vulgaris, pityriasis lichenoides et varioliformis acuta, Mucha-Habermann disease, psoriasis, systemic sclerosis, scleroderma, vitiligo, Addison's disease, autoimmune polyendocrine syndrome (APS) type 1, autoimmune polyendocrine syndrome (APS) type 2, autoimmune polyendocrine syndrome (APS) type 3, autoimmune pancreatitis (AIP), autoimmune thyroiditis, Ord's thyroiditis, Graves' disease, autoimmune oophoritis, endometriosis, autoimmune orchitis, Sjögren's syndrome, autoimmune enteropathy, coeliac disease, microscopic colitis, ulcerative colitis, antiphospholipid syndrome (APS, APLS), aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, evans syndrome, paroxysmal nocturnal hemoglobinuria, pernicious anemia, pure red cell aplasia, thrombocytopenia, adiposis dolorosa, adult-onset Still's disease, ankylosing Spondylitis, CREST syndrome, drug-induced lupus, enthesitis-related arthritis, eosinophilic fasciitis, Felty syndrome, IgG4-related disease, juvenile arthritis, Lyme disease (Chronic), mixed connective tissue disease (MCTD), palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, undifferentiated connective tissue disease (UCTD), dermatomyositis, fibromyalgia, inclusion body myositis, myositis, myasthenia gravis, neuromyotonia, paraneoplastic cerebellar degeneration, polymyositis, acute disseminated encephalomyelitis (ADEM), acute motor axonal neuropathy, anti-N-Methyl-D-Aspartate (Anti-NMDA) receptor encephalitis, balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis (pattern II), Oshtoran Syndrome, pediatric Autoimmune Neuropsychiatric Disorder Associated with Streptococcus (PANDAS), progressive inflammatory neuropathy, Restless leg syndrome, Stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease (AIED), Meniere's disease, Behget's disease, eosinophilic granulomatosis with polyangiitis (EGPA), giant cell arteritis, granulomatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumatic, urticarial vasculitis, vasculitis, systemic vasculitis, primary immune deficiency and Crohn's disease.

In another example, the immunological disorder is, but is not limited to, myocarditis, post-myocardial infarction syndrome, post-pericardiotomy syndrome, sub-acute bacterial endocarditis (SBE), systemic lupus erythematosus (SLE), lupus nephritis, type-I diabetes mellitus, systemic sclerosis, scleroderma, rheumatoid arthritis, diffuse alveolar haemorrhage, vasculitis, systemic vasculitis and Crohn's disease. In another example, the immunological disorder is, but is not limited to, systemic lupus erythematosus (SLE), systemic sclerosis, scleroderma, rheumatoid arthritis, vasculitis, systemic vasculitis, and diffuse alveolar haemorrhage. In yet another example, the immunological disorder is, but is not limited to, systemic sclerosis, scleroderma, rheumatoid arthritis, vasculitis, systemic vasculitis, and diffuse alveolar haemorrhage.

Immunological disorders can also be classified by organs and or tissues that are affected by the disorder. For example, the organs and tissue types effected by immunological disorders are, but not limited to, major organs, such as heart, kidney, liver, lung, skin; glands, for example, endocrine, adrenal gland, multi-glandular, pancreas, thyroid gland; exocrine organs, such as reproductive organs, salivary glands; organs of the digestive system; various types of tissue, for example, blood, connective tissue, systemic tissue, and multi-organ tissue, muscle, nervous system, eyes, ears and vascular system.

The term "GVHD", also known as Graft-versus-host-disease, as used herein, refers to a medical complication that can occur after a stem cell or bone marrow transplant. With GVHD, the newly transplanted donor cells attack the transplant recipient's body. GVHD may occur after a bone marrow or stem cell transplant in which someone receives bone marrow tissue or cells from a donor. This type of transplant is called allogeneic. The new, transplanted cells regard the recipient's body as foreign. When this happens, the newly transplanted cells attack the recipient's body. GVHD does not occur when someone receives his or her own cells during a transplant. This type of transplant is called autologous. Before a transplant, tissue and cells from possible donors are checked to see how closely they match the person having the transplant. GVHD is less likely to occur, or symptoms will be milder, when the match is close. The chance of GVHD is around 30 to 40% when the donor and recipient are related and around 60 to 80% when the donor and recipient are not related. There are two types of GVHD: acute and chronic. Symptoms in both acute and chronic GVHD range from mild to severe. Acute GVHD usually happens within the first 6 months after a transplant, while chronic GVHD usually starts more than 3 months after a transplant, and can last a lifetime.

The term "SLE" refers to the disease "systemic lupus erythematosus", an autoimmune disease, whereby the cause is not fully known. In this disease, the body's immune system mistakenly attacks healthy tissue and can affect the skin, joints, kidneys, brain, and other organs. SLE may also be caused by certain drugs.

The term "rheumatoid arthritis" refers to a chronic, systemic autoimmune disease that primarily involves the joints. Rheumatoid arthritis causes damage mediated by cytokines, chemokines and metalloproteases. Characteristically, peripheral joints (for example, but not limited to, wrists and metacarpophalangeal joints) are symmetrically inflamed, leading to progressive destruction of articular structures, usually accompanied by systemic symptoms. Diagnosis is based on specific clinical, laboratory and imaging features. Treatment involves drugs, physical measures, and in some cases, surgery. The use of drugs can be helpful in controlling symptoms and slowing disease progression.

Prominent immunologic abnormalities include immune complexes produced by synovial lining cells and in inflamed blood vessels. Plasma cells produce antibodies (for example, rheumatoid factor (RF)) that contribute to these complexes, but destructive arthritis can occur in the absence of RF. Macrophages also migrate to diseased synovium in early disease; increased macrophage-derived lining cells are prominent along with vessel inflammation. Lymphocytes that infiltrate the synovial tissue are primarily CD4+ T cells. Macrophages and lymphocytes produce pro-inflammatory cytokines and chemokines (for example, tumour necrosis factors (TNFs), granulocyte-macrophage-colony stimulating factor (GM-CSF), various interleukins (ILs), interferon-γ) in the synovium. Release of inflammatory mediators is thought to contribute to the systemic and joint manifestations of rheumatoid arthritis. In chronically affected joints, the normally thin synovium thickens and develops many villous folds. The synovial lining cells produce various materials, including collagenase and stromelysin, which contribute to cartilage destruction and, and IL-1 and TNF-α, which stimulate cartilage destruction, osteoclast-mediated bone absorption, synovial inflammation, and prostaglandins (which potentiate inflammation). Fibrin deposition, fibrosis and necrosis are also present. Hyperplastic synovial tissue (pannus) releases these inflammatory mediators, which erode cartilage, subchrondral bone, articular capsule, and ligaments.

The term "systemic sclerosis", also known as a sub-form of scleroderma, refers to a rare, chronic disease of unknown cause characterised by immune dysregulation, diffuse fibrosis, and vascular abnormalities in the skin, joints and internal organs (especially the oesophagus, lower gastro-intestinal tract, lungs, heart, and kidneys). Common symptoms include, but are not limited to, Raynaud's phenomenon, arthralgia/arthritis, dysphagia, heartburn, skin oedema and thickening, skin tightening and contractures of the fingers. Lungs, heart, and kidney involvement account for most of the deaths caused by systemic sclerosis. Diagnosis is largely clinical, but laboratory tests and examination of the microvasculature at the nailfold help with confirmation. Specific treatment is difficult, and emphasis is often on treatment of complications.

Immunologic mechanisms and heredity (certain HLA-subtypes) are thought to play a role in the etiology of systemic sclerosis. Systemic sclerosis-like symptoms can result from exposure to vinyl chloride, bleomycin, pentazocine, epoxy and aromatic hydrocarbons, contaminated rapeseed oil and L-tryptophan.

Pathophysiology involves vascular damage and activation of fibroblasts; collagen and other extracellular proteins in various tissues are overproduced. In systemic sclerosis, the skin develops more compact collagen fibres, in the reticular dermis, epidermal thinning, loss of rete pegs, and atrophy of dermal appendages. Without being bound by theory, it is thought that T cells are implicated in the pathogenesis and extensive fibrosis in the dermal and subcutaneous layers develops. In the nailfolds, capillary loops dilate and some microvascular loops are lost. In the extremities, chronic inflammation and fibrosis of the synovial membrane and surfaces and periarticular soft tissue occur.

Systemic sclerosis varies in severity and progression. It is divided broadly into limited cutaneous (skin fibrosis distal to the elbows and knees and/or involving the face), and diffuse cutaneous systemic sclerosis (skin fibrosis proximal to the elbows and knees). In general, patients with diffuse cutaneous systemic sclerosis have a worse prognosis with rapid progression and fatal visceral involvement. Systemic sclerosis has one of the worst prognoses among autoimmune diseases with a 10-year survival of 66%. In addition, systemic sclerosis can overlap with other autoimmune rheumatic disorders—for example, systemic lupus erythematosus (SLE), dermatomyositis or polymyositis and mixed connective tissue disease.

As used herein, the term "diffuse alveolar haemorrhage (DAH)" refers to a persistent or recurrent pulmonary haemorrhage. There are numerous causes, but autoimmune disorders are most common. Most patients present with dyspnoea, cough, haemoptysis, and new alveolar infiltrates on chest imaging. Diagnostic tests are directed at the suspected cause. Treatment is with immunosuppressants for patients with autoimmune causes and respiratory support if needed. Diffuse alveolar haemorrhage is not a specific disorder on its own nor is it a specific entity, but is a syndrome that has a specific differential diagnosis and a specific sequence of testing. For example, some disorders that cause diffuse alveolar haemorrhage are associated with glomerulonephritis; then the disorder is defined as a pulmonary-renal syndrome. In another example, diffuse alveolar haemorrhage is seen as a complication of, systemic lupus erythematosus. In yet another example, diffuse alveolar haemorrhage is seen as a complication of systemic vasculitis such as granulomatosis with polyangiitis (formerly known as "Wegener's granulomatosus").

Diffuse alveolar haemorrhage results from widespread damage to the pulmonary small vessels, leading to blood collecting within the alveoli. If enough alveoli are affected, gas exchange is disrupted. The specific pathophysiology and manifestations vary depending on cause. For example, isolated pauci-immune pulmonary capillaritis is a small-vessel vasculitis limited to the lungs; its only manifestation is alveolar haemorrhage affecting people aged 18 to 35 years of age.

As used herein, the term "vasculitis" refers to inflammation of blood vessels, often with ischemia, necrosis, and organ inflammation. Vasculitis can affect any blood vessel—arteries, arterioles, veins, venules, or capillaries. Clinical manifestations of specific vasculitic disorders are diverse and depend on the size and location of the involved vessels, the extent of the organ involvement, and the degree and pattern of inflammation. As used herein, the term "systemic vasculitis" refers to a sub-form of vasculitis.

The term "vasculitis" further describes a pathological process, and can occur as a complication/symptom of most of the autoimmune diseases including, for example, systemic lupus erythematosus (SLE) and rheumatoid arthritis (RA). Traditionally speaking, "systemic vasculitis" refers to a group of diseases, of which granulomatosus with polyangiitis (or Wegener's granumomatosus"), eosinophilic granulomatosus with polyangiitis (or Churg Strauss syndrome), microscopic polyangiitis, among others, are examples of specific diseases under that group.

Certain features (for example, predominant inflammatory cells, location of inflammation) suggest particular vasculitic processes and may aid in the diagnosis. For example, in many acute lesions, the predominant inflammatory cells are polymorphonuclear leukocytes; in chronic lesions, lymphocytes predominate.

Inflammation may be segmental or involve the entire vessel. At sites of inflammation, varying degrees of cellular inflammation and necrosis or scarring occur in one or more layers of the vessel wall. Inflammation in the media of a muscular artery tends to destroy the internal elastic lamina. In some vasculitic disorders, for example granulomatosis with polyangiitis, the vessel inflammation (true vasculitis) is only part of the pathophysiology and there is predominant parenchymal inflammation in a characteristic pattern that involves specific organs.

Without being bound by theory, it has been suggested that mesenchymal stromal cell (MSC; also known as mesenchymal stem cell) mediated immunosuppression works via paracrine signalling, which include a variety of soluble factors such as, for example, transforming growth factor-$\beta$ (TGF-$\beta$), IL-10, hepatocyte growth factor (HGF), indoleamine, dioxygenase (IDO), prostaglandins E2 (PGE2), Nitric oxide (NO), TNF-$\alpha$ stimulated gene/protein 6 (TSG-6), heme oxygenase-1 (HO), galectin-1 and HLA-Gs. Thus, it is shown in the present disclosure that it is possible to use soluble factors that influence paracrine signalling, as those present in the MSC secretome (that is, a cluster of effective soluble factors that is secreted by mesenchymal stromal cells) to emulate the effect of MSC therapy, or even to replace MSC therapy entirely.

As used herein, the term "MSC-derived" or "mesenchymal stromal cell-derived" refers to substances that are obtained or derived from a specific source. In the present disclosure, the term "mesenchymal stromal cell" is a multipotent stromal cell that can differentiate into a variety of cell types, including, but not limited to osteoblasts (bone cells), chondrocytes (cartilage cells), myocytes (muscle cells) and adipocytes (fat cells). These cells are also known as "mesenchymal stem cells" due to their multipotency. This biologically important cell population is able to support hematopoiesis, can differentiate along mesenchymal and non-mesenchymal lineages in vitro, is capable of suppressing alloresponses and appear to be non-immunogenic. These cells are known to either secrete certain proteins and/or compounds, which is turn influence the microenvironment around the cells, or when not directly expressing the proteins themselves, mesenchymal stromal cells are known to influence the downstream expression of other proteins, which for example, may be affected by the presence or absence of a mesenchymal stromal cell. That is to say that the presence of a mesenchymal stromal cell within the environment of another cell can cause the other cell to start producing, or even secreting, certain proteins. Therefore, disclosed herein are both compounds and/or proteins secreted by the mesenchymal stromal cells themselves and are therefore considered to be derived from MSCs as they are specifically obtained from MSCs, as well as proteins and compounds that are produced and/or secreted as a result of the presence of mesenchymal stromal cells within the cell environment. Included therein is also the downstream expression of proteins that is initiated via one or more expression cascades due to the presence of mesenchymal stromal cells in the microenvironment.

Thus, the present disclosure describes, in one example, a pharmaceutical composition comprising at least one antibody and at least one mesenchymal stromal cell-derived protein. In another example, the pharmaceutical composition comprises between 1 to 12 antibodies and proteins. In another example, the pharmaceutical composition comprises 1, 2, 3, or 4 antibodies and 1, 2, 3, 4, 5, 6, 7 or 8 proteins. In another example, the pharmaceutical composition comprises at least two antibodies and at least two proteins. In one example, the method of treatment as disclosed herein comprises the use of at least one antibody and/or at least one mesenchymal stromal cell-derived protein. In another example, the pharmaceutical composition as disclosed herein comprises at least one antibody and at least one mesenchymal stromal cell-derived protein, wherein the antibody targets one or more of the cytokines selected from the group consisting of macrophage colony-stimulating factor (M-CSF), Interleukin-1beta (IL-1$\beta$), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3$\alpha$), CXCL5 (ENA-78), IL-10 and CXCL6 (GCP-2).

As used herein, the term "serial factorial designs" refers a type of statistical experiment design. There are two types of "factorial design". One is a "full factorial design", and another is a "fractional factorial design". In statistics, a full factorial design is an experiment whose design consists of two or more factors, each with discrete possible values or "levels", and whose experimental units take on all possible combinations of these levels across all such factors. Such an experiment allows the investigator to study the effect of each factor on the response variable, as well as the effects of interactions between factors on the response variable. If the number of combinations in a full factorial design is too high to be logistically feasible, a fractional factorial design may be done, in which some of the possible combinations (usually at least half) are omitted. In this present disclosure, two fractional and one full factorial designs were used, hence the term used herein to describe the analysis experiments performed is "serial factorial designs".

As disclosed herein, two mesenchymal stromal cell (MSC)-derived factors were identified that exhibited concerted immunomodulation effect in mixed lymphocyte reaction (MLR) through screening MSC paracrine secretome with factorial design (FD).

The term "mixed lymphocyte reaction (MLR)" refers to an ex vivo, cellular immune assay that occurs between two allogeneic lymphocyte populations (same species but genetically distinct). The assay set-up consists of purifying responder lymphocytes from peripheral blood, thymus, lymph nodes or spleen and co-culturing these with stimulator cells. Stimulator cell populations that also contain T-cells (also known as a two-way mixed lymphocyte reaction) will replicate in the presence of the responder cells, whereas in a one-way mixed lymphocyte reaction, stimulator cells are prevented from replicating by irradiation or treatment with, for example, mitomycin C or a DNA crosslinker to prevent cell replication. The MLR cell-based assay is used in research in order to test, measure and correlate in vitro T cell function and also to elucidate cellular immune function. Furthermore, MLR assays enable the characterization of the lymphocytes, accessory cells (for example, dendritic cells, macrophage and the like) and cytokines that participate in the MLR reactions.

As shown herein, in order to avoid above-mentioned complications, it is intended to replicate and substitute MSC immune-regulatory therapy by its secretome. Ten MSC-derived potential soluble factors accountable for the immunosuppression were shortlisted by cytokine antibody array screening. Six of them (MIP-3a (CCL20), MCP-3 (CCL8), ENA-78 (CXCL5), OPG, GCP-2 (CXCL6), MCP-2 (CCL7)) were upregulated and four of them (M-CSF, IL-113, I-309 (CCL1), and Eotaxin-2 (CCL24)) were downregulated.

In one example, the antibody results in a decrease in concentration of the target cytokine. In one example, the target cytokine is, but is not limited to, one or more of the following: M-CSF, IL-1β, I-309 (CCL1), Eotaxin-2 (CCL24). In another example, the mesenchymal stromal cell-derived protein results in an increase of PGE2, IL-10, OPG, CCL7 (MCP-2), CCL8 (MCP-3), CCL20 (MIP-3α), CXCL5 (ENA-78) or CXCL6 (GCP-2). In yet another example, the antibody results in a decrease in concentration of the target cytokine; and the mesenchymal stromal cell-derived protein results in an increase of PGE2, IL-10, OPG, CCL7 (MCP-2), CCL8 (MCP-3), CCL20 (MIP-3α), CXCL5 (ENA-78) or CXCL6 (GCP-2). In another example, the pharmaceutical composition as disclosed herein results an increase or a decrease in the concentration of at least one mesenchymal stromal cell-derived protein in a subject results in an immunosuppressive effect, wherein the mesenchymal stromal cell-derived protein is selected from the group consisting of PGE2 (prostaglandin E2), OPG, CCL7, CCL8, IL-10, CCL20, CXCL5, CXCL6, M-CSF, IL-1β, CCL-1 and CCL24.

In order to attain the desired effect disclosed in the present application, in one example, the antibody targets one or more of the cytokines. In another example, the one or more cytokines is, but are not limited to, macrophage colony-stimulating factor (M-CSF), Interleukin-1beta (IL-1β), CCL-1 (I-309) and CCL24 (Eotaxin-2).

In one example, the proteins are mesenchymal stromal cell-derived protein. In another example, the mesenchymal stromal cell-derived protein is, but is not limited to, PGE2 (prostaglandin E2), OPG, CCL7 (MCP-2), CCL8 (MCP-3), CCL20 (MIP-3α), CXCL5 (ENA-78), IL-10 and CXCL6 (GCP-2).

As used herein, the terms "increase" and "decrease" refer to the relative alteration of a chosen target or characteristic in a subset of a population (for example a diseased cell) in comparison to the same target or characteristic as present in a control population (for example, a disease free cell) or compared to the whole population. An increase indicates a change on a positive scale, whereas a decrease indicates a change on a negative scale. The term "change", as used herein, also refers to the difference between a chosen target or characteristic of an isolated population subset (for example samples obtained from diseased patients) in comparison to the same trait or characteristic in a control population (for example, samples from disease-free subjects) or in the population as a whole. However, this term is without valuation of the difference seen. Where applicable, the terms "increase" and "decrease" may be replaced with the terms "upregulated" and "downregulated", for example when referring to a change in the expression profile of, for example, genes and proteins.

Inhibiting any of these downregulated proteins or promoting any of these upregulated proteins could not fully mimic the immunosuppressive capability of MSC, suggested that MSC modulated immune reaction through an interacting network of factors. Through serial factorial designs (FD), a two factor (2F)-cocktail comprising CXCL5 and anti-CCL24 antibody was finally established. It exhibited concerted immunomodulation effect in MLR—an in vitro GVHD model. It also showed excellent in vivo immunosuppressive effect in term of ameliorating GVHD and SLE symptoms and improving survival. This identified 2F cocktail could be a potential chemically defined substitute for MSC in immunological disorders therapy.

Thus, in a first aspect the present invention refers to a pharmaceutical composition comprising at least one antibody and at least one mesenchymal stromal cell-derived protein, wherein the antibody targets one or more of the cytokines, wherein the cytokine is, but is not limited to macrophage colony-stimulating factor (M-CSF), Interleukin-1beta (IL-1β), CCL-1 (I-309) and CCL24 (Eotaxin-2); wherein the mesenchymal stromal cell-derived protein is, but is not limited to, PGE2 (prostaglandin E2), IL-10, OPG, CCL7 (MCP-2), CCL8 (MCP-3), CCL20 (MIP-3α), CXCL5 (ENA-78) and CXCL6 (GCP-2).

In one example, one or more antibodies are either anti-CCL1, or anti CCL24, or both, while the one or more mesenchymal stromal cell-derived protein is as defined herein. In another example, one or more antibodies are as disclosed herein, while the one or more mesenchymal stromal cell-derived proteins are, but are not limited to, CXCL5 and OPG. In one example, one or more antibodies are either anti-CCL1, or anti CCL24, or both, while the one or more mesenchymal stromal cell-derived protein is either OPG, or CXCL5, or both. In one example, the antibody is anti-CCL1 in a concentration of 2 μg/ml, and the one or more mesenchymal stromal cell-derived protein is either OPG, or CXCL5 or both. In another example, the antibody is anti-CCL24 in a concentration of 2 μg/ml, and the one or more mesenchymal stromal cell-derived protein is either OPG, or CXCL5 or both. In another example, the antibody is anti-CCL24 and anti-CCL1, both each in a concentration of 2 μg/ml, and the one or more mesenchymal stromal cell-derived protein is either OPG, or CXCL5 or both. In one example, the one or more antibody is anti-CCL1, or anti-CCL24, or both, and the mesenchymal stromal cell-derived protein is OPG in a concentration of 10 ng/ml. In one example, the one or more antibody is anti-CCL1, or anti-CCL24, or both, and the mesenchymal stromal cell-derived protein is CXCL5 in a concentration of 50 ng/ml. In yet one example, the one or more antibody is anti-CCL1, or anti-CCL24, or both, and the mesenchymal stromal cell-derived protein is OPG in a concentration of 10 ng/ml and CXCL5 in a concentration of 50 ng/ml.

In one example, the pharmaceutical composition can comprise the components as provided in Table 1 below, wherein, in on example, the pharmaceutical composition is any composition except for C24a to C27a. In another example, the method is as disclosed herein, wherein the pharmaceutical composition is as shown in Table 1 below.

TABLE 1

List of various compositions

| Composition | |
|---|---|
| C2a | CXCL5; anti-CCL1; anti-IL1b; anti-M-CSF; anti-CCL24 |
| C3a | CCL8; CCL7; OPG; IL-10; anti-CCL24 |
| C4a | CCL8; CCL7; OPG; IL-10; CXCL5; anti-CCL1; anti-IL1b; anti-M-CSF |
| C5a | CCL20; CXCL6; OPG; IL-10; anti-IL1b; anti-M-CSF |
| C6a | CCL20; CXCL6; OPG; IL-10; CXCL5; anti-CCL1; anti-CCL24 |
| C7a | CCL20; CXCL6; CCL8; CCL7; anti-IL1b; anti-M-CSF; anti-CCL24 |
| C8a | CCL20; CXCL6; CCL8; CCL7; CXCL5; anti-CCL1 |
| C9a | PGE2; CXCL6; CCL7; IL-10; anti-CCL1; anti-M-CSF |
| C10a | PGE2; CXCL6; CCL7; IL-10; CXCL5; anti-IL1b; anti-CCL24 |
| C11a | PGE2; CXCL6; CCL8; OPG; anti-CCL1; anti-M-CSF; anti-CCL24 |
| C12a | PGE2; CXCL6; CCL8; OPG; CXCL5; anti-IL1b |
| C13a | PGE2; CCL20; CCL7; OPG; anti-CCL1; anti-IL1b |
| C14a | PGE2; CCL20; CCL7; OPG; CXCL5; anti-M-CSF; anti-CCL24 |
| C15a | PGE2; CCL20; CCL8; IL-10; anti-CCL1; anti-IL1b; anti-CCL24 |
| C16a | PGE2; CCL20; CCL8; IL-10; CXCL5; anti-M-CSF |
| C17a | CXCL5; CXCL6; anti-CCL1; CCL20 |
| C18a | IL-10; OPG; anti-CCL1; CCL20 |
| C19a | IL-10; OPG; CXCL5; CXCL6 |
| C20a | anti-CCL24; OPG; CXCL6; CCL20 |
| C21a | anti-CCL24; OPG; CXCL5; anti-CCL1 |
| C22a | anti-CCL24; IL-10; CXCL6; anti-CCL1 |
| C23a | anti-CCL24; IL-10; CXCL5; CCL20 |
| C24a | anti-CCL1 |
| C25a | anti-CCL24 |
| C26a | OPG |
| C27a | CXCL5 |
| C28a | anti-CCL1; anti-CCL24 |
| C29a | anti-CCL1; OPG |
| C30a | anti-CCL1; CXCL5 |
| C31a | anti-CCL24; OPG |
| C32a | anti-CCL24; CXCL5 |
| C33a | OPG; CXCL5 |
| C34a | anti-CCL1; anti-CCL24; OPG |
| C35a | anti-CCL1; anti-CCL24; CXCL5 |
| C36a | anti-CCL1; OPG; CXCL5 |
| C37a | anti-CCL24; OPG; CXCL5 |
| C38a | anti-CCL1; anti-CCL24; OPG; CXCL5 |

In one example, the pharmaceutical composition comprises CXCL5 and an anti-CCL24 antibody (C32a).

Therefore, in one example, the pharmaceutical composition is according to any one of C2 to C16 as shown in Table 3. In one example, the pharmaceutical composition comprises CXCL5, anti-CCL1, anti-IL-1β, anti M-CSF and anti-CCL24 (C2a). In another example, the pharmaceutical composition comprises CCL8, CCL7, OPG, IL-10 and anti-CCL24 (C3a). In another example, the pharmaceutical composition comprises CCL8, CCL7, OPG, IL-10, CXCL5, anti-CCL1, anti-IL-1β, and anti M-CSF (C4a). In another example, the pharmaceutical composition comprises CCL20, CCL6, OPG, IL-10, anti-IL-113 and anti-M-CSF (C5a). In another example, the pharmaceutical composition comprises CCL20, CXCL6, OPG, IL-10, CXCL5, anti-CCL1, and anti-CCL24 (C6a). In another example, the pharmaceutical composition comprises CCL20, CXCL6, CCL8, CCL7, anti-IL-1β, anti-M-CSF, and anti-CCL24 (C7a). In another example, the pharmaceutical composition comprises CCL20, CXCL6, CCL8, CCL7, CXCL5, and anti-CCL1 (C8a). In another example, the pharmaceutical composition comprises PGE2, CXCL6, CCL7, IL-10, anti-CCL1, and anti-M-CSF (C9a). In another example, the pharmaceutical composition comprises PGE2, CXCL6, CCL7, IL-10, CXCL5, anti-IL-1β, and anti-CCL24 (C10a). In another example, the pharmaceutical composition comprises PGE2, CXCL6, CCL8, OPG, anti-CCL1, anti-M-CSF, and anti-CCL24 (C11a). In another example, the pharmaceutical composition comprises PGE2, CXCL6, CCL8, OPG, CXCL5, and anti-IL-113 (C12a). In another example, the pharmaceutical composition comprises PGE2, CCL20, CCL7, OPG, anti-CCL1, and anti-IL-113 (C13a). In another example, the pharmaceutical composition comprises PGE2, CCL20, CCL7, OPG, CXCL5, and anti-M-CSF and anti-CCL24 (C14a). In another example, the pharmaceutical composition comprises PGE2, CCL20, CCL8, IL-10, anti-CCL1, anti-IL-113 and anti-CCL24 (C15a). In another example, the pharmaceutical composition comprises PGE2, CCL20, CCL8, IL-10, CXCL5 and anti-M-CSF (C16a).

In a further example, the pharmaceutical composition is according to any one of C17 to C23 as shown in Table 4. In one example, the pharmaceutical composition comprises CXCL5, CXCL6, anti-CCL1, and CCL20 (C17a). In another example, the pharmaceutical composition comprises IL-10, OPG, anti-CCL1, and CCL20 (C18a). In one example, the pharmaceutical composition comprises CXCL5, CXCL6, IL-10, and OPG (C19a). In one example, the pharmaceutical composition comprises anti-CCL24, CXCL6, OPG, and CCL20 (C20a). In one example, the pharmaceutical composition comprises anti-CCL24, CXCL5, OPG, and anti-CCL1 (C21a). In one example, the pharmaceutical composition comprises anti-CCL24, CXCL6, IL-10, and CCL1 (C22a). In one example, the pharmaceutical composition comprises anti-CCL24, CXCL5, IL-10, and CCL20 (C23a).

In another example, the pharmaceutical composition is according to any one of C24 to C38 as shown in Table 5. In another example, the pharmaceutical composition comprises anti-CCL24 and anti-CCL1 (C28a). In another example, the pharmaceutical composition comprises OPG and anti-CCL1 (C29a). In another example, the pharmaceutical composition comprises CXCL5 and anti-CCL1 (C30a). In another example, the pharmaceutical composition comprises anti-CCL24 and OPG (C31a). In another example, the pharmaceutical composition comprises anti-CCL24 and CXCL5 (C32a). In another example, the pharmaceutical composition comprises OPG and CXCL5 (C33a). In another example, the pharmaceutical composition comprises anti-CCL24, anti-CCL1 and OPG (C34a). In another example, the pharmaceutical composition comprises anti-CCL24, anti-CCL1, and CXCL5 (C35a). In another example, the pharmaceutical composition comprises OPG, CXCL5 and anti-CCL1 (C36a). In another example, the pharmaceutical composition comprises anti-CCL24 OPG and CXCL5 (C37a). In another example, the pharmaceutical composition comprises anti-CCL24, anti-CCL1, OPG and CXCL5 (C38a). In another example, the pharmaceutical composition comprises PGE2, CCL20, CXCL6, CCL8, CCL7, OPG, IL-10, CXCL5, anti-CCL1, anti-IL1b, anti-M-CSF and anti-CCL24 (full panel as shown in Table 3).

As a person skilled in the art would appreciate, the concentrations of the individual components disclosed herein are to be present in a concentration capable of or resulting in the desired effect, which is the modulation of the host immune system.

Thus, in one example, the pharmaceutical composition is as disclosed herein, wherein the antibody is present in a concentration of about 0.05 µg to 5 µg, 0.05 µg to 0.7 µg, 0.5 µg/ml to about 5 µg/ml, about 1 µg/ml to about 2 µg/ml, about 2 g/ml to about 3.5 µg/ml, about 4 µg/ml to about 5 µg/ml, about 2 g/ml to about 4.5 µg/ml, about 0.05n, about 0.1 µg, about 0.25n, about 0.5 µg/ml, about 0.75 µg/ml, about 1 µg/ml, about 1.25 µg/ml, about 1.5 µg/ml, about 2.25 µg/ml, about 2.5 µg/ml, about 2.75 µg/ml, about 3.75 µg/ml, or about 4.8 µg/ml. In one example, the antibody is present in a concentration of about 1 µg/ml or about 2 µg/ml. The concentration of each antibody in a pharmaceutical composition is selected independently from all other components of the pharmaceutical composition. In one example, the concentration of anti-IL-1β, anti-M-CSF, independently, is less than 3 µg/ml, less than 2 µg/ml, or less than 1.5 µg/ml. In another example, the concentration of anti-CCL1 and anti-CCL24, independently, is less than 6 µg/ml, less than 5 µg/ml or less than 2.5 µg/ml.

Figure 3:
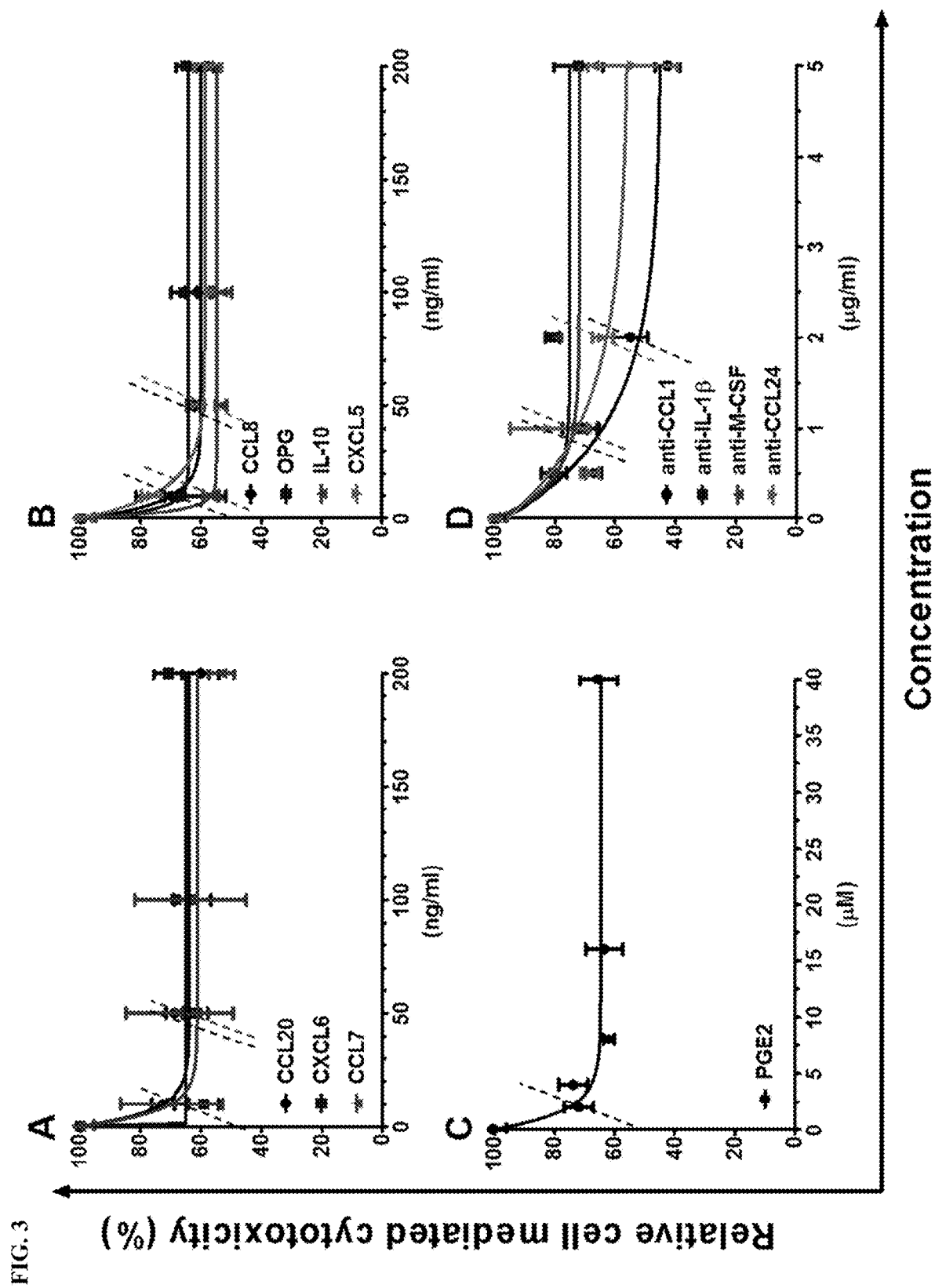
FIG. 3 shows dose response curves showing the determination of the optimal working concentration of each factor. (A-C) Dose response curves of upregulated factors. (D) Dose response curves of antibodies against downregulated factors. The titration was carried out on MLR system with 15:1 E/T ratio for 20 hours. Cell mediated cytotoxicity was determined by LDH detection. Results were expressed as mean±S.D.

In one example, the pharmaceutical composition is as disclosed herein, wherein the mesenchymal stromal cell-derived protein is present in a concentration of about 0.5 ng/mg to about 75 ng/ml, about 0.5 to about 10 ng/ml, about 0.5 to about 1 ng/ml, about 0.75 to about 5 ng/ml, 5 ng/ml to about 75 ng/ml, about 10 ng/ml to about 50 ng/ml, about 20 ng/ml to about 40 ng/ml, about 30 ng/ml to about 65 ng/ml, about 40 ng/ml to about 55 ng/ml, about 0.5 ng/ml, about 1 ng/ml, about 5 ng/ml, about 8 ng/ml, about 9 ng/ml, about 10 ng/ml, about 15 ng/ml, about 25 ng/ml, about 34 ng/ml, about 40 ng/ml, about 45 ng/ml, about 50 ng/ml, about 55 ng/ml, about 58 ng/ml, about 65 ng/ml, or about 70 ng/ml. In another example, the mesenchymal stromal cell-derived protein is present in a concentration of about 10 ng/ml or 50 ng/ml. The concentration of each mesenchymal stromal cell-derived protein in a pharmaceutical composition is selected independently from all other components of the pharmaceutical composition. In one example, the concentration of each of CCL20, CCL8, CCL7, CXCL6, CXCL5, OPG and IL-10, independently, is less than 60 ng/ml, less than 50 ng/ml, or less than 30 ng/ml. As shown in FIG. 3, the immunosuppressive effect of individual proteins would reach a plateau in the event that more than 50 ng/ml of protein is added during experimental analysis.

In one example, the pharmaceutical composition comprises CXCL6, OPG and IL-10 in a concentration of between about 5 µg/ml and about 15 µg/ml, CXCL5 and CCL20 in a concentration of between about 45 µg/ml and 55 µg/ml, and anti-CCL1 and anti-CCL24 in a concentration of between about 1 µg/ml and 2.5 µg/ml. In another example, the pharmaceutical composition comprises CXCL6, OPG and IL-10 in a concentration of about 10 µg/ml, CXCL5 and CCL20 in a concentration of about 50 µg/ml, and anti-CCL1 and anti-CCL24 in a concentration of about 2 µg/ml (C6; also termed 7F). In one example, the pharmaceutical composition comprises anti-CCL24 and anti-CCL1 in a concentration of between about 1 to 2.5 µg/ml, CXCL5 at a concentration of between about 45 µg/ml to 55 µg/ml, and OPG at a concentration of between about 5 µg/ml to 15 µg/ml. In another example, the pharmaceutical composition comprises anti-CCL24 and anti-CCL1 in a concentration of about 2 µg/ml, CXCL5 at a concentration of about 50 µg/ml, and OPG at a concentration of between about 10 µg/ml (C21). In one example, the pharmaceutical composition comprises anti-CCL24 in a range of 1 to 2.5 µg/ml and CXCL5 in a range of 40 to 60 ng/ml. In another example, the pharmaceutical composition comprises anti-CCL24 at a concentration of 2 µg/ml and CXCL5 in a concentration of 50 ng/ml (C32).

In one embodiment, there is disclosed a pharmaceutical composition comprising at least one antibody and at least one mesenchymal stromal cell-derived protein, wherein the antibody targets one or more of the cytokines selected from the group consisting of macrophage colony-stimulating factor (M-CSF), Interleukin-1beta (IL-1β), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3α), CXCL5 (ENA-78), IL-10 and CXCL6 (GCP-2).

In one example, the present application discloses the pharmaceutical composition described herein, wherein the pharmaceutical composition is as shown in the table below:

| | Composition |
|---|---|
| C2a | CXCL5; anti-CCL1; anti-IL1b; anti-M-CSF; anti-CCL24 |
| C3a | CCL8; CCL7; OPG; IL-10; anti-CCL24 |
| C4a | CCL8; CCL7; OPG; IL-10; CXCL5; anti-CCL1; anti-IL1b; anti-M-CSF |
| C5a | CCL20; CXCL6; OPG; IL-10; anti-IL1b; anti-M-CSF |
| C6a | CCL20; CXCL6; OPG; IL-10; CXCL5; anti-CCL1; anti-CCL24 |
| C7a | CCL20; CXCL6; CCL8; CCL7; anti-IL1b; anti-M-CSF; anti-CCL24 |
| C8a | CCL20; CXCL6; CCL8; CCL7; CXCL5; anti-CCL1 |
| C9a | PGE2; CXCL6; CCL7; IL-10; anti-CCL1; anti-M-CSF |
| C10a | PGE2; CXCL6; CCL7; IL-10; CXCL5; anti-IL1b; anti-CCL24 |
| C11a | PGE2; CXCL6; CCL8; OPG; anti-CCL1; anti-M-CSF; anti-CCL24 |
| C12a | PGE2; CXCL6; CCL8; OPG; CXCL5; anti-IL1b |
| C13a | PGE2; CCL20; CCL7; OPG; anti-CCL1; anti-IL1b |
| C14a | PGE2; CCL20; CCL7; OPG; CXCL5; anti-M-CSF; anti-CCL24 |
| C15a | PGE2; CCL20; CCL8; IL-10; anti-CCL1; anti-IL1b; anti-CCL24 |
| C16a | PGE2; CCL20; CCL8; IL-10; CXCL5; anti-M-CSF |
| C17a | CXCL5; CXCL6; anti-CCL1; CCL20 |
| C18a | IL-10; OPG; anti-CCL1; CCL20 |
| C19a | IL-10; OPG; CXCL5; CXCL6 |
| C20a | anti-CCL24; OPG; CXCL6; CCL20 |
| C21a | anti-CCL24; OPG; CXCL5; anti-CCL1 |
| C22a | anti-CCL24; IL-10; CXCL6; anti-CCL1 |
| C23a | anti-CCL24; IL-10; CXCL5; CCL20 |
| C28a | anti-CCL1; anti-CCL24 |
| C29a | anti-CCL1; OPG |
| C30a | anti-CCL1; CXCL5 |
| C31a | anti-CCL24; OPG |
| C32a | anti-CCL24; CXCL5 |
| C33a | OPG; CXCL5 |
| C34a | anti-CCL1; anti-CCL24; OPG |
| C35a | anti-CCL1; anti-CCL24; CXCL5 |
| C36a | anti-CCL1; OPG; CXCL5 |
| C37a | anti-CCL24; OPG; CXCL5 |
| C38a | anti-CCL1; anti-CCL24; OPG; CXCL5 |

In another example, the present application discloses the pharmaceutical composition as described herein, wherein the pharmaceutical composition comprises CXCL5 and an anti-CCL24 antibody (C32a).

In yet another example, the present application discloses the pharmaceutical composition as described herein, wherein the antibody is present in a concentration of about 0.05 µg/ml to about 5 µg/ml.

In a further example, the present application discloses the pharmaceutical composition as described herein, wherein the antibody is present in a concentration of about 1 µg/ml or about 2 µg/ml.

In one example, the present application discloses the pharmaceutical composition as described herein, wherein the mesenchymal stromal cell-derived protein is present in a concentration of about 0.5 ng/ml to about 75 ng/ml.

In another example, the present application discloses the pharmaceutical composition as described herein, wherein the mesenchymal stromal cell-derived protein is present in a concentration of about 10 ng/ml or 50 ng/ml.

In another embodiment, there is disclosed a method of treating an immunological disorder, the method comprising administration of a pharmaceutical composition comprising at least one antibody and/or at least one mesenchymal stromal cell-derived protein, wherein the antibody targets one or more of the cytokines selected from the group consisting of macrophage colony-stimulating factor (M-CSF), Interleukin-1beta (IL-1β), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3α), CXCL5 (ENA-78), IL-10 and CXCL6 (GCP-2).

In yet another embodiment, there is disclosed a method of modulating the immune system, the method comprising administration of a pharmaceutical composition as described herein.

In one example, the present application discloses the method described herein, wherein the pharmaceutical composition is as shown in the table below:

| Composition | |
|---|---|
| C2a | CXCL5; anti-CCL1; anti-IL1b; anti-M-CSF; anti-CCL24 |
| C3a | CCL8; CCL7; OPG; IL-10; anti-CCL24 |
| C4a | CCL8; CCL7; OPG; IL-10; CXCL5; anti-CCL1; anti-IL1b; anti-M-CSF |
| C5a | CCL20; CXCL6; OPG; IL-10; anti-IL1b; anti-M-CSF |
| C6a | CCL20; CXCL6; OPG; IL-10; CXCL5; anti-CCL1; anti-CCL24 |
| C7a | CCL20; CXCL6; CCL8; CCL7; anti-IL1b; anti-M-CSF; anti-CCL24 |
| C8a | CCL20; CXCL6; CCL8; CCL7; CXCL5; anti-CCL1 |
| C9a | PGE2; CXCL6; CCL7; IL-10; anti-CCL1; anti-M-CSF |
| C10a | PGE2; CXCL6; CCL7; IL-10; CXCL5; anti-IL1b; anti-CCL24 |
| C11a | PGE2; CXCL6; CCL8; OPG; anti-CCL1; anti-M-CSF; anti-CCL24 |
| C12a | PGE2; CXCL6; CCL8; OPG; CXCL5; anti-IL1b |
| C13a | PGE2; CCL20; CCL7; OPG; anti-CCL1; anti-IL1b |
| C14a | PGE2; CCL20; CCL7; OPG; CXCL5; anti-M-CSF; anti-CCL24 |
| C15a | PGE2; CCL20; CCL8; IL-10; anti-CCL1; anti-IL1b; anti-CCL24 |
| C16a | PGE2; CCL20; CCL8; IL-10; CXCL5; anti-M-CSF |
| C17a | CXCL5; CXCL6; anti-CCL1; CCL20 |
| C18a | IL-10; OPG; anti-CCL1; CCL20 |
| C19a | IL-10; OPG; CXCL5; CXCL6 |
| C20a | anti-CCL24; OPG; CXCL6; CCL20 |
| C21a | anti-CCL24; OPG; CXCL5; anti-CCL1 |
| C22a | anti-CCL24; IL-10; CXCL6; anti-CCL1 |
| C23a | anti-CCL24; IL-10; CXCL5; CCL20 |
| C24a | anti-CCL1 |
| C25a | anti-CCL24 |
| C26a | OPG |
| C27a | CXCL5 |
| C28a | anti-CCL1; anti-CCL24 |
| C29a | anti-CCL1; OPG |
| C30a | anti-CCL1; CXCL5 |
| C31a | anti-CCL24; OPG |
| C32a | anti-CCL24; CXCL5 |
| C33a | OPG; CXCL5 |
| C34a | anti-CCL1; anti-CCL24; OPG |
| C35a | anti-CCL1; anti-CCL24; CXCL5 |
| C36a | anti-CCL1; OPG; CXCL5 |
| C37a | anti-CCL24; OPG; CXCL5 |
| C38a | anti-CCL1; anti-CCL24; OPG; CXCL5 |

In another example, the present application discloses the method as described herein, wherein the pharmaceutical composition comprises CXCL5 and an anti-CCL24 antibody (C32a).

In yet another example, the present application discloses the method as described herein, wherein the immunological disorder is an alloimmune disease or an autoimmune disease.

In a further example, the present application disclose the method as described herein, wherein the alloimmune disease is selected from the group consisting of graft versus host disease (GVHD) after allogeneic hematopoietic cell transplantations, alloimmune disease resulting from skin transplant, alloimmune disease resulting from kidney transplant, alloimmune disease resulting from liver transplant, and hemolytic disease of the fetus and newborn.

In yet another example, the present application discloses the method as described herein, wherein the autoimmune disease is selected from the group consisting of systemic lupus erythematosus (SLE), lupus nephritis, type-I diabetes mellitus, systemic sclerosis, inflammatory bowel disease (IBD) and Crohn's disease.

In a further example, the present application discloses the method as disclosed herein, wherein the pharmaceutical composition results in a decrease in the concentration of one or more of the circulating pro-inflammatory cytokines selected from the group consisting of IFN-γ, IL-6, IL-17A, IL-8, MIP-1β and MCP-1 in the subject.

In one example, the present invention discloses the method as described herein, wherein the pharmaceutical composition results an increase or a decrease in the concentration of at least one mesenchymal stromal cell-derived protein in a subject results in an immunosuppressive effect, wherein the mesenchymal stromal cell-derived protein is selected from the group consisting of PGE2 (prostaglandin E2), OPG, CCL7, CCL8, CCL20, IL-10, CXCL5, CXCL6, M-CSF, IL-1β, CCL-1 and CCL24.

In a further embodiment, there is disclosed a kit comprising at least one antibody and at least one mesenchymal stromal cell-derived protein as defined herein.

Also disclosed herein is a method of treating an immunological disorder. In one example, the method of treating an immunological disorder comprises administration of a pharmaceutical composition comprising at least one antibody and/or at least one mesenchymal stromal cell-derived protein, wherein the antibody targets one or more of the cytokines selected from the group consisting of macrophage colony-stimulating factor (M-CSF), Interleukin-1beta (IL-1β), CCL-1 (I-309) and CCL24 (Eotaxin-2); wherein the mesenchymal stromal cell-derived protein is selected from the group consisting of PGE2 (prostaglandin E2), OPG, CCL7 (MCP-2), CCL8 (MCP-3), CCL20 (MIP-3α), CXCL5 (ENA-78), IL-10 and CXCL6 (GCP-2). Thus, in one example, the immunological disorder is an alloimmune disease or an autoimmune disease. In one example, the alloimmune disease is selected from the group consisting of graft versus host disease (GVHD) after allogeneic hematopoietic cell transplantations, alloimmune disease resulting from skin transplant, alloimmune disease resulting from kidney transplant, alloimmune disease resulting from liver transplant, and hemolytic disease of the fetus and newborn. In another example, the autoimmune disease is selected from the group consisting of systemic lupus erythematosus (SLE), lupus nephritis, type-I diabetes mellitus, and Crohn's disease.

In one example, the method comprises administration of the pharmaceutical composition as defined herein. In another example, disclosed herein is a method of modulating the immune system, the method comprising administration of a pharmaceutical composition as defined herein. In another example, the method is as disclosed herein, wherein the pharmaceutical composition results an increase or a decrease in the concentration of at least one mesenchymal stromal cell-derived protein in a subject results in an immunosuppressive effect, wherein the mesenchymal stromal cell-derived protein is, but is not limited to, PGE2 (prostaglandin E2), OPG, CCL7, CCL8, CCL20, CXCL5, CXCL6, M-CSF, IL-1β, CCL-1 and CCL24. In another example, the method is as disclosed herein, wherein the pharmaceutical composition results in a decrease in the concentration of one or more of the circulating pro-inflammatory cytokines, whereby the cytokines are, but are not limited to IFN-γ, IL-6, IL-17A, IL-8, MIP-1β and MCP-1 in the subject. In one example, the method comprises administration of the pharmaceutical composition comprising CXCL5 and an anti-CCL24 antibody (C32a). In another example, the method comprises administration of a pharmaceutical composition comprising CXCL5 (C27a).

In one example, the method is as disclosed herein, wherein the pharmaceutical composition is according to any one of C2 to C16 as shown in Table 3. In another example, the method is as disclosed herein, wherein the pharmaceutical composition is according to any one of C17 to C23 as shown in Table 4. In yet another example, the method is as disclosed herein, wherein the pharmaceutical composition is according to any one of C24 to C38 as shown in Table 5. In a further example, the method is as disclosed herein, wherein the pharmaceutical composition comprises CXCL5 and an anti-CCL24 antibody (for example, C32 in Table 5 or C32a in Table 1). In yet another example, the method is as disclosed herein, wherein the pharmaceutical composition comprises CXCL5 (for example, C27a in Table 1 or C27 in Table 5). In one example, the mesenchymal stromal cell-derived protein is CXCL5 (ENA-78).

The identified 2 factor "2F" cocktail, comprising CXCL5 and anti-CCL24 antibody, also showed in vivo immunosuppressive effect in ameliorating GVHD and systemic lupus erythematosus (SLE) symptoms and improving survival. In GVHD, it is shown to reduce cytotoxic T lymphocytes (CTLs), Th1 cells, Th17 cells, natural killer (NK) cells in the circulation and macrophages in the spleen, but not to affect human hematopoietic stem cells (HSCs) reconstitution in the bone marrow. Concurrently, it is shown to reduce pro-inflammatory cytokine IFN-γ, IL-6, IL-17A, IL-8, MIP-1β and MCP-1 in the circulation. In SLE, it is shown to reduce helper T cells, dendritic cells (DCs), monocytes and/or macrophages and natural killer cells (NK cells). Without being bound by theory, these results indicated the 2F cocktail mimics the immunomodulatory effect of MSCs by suppressing the proliferation and differentiation of multiple effector cells and reducing the secretion of a cluster of pro-inflammatory cytokines.

Thus, in one example, the pharmaceutical composition is as disclosed herein, wherein the pharmaceutical composition results in a reduction in the presence of at least one cell type, but not limited to, circulating cytotoxic T lymphocytes (CTLs), T helper 1 (Th1) cells, T helper 17 (Th17) cells, and natural killer (NK) cells of a subject, as well as splenic macrophages and NK cells of a subject in GVHD; helper T cells, DCs, monocytes/macrophages and NK cells of a subject in SLE.

ENA-78 (epithelial-derived neutrophil-activating protein 78, also called CXCL5) is a member of the CXC chemokines and acts as a potent chemo-attractant and activator of neutrophils through CXCR2 receptor. It therefore plays an important role in mediating allergic conditions, and inflammatory disorders. Neutrophils are traditionally considered, to be short-lived (6-8 h), terminally differentiated cells that do not recirculate. The potential existence of distinct neutrophil subsets with functional and phenotypic heterogeneity has not been widely considered or explored. However, more and more evidence is now challenging this scenario, and there is significant evidence for the existence of different neutrophil subsets under both physiological and pathological conditions. In severe systemic inflammation elicited by trauma or sepsis, neutrophils play a critical role. They contribute to collateral tissue damage during the initial inflammatory stage of sepsis. However, most deaths occur during the later compensatory anti-inflammatory response stage of the disease, when patients develop immunosuppression and succumb to additional infections. The latter indicates that despite notable neutrophilia, the host is immunocompromised and more prone to infections, suggesting alterations in the effector functions of neutrophils. Within this, it was revealed that systemic LPS leads to the presence of a previously undescribed neutrophil subset characterized by a distinct $CD16^{bright}CD62L^{dim}$ phenotype that was also detected in patients who had suffered severe injury. This neutrophil subset exhibited hyper segmented nuclear morphology, increased capability to produce ROS and suppressive T-cell proliferation via expression of Mac-1 and locally released ROS-dependent inhibition of T cell proliferation.

Eotaxin-2 (eosinophil chemotactic protein-2, also called CCL24) is small cytokine belonging to the CC chemokine family. CCL24 interacts with chemokine receptor CCR3 and exerts its activity on eosinophils, resting T cells and basophils. Eotaxins have been well documented its role in allergic conditions (such as asthma and rhinitis) and other inflammatory disorders characterized by eosinophils accumulation (inflammatory bowel disease, atopic dermatitis and dermatitis herpetiformis) through the release of reactive oxygen species (ROS) and induction of histamine and LTC-4 degranulation in basophils. It has been proposed as a therapeutic target for these conditions using antibodies against eotaxins or interfering eotaxin receptor with modified chemokines, small molecules specific antagonists for CCR3 and anti-CCR3 antibodies.

Without being bound by theory, based on the biological property of these two chemokines, it is possible to understand the immunosuppressive capacity of anti-CCL24 antibody. Anti-CCL24 antibody is shown to inhibit the proliferation of T cells, especially with regard to cytotoxic T lymphocytes (CTLs), Th1 and Th17 cells. The reduction of these three cell populations results in a reduction of IFN-γ secretion. Thus the proliferation of natural killer (NK) cells and macrophages is further reduced in a cascading manner. All these repressed effector cells contribute to the immunosuppression. However, the immunosuppressive effect of chemokine CXCL5 found in the present application appears to run against to the general understanding of what CXCL5 does. Normally, CXCL5 is a neutrophil chemoattractant and will recruit more neutrophils if its concentration is increased. However, as shown herein, CXCL5 suppresses the proliferation of multiple effector cells, and reduces the pro-inflammatory cytokine secretion. Without being bound by theory, it is thought that CXCL5 exerts its immunosuppressive function through three possible mechanisms: (1) instantaneously increased CXCL5 concentration in blood by intravenous injection may reverse the chemokine gradient between the blood (high) and inflammatory tissues (low). This helps to recruit the infiltrated neutrophils and macrophages back from the inflammatory tissues to blood and release the inflammation burden in the tissues. This concept has been corroborated by the less lymphocyte infiltration in skin, intestine and kidney of GVHD mice as shown herein. (2) CXCL5 may help to promote the proliferation of immunosuppressive neutrophils. This neutrophil subset is characterized by a distinct $CD16^{bright}CD62L^{dim}$ phenotype and has demonstrated immunosuppression capacity in patients who have suffered severe injury. This neutrophil subset exhibits hypersegmented nuclear morphology, increased capability to produce ROS and suppressive T-cell proliferation via expression of Mac-1 and locally released ROS-dependent inhibition of T cell proliferation. In the xenograft GVHD model shown herein, there were no viable granulocytes in the cryopreserved PBMCs after two rounds of freeze/thaw processing. Hence, in the short run GVHD mice model, there were no human neutrophils, eosinophils and basophils engrafted due to the limitation of the animal model per se. However, a distinct mouse immunosuppressive neutrophil ($Ly6G^+CD11b^+$) population was observed when mice were treated with the 2FC (data not shown). This highly promoted mouse immunosuppressive neutrophils might also assist to ameliorate GVHD symptoms and improve mice survival. (3) CXCL5 concerts anti-CCL24 to suppress immune reaction through other immune cell types. In the in vitro screening model, the MLR was set up with two HLA-mismatched mononuclear cells, in which the granulocytes were removed by Ficoll-paque isolation. CXCL5 was still screened out as the key immunomediator even though there are no neutrophils involved in the reaction. Without being bound by theory, this result suggests that CXCL5 exerts its immunosuppressive function through other immune cell types.

Also disclosed herein is the use of a single factor composition. In one example, such a single factor composition comprises CXCL5.

In one example, there is disclosed the use of CXCL5 in a method of treating systemic lupus erythematosus (SLE). In one example, there is disclosed the use of CXCL5 in a method of treating diffuse alveolar haemorrhage. In one example, there is disclosed the use of CXCL5 in a method of treating systemic sclerosis. In one example, there is disclosed the use of CXCL5 in a method of treating scleroderma. In one example, there is disclosed the use of CXCL5 in a method of treating vasculitis. In one example, there is disclosed the use of CXCL5 in a method of treating systemic vasculitis. In one example, there is disclosed the use of CXCL5 in a method of treating rheumatoid arthritis.

As shown in the experimental section below, CXCL5 chemokine was directly administered to mouse model of diffuse alveolar haemorrhage (DAH), which is a symptom presenting with, for example, systemic lupus erythematosus (SLE) or vasculitis; collagen-induced arthritis (CIA; a mouse model for studying rheumatoid arthritis) and bleomycin-induced scleroderma (a mouse model for the study of systemic sclerosis) intravenously. The therapeutic effect was evaluated by improving mice survival and reducing symptoms. The working mechanism was dissected by flow cytometry analysis and Luminex assay.

Result of these experiments showed that CXCL5 reduced the prevalence of diffuse alveolar haemorrhage from 77.8% to 50.0% (p<0.05) via concordant effect of suppressing pulmonary neutrophils infiltration, reducing the accumulation of macrophages and B cells in bronchoalveolar lavage fluid (BALF) and proliferation of neutrophils in blood. In mild collagen-induced arthritis, CXCL5 mimicked bone marrow mesenchymal stem cells (BM-MSCs) to slow down the development of arthritis and eventually reduced the disease activity index (DAI) from 11.4±3.8 (dPBS) to 8.7±4.2 (CXCL5) and 9.2±5.1 (MSCs) by suppressing the proliferation of monocytes, B cells and $T_H1$ cells in blood. In bleomycin-induced systemic sclerosis, CXCL5 reduced the skin thickness from 346.1±37.9 μm (dPBS) to 277.2±47.6 μm, which was improved over what was shown with bone marrow mesenchymal stem cells (330.2±84.2 μm) and Prednisolone (309.0±95.3 μm) (p<0.05). Meanwhile, the leukocyte infiltration in skin was also reduced from 6.5±1.9 cells/HPF (dPBS) to 2.3±2.0 cells/HPF (CXCL5). Without being bound by theory, it was thought that this reduction in leukocyte filtration was done by suppressing the proliferation of monocytes and $T_H1$ cells in blood. In systemic lupus erythematosus, mCXCL5 (murine CXCL5) was thought to ameliorate the symptoms and prolong survival of attenuated $Fas^{lpr}$SLE mice by 70% by suppressing neutrophils, $T_H17$ and monocytes/macrophages.

Thus, in one example, there is disclosed use of the CXCL5 chemokine as a drug to treat inflammatory disorders. In another example, CXCL5 can be used in the treatment of inflammatory or autoimmune diseases as disclosed herein. In another example, CXCL5 can be used in the treatment of one or more diseases, which are, but are not limited to, graft versus host disease (GVHD), systemic lupus erythematosus (SLE), diffuse alveolar haemorrhage, systemic sclerosis, scleroderma, vasculitis, systemic vasculitis, and rheumatoid arthritis. In another example, CXCL5 can be used in the treatment of one or more diseases, which are, but are not limited to, systemic lupus erythematosus (SLE), diffuse alveolar haemorrhage, systemic sclerosis, scleroderma, vasculitis, systemic vasculitis, and rheumatoid arthritis.

The present disclosure also describes a kit comprising at least one antibody and at least one mesenchymal stromal cell-derived protein as defined herein. Also disclosed herein is a kit comprising CXCL5 for use in the methods disclosed herein.

The peptide, the antibody or the pharmaceutical composition as described herein and above can be formulated into compositions suitable for administration. Where applicable, a peptide and/or an antibody may be administered with a pharmaceutically acceptable carrier. A "carrier" can include any pharmaceutically acceptable carrier as long as the carrier can is compatible with other ingredients of the formulation and not injurious to the patient. Accordingly, pharmaceutical compositions for use may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Thus, in one example, the present disclosure described a pharmaceutical composition comprising, but not limited to, at least one peptide as described herein and at least one antibody as described herein. In one example, the pharmaceutical composition comprises a peptide as described herein. In another example, the pharmaceutical composition comprises an antibody as described herein. In yet another example, the pharmaceutical composition further comprises one or more pharmaceutically acceptable excipients, vehicles or carriers. Therefore, in one example, the peptide as disclosed herein may further comprise a compound selected from, but not limited to, a pharmaceutically acceptable carrier, a liposomal carrier, an excipient, an adjuvant or combinations thereof.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients. In one example, the pharmaceutical composition described herein is formulated for parenteral administration. In another example, the pharmaceutical composition described herein is formulated for intravenous administration. In another example, the pharmaceutical composition is formulated as admixture, whereby, for example, each compound is provided separately, to be mixed shortly before administration.

Compositions as described herein include, but are not limited to, solutions, emulsions, and liposome-containing formulations. These compositions may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The composition, shape, and type of dosage forms of the pharmaceutical composition as disclosed herein will typically vary depending on the intended use. For example, a dosage form used in the acute treatment of a disease or a related disease may contain larger amounts of one or more of the active compound it comprises than a dosage form used in the chronic treatment of the same disease. Similarly, a parenteral dosage form may contain smaller amounts of one or more of the active compound it comprises than an oral dosage form used to treat the same disease or disorder. These and other ways in which specific dosage forms encompassed by this invention will vary from one another will be readily apparent to those skilled in the art. Examples of dosage forms include, but are not limited to: tablets; caplets; capsules, such as soft elastic gelatine capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient. Thus, in one example, the pharmaceutical composition as disclosed herein is provided in a form selected from, but not limited to, tablets, caplets, capsules, hard capsules, soft capsules, soft elastic gelatine capsules, hard gelatine capsules, cachets, troches, lozenges, dispersions, suppositories, ointments, cataplasms, poultices, pastes, powders, dressings, creams, plasters, solutions, injectable solutions, patches, aerosols, nasal sprays, inhalers, gels, suspensions, aqueous liquid suspensions, non-aqueous liquid suspensions, oil-in-water emulsions, a water-in-oil liquid emulsions, solutions, sterile solids, crystalline solids, amorphous solids, solids for reconstitution or combinations thereof.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation, or metabolites thereof, in the body of the patient. The administering physician can easily determine optimum dosages, dosing methodologies and repetition rates. Optimum dosages may vary depending on the relative potency of the composition, and can generally be estimated based on arithmetic means, for example based on $EC_{50}$ values found to be effective in in vitro and in vivo animal models, or based on the examples described herein. In general, dosage of the pharmaceutical composition according to the present disclosure is from about 0.01 µg to 100 g/kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 µg to 100 g/kg of body weight, once or more daily, to once every 2 years.

As mentioned above, a person skilled in the art would be able to ascertain, based on, for example, disease severity, the required dosage amount and dosage regime required to attain the desired clinical effect. The following is used as an illustrative example of an intravenous injection, which may be amended as required for other modes of administration. In one example, the method, as disclosed herein, is to be administered to a subject as at least one injection. In one example, more than a single injection may be administered to a patient at any given time. In yet another example, the method as disclosed herein may require that a single injection be administered to the patient more than once within a specified treatment timeframe or regime. In yet another example, the method as disclosed herein may require that more than two or more injections be administered to the patient more than once within a specified treatment timeframe or regime. This means, at according to clinical requirements, the subject may be given an initial treatment in the form of an injection, whereby further treatment may follow at interval of, for example, 3 day, 7 days, weekly, 2 weeks, fortnightly, 1 month, monthly, quarterly, biannually, annually or longer, depending on the treatment designed for the subject. If required, the method disclosed herein may also be used as in combination therapy with other drugs or pharmaceutical compositions.

The term "treat" or "treating" as used herein is intended to refer to providing an pharmaceutically effective amount of a peptide or a respective pharmaceutical composition or medicament thereof, sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

As used herein, the term "pharmaceutically effective amount" or "therapeutically effective amount" is a quantity of a specific substance sufficient to achieve a desired effect in a subject being treated. For instance, this can be the amount necessary to inhibit or suppress progression of a disease, or to decrease a sign or symptom of the disease in the subject. In one embodiment, a therapeutically effective amount is the amount necessary to eliminate a disease. In other words, the pharmaceutically or therapeutically effective amount can be the amount necessary to affect stable disease, or to prevent disease progression, to reverse certain aspects of the disease, or to fully eliminate the disease from the subject. When administered to a subject, a dosage will generally be used that will achieve target tissue concentrations (for example, in the tissue to be treated) that has been shown to achieve a desired in vitro effect.

It is also of note that efficacy of, for example, a single factor treatment, is dependent on the severity of the disease to be treated at the time of treatment onset. For example, based on the clinically known severity score for, for example, GVHD, it was found that the efficacy of the treatment of GVHD with for example, anti-CCL24, was dependent on the severity of the GVHD to be treated. That is to say that if the GVHD was considered to be mild or moderate, the single compound treatment was effective. However, when the severity of the GVHD to be treated was, for example, considered to be severe, a single compound treatment (for example, anti-CCL24 alone) was no longer considered to be effective enough to show, for example, disease remission or a reduce in inflammatory markers. Thus, in such severe cases of immunological diseases, a person skilled in the art may consider the use of more than one compound or pharmaceutical composition as disclosed herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Cell Preparation

Umbilical cord blood mononuclear cells (UCB-MNCs) were isolated from fresh cord blood obtained from Singapore Cord Blood Bank with Ficoll-paque plus (density 1.077 g/l, GE Healthcare) using an established protocol.

Bone marrow (BM)-MSCs were obtained from the BM aspirates of healthy donors (Singapore General Hospital, Department of Hematology). It was cultured in Dulbecco's modified Eagle's Medium (DMEM) supplemented with 20% heat-inactivated Fetal Bovine Serum (FBS) (Gibco) in 37° C., 5% $CO_2$ incubator. Non-adherent cells were removed after 48 hours, and adherent cells were maintained with medium replenishment every 3-4 days until reaching to 90-100% confluence. It was passaged at 1:3 ratios using 0.05% trypsin-EDTA (Gibco) and only cells before 10 passages were used.

Human cryopreserved peripheral blood mononuclear cells (PBMCs) were obtained from healthy donors (Singapore General Hospital, Repository of Department of Hematology).

Immunosuppression of MSCs in Mixed Lymphocyte Reaction (MLR)

MLR served as an in vitro GVHD model and was initiated by co-culturing two HLA-mismatched UCB-MNCs at 15:1 effector/target (E/T) ratios in STEMSPAN medium (Stem Cell Technologies) for 20 hours in 37° C., 5% $CO_2$ incubator. The mixed lymphocytes (ML) were treated with BM-MSCs by co-culture without transwell inserts (i.e. physical direct contact) or with transwell inserts (i.e. indirect bidirectional regulation via the two secretomes) or with BM-MSC-conditional medium. Transwell inserts were placed at 0.5 mm and 0.9 mm above the well bottom, and the 1-day old BM-MSC culture medium was used as conditional medium (1d-CM). Untreated MLR was used as a negative control to set the cell-mediated cytotoxicity baseline of the MLR. The cell-mediated cytotoxicity was measured by lactate dehydrogenase (LDH) cytotoxicity detection kit (Roche). Following the kit instruction, the detection plate was incubated in the dark for 20 minutes at room temperature, and absorbance was measured at 490 nm with 650 nm as reference wavelength using Benchmark Plus microplate spectrophotometer (Bio-Rad).

Detection of MSC-Modulated Cytokines

After 20 hours incubation, supernatant from cultures of ML, BM-MSCs and ML with BM-MSCs was collected and centrifuged at 400 g for 10 mins. The supernatants were analysed with the RAYBIO human cytokine antibody array G series 1000 (containing 120 kinds of cytokines antibody)

according to the manufacturer's instructions. Incubated slides were scanned and analysed by Axon Genepix 6.1.

Identifying Critical Factors in the MSC Secretome by FD

Twelve molecules (six upregulated proteins-OPG, CCL7, CCL8, CCL20, CXCL5 and CXCL6; four antibodies against downregulated proteins-M-CSF, IL-1β, CCL-1 and CCL24; and two control molecules-IL-10 and PGE2 (R&D systems)) were individually titrated. All the proteins and antibodies were purchased from Peprotech. For each molecule, the lowest working concentration that caused the maximum repression of cytotoxicity by MLR was used for further analysis. In order to determine the optimal combination of interested cytokines, the twelve molecules were arranged in a $2^{12}$ fractional FD table (Table 3). There were twelve factors with two levels. Level-1 meant without addition of this interested molecule, level-2 meant addition of this interested molecule with optimal working concentration. Condition-1 without addition of any interested molecules served as negative control; Condition-16 with addition of full panel of interested molecules and MLR laid on MSCs served as positive control respectively.

Based on the maximal extend attenuating cell-mediated cytotoxicity, another $2^7$ factorial FD (Table 4) was derived from Condition-6 in $2^{12}$ fractional FD, which involved IL-10, OPG, CXCL5, CXCL6, CCL20 anti-CCL1 and anti-CCL24.

Similarly, a $2^4$ full FD (Table 5) was further derived from Condition-6 in $2^7$ fractional FD, which involved OPG, CXCL5, anti-CCL1 and anti-CCL24.

Maximum Tolerance Dose (MTD) Study

Two doses of anti-CCL24 antibody and CXCL5 chemokine were administered to 8-10 week-old healthy NSG mice by intravenous (IV) injection at day-1 and day-3 of every week. Injection dose was gradually increased at the beginning of every week (Table 6). The mice body weight and survival were monitored every other day for consecutive 30 days.

Mice

Non-obese diabetic/severe combined immunodeficient-IL2R gamma (NOD.Cg-Prkdc$^{scid}$ Il2rg$^{tm1Wjl}$/SzJ, NSG) mice and MLR/MpJ-Fas$^{lpr}$/J (Fas$^{lpr}$) mice were purchased from Jackson Laboratories. Mice were housed in SingHealth Experimental Medicine Centre and all animal experiments were conducted with the approval of Sing Health Institutional Animal Care and Use Committee (IACUC). For GVHD induction, the age of NSG mice used in all experiments was between 8-10 weeks. For SLE, only female Fas$^{lpr}$ mice were used and the average age of auto-onset of disease was around (14-16)-week-old.

GVHD Induction and Treatment

Moderate and severe xenogeneic GVHD mouse model was induced by injecting 200×10$^6$ cells/kg and 400×10$^6$ cells/kg of human cryopreserved PBMCs to NSG mice respectively by IV injection via tail vein. 240 cGy of irradiation was given to the mice 3-4 hours before the transplantation. NSG mice showed onset of GVHD on 10-12 days post-transplantation (PT). Hence, treatment with 2F cocktail, single format of CXCL5 and anti-CCL24 antibody was given on day-10, day-14, day-17 and day-21 PT. NSG mice injected with dPBS were used as negative control. Mice injected with BM-MSCs (10×10$^6$ cells/kg, single injection on day-10) and CsA (15 mg/kg, Novartis) were used as positive control. Injection volume was normalized to the body weight of the mice. Mouse survival was monitored daily, while clinical scoring was done every three days. 30-40 ul of mouse peripheral blood (PB) was collected from tail vein every 3 days, from day 18 onwards until day 36 post-treatment. Mouse plasma and isolated cells from PB, marrow and spleen were used for luminex assay (Bio-rad) and flow cytometry analysis (CyAN, Beckman coulter). As used herein, the term "PT" stands for post-transplantation of human PBMCs. At day 0, human PBMCs were transplanted into NSG mice to create the referenced GVHD model. The onset of GVHD is took place around day 10 to day 12 PT. Treatment of the sick mice commenced on day 10, day 14, day 17 and day 21 PT, and samples were taken from the mice on day 18, 21, 24, 27, 30, 33 and 36 PT.

Systemic Lupus Erythematosus (SLE) Treatment

MLR/MpJ-Fas$^{lpr}$/J (Fas$^{lpr}$) mice, homozygous for the lymphoproliferation spontaneous mutation, show systemic autoimmunity, massive lymphadenopathy associated with proliferation of aberrant T cells, arthritis, and immune complex glomerulonephrosis. Because of the manifestation similarity between Fas$^{lpr}$ mice and SLE patients, Fas$^{lpr}$ mice can be used as SLE mouse model.

Fas$^{lpr}$ mice automatically showed onset of disease around 16 weeks of age, on average. 10 times of weekly 2FC treatment was given on 16-week-old mice. Fourteen doses of 2F cocktail treatment were weekly given to 16-week-old (16 w) female Fas$^{lpr}$ mice. 5-10×10$^6$ cells/kg of BM-MSCs and dPBS were used as positive and negative control. The efficacy of 2F cocktail in SLE was evaluated by the improvement of mice survival, kidney function and reduction of autoantibodies secretion. Mice plasma and urine were collected on 14 w-, 18 w-, 22 w-, 26 w- and 30 w-old mice. Autoantibodies secretion was measured by anti-dsDNA Ig's (A+G+M) ELISA kit (alpha diagnostic international). Kidney function was assessed by urine albumin-to-creatinine ratio (ACR). Mouse albumin ELISA kit was from abcam, creatinine colorimetric assay kit was from Cayman chemical. Autoantibody and ACR detections followed the standard protocol provided by the manufacturer.

Clinical and Histological Scoring

Mouse survival was monitored daily and clinical score (for GVHD) was monitored every three days. The assessment of clinical GVHD index was based on five parameters: weight loss, posture, activity, fur texture and skin integrity, giving a maximum index of 10. At experimental end-point on day 30 post-treatment, histological evaluation was performed on representative mice on the following tissues: skin, small intestine and kidney with Haematoxylin and Eosin (H&E) stain. Key histological parameters assessed were different for each tissue type according to accepted published criteria for acute GVHD in the different organ systems. Basal vacuolar change, spongiosis and lymphocytic satelittosis were graded for skin; crypt apoptosis, lymphocytic inflammation and intraepithelial lymphocytosis was graded for small intestine; and interstitial inflammation, tubulitis and arterial changes were graded for kidney. All parameters were graded with 4 tiers (none, mild, moderate and severe) and given a score of 0-3, giving a maximum index of 27 (Table 7). The slides were scored in blinded fashion by a single observer.

ELISA and Luminex Assay

Anti-dsDNA antibody concentration in Fas$^{lpr}$ mice plasma was determined using Mouse Anti-dsDNA Antibodies Total Ig ELISA kit (Alpha Diagnostic). 150-200 ul of mouse peripheral blood was harvested by cheek bleeding every 4 weeks from mice aged 14-week-old onwards until 26-weeks old. 4,000 times diluted Fas$^{lpr}$ mice plasma samples were incubated in the 96-well-plate for 1 hour. Then anti-Mouse Ig HRP conjugate was added and incubated for 30 minutes. TMB substrate was added for 15 minutes and finally the reaction was halted with stop solution. Five complete wash steps were required between each incubation step. The plate was read on Bio Rad microplate spectrometer at 450 nm.

Using luminex technology, multiple analytes can be detected simultaneously in the same sample. Circulating human source cytokines/chemokines were measured using a Bio-plex Pro Human Cytokine 17-plex kit (Bio-rad). It included analytes of G-CSF, GM-CSF, IFN-γ, IL-1β, IL-2, IL-4, IL-5, IL-6, IL-7, IL-8, IL-10, IL-12, IL-13, IL-17A, MCP-1, MIP-1β and TNF-α in the analysis. Following the standard protocol, 16 times diluted plasma samples were incubated with magnetic beads for 2 hours, the with detection antibodies for 1 hour and finally with streptavidin-PE for 10 minutes at room temperature. Three complete wash steps were required between each incubation step. The plate was read on Milliplex Analyzer (Millipore) with Luminex xPONENT software.

Albumin and Creatinine Detection

Kidney function damage of $Fas^{lpr}$ mice was evaluated by measuring the changes of urinary albumin to creatinine ratio (ACR). 20-50 ul of urine was harvested by bladder massage every 4 weeks from 14-week-old onwards until 26-week-old. Albumin concentration was detected by Mouse Albumin ELISA kit (Abcam). Following the standard protocol, 100,000 times diluted $Fas^{lpr}$ mice urine samples were incubated in the primary antibody coated 96-well-plate for 2 hours, biotinylated antibody for 1 hour, streptavidin-peroxidase for 30 minutes, chromogen for 15 minutes and finally with the stop solution. Five times complete wash were required between each incubation step. The plate was read on Bio Rad microplate spectrometer at 450 nm.

Creatinine level was detected by Jaffe's reaction using Creatinine Colorimetric Assay kit (Cayman). Following the standard protocol, 20 times diluted $Fas^{lpr}$ mice urine samples and alkaline picrate solution was added to the 96-well-plate. Plate was incubated in room temperature for 10 minutes and read on Bio Rad microplate spectrometer at 490 nm.

Flow Cytometry Analysis

Cells isolated from NSG mouse peripheral blood (PB) harvested from tail vein, BM and spleen were subjected to flow cytometric analysis using CyAN (Beckman coulter) with Summit software. For cell surface markers, the following antibodies were used: hCD45-PE-Cy7 (H130), hCD3-ECD (UCHT1) (Beckman coulter), hCD4-PerCP-Cy5.5 (SK3), hCD8-APC (RPA-T8), hCD56-FITC (NCAM16.2), hCD25-PE-Cy7 (M-A251), hFoxP3-PE (259D/C7), hIFN-γ-BV421 (4S.B3), hIL-17A-AF647 (N49-653), hCD68-BV421 (Y1/82A), hCD19-FITC (H1B19), hCD34-BV421 (581); and mCD45-AF700 (30-F11), mCD45-FITC (30F11) (Miltenyi Biotec), mCD11b-APC (M1/70), Ly6G-PC7 (1A8).

For intracellular staining, cells were stimulated with 50 ng/ml of PMA (Sigma-Aldrich) and 1 µg/ml of ionomycin (Sigma-Aldrich) overnight (12-16 hours) at 37° C. 3 µg/ml of brefeldin A (Sigma-Aldrich) was added one hour after incubation. Activated cells were further fixed and permeabilized by Fixation/Permeabilization solution (Miltenyi Biotec) for 45 minutes at 2-8° C. Then the cells were washed with permeabilization buffer two times and stained with intracellular antibodies for 30 minutes at 2-8° C. in the dark.

For cells isolated from $Fas^{lpr}$ mouse spleen, mesenteric lymph node and thymus, the following antibodies were used: mCD45-PE (30F11), mCD19-FITC (1D3), mCD3-PC7 (17A2), mCD4-APC-CY7 (GK1.5), mCD8a-V500 (53-6.7), mCD11c-Percp-cy5.5 (HL3), mCD49b-APC (DX5), mLy6G-PC-Cy7 (1A8), mCD11b-APC (M1/70) and mCD1d-BB515 (1131). All antibodies were purchased from BD Biosciences unless otherwise specified.

Statistical Analysis

Factorial design experiments were analysed using ANOVA. Student paired t-test was used to do the significance analysis. $p<0.05$ was considered statistically significant. The overall trend difference was compared by means of generalized estimating equation (GEE) model.

Mice

Seven to eight-week-old DBA/1J, DBA/2J mice (Jackson laboratory, USA) and female C57BL/6 (B6) mice (InVivos, Singapore) were maintained in pathogen-free conditions in the animal research facility of Sing Health Experimental Medicine Centre. All mouse experiments were carried out in strict accordance with the Guide of Sing Health Institutional Animal Care and Use Committee.

Diffuse Alveolar Haemorrhage (DAH) Induction and Treatment

To induce DAH, 0.5 mL of pristane was administered intraperitoneally to 7 to 8-week-old B6 mice. Healthy mice were left untouched. 50 ng/ml of CXCL5 was given to pristane-challenged mice on day 1, day 4, day 7 and day 11 post-induction. B6 mice treated with dPBS, BM-MSCs (5-10×106 cells/kg, single injection on day 1) and Prednisolone (Pred) (1 mg/kg/day during day 1 to day 7, 0.5 mg/kg/day during day 8 to day 13) were used as positive and standard controls. Injection volume was normalized to the body weight of the mice. Mice were sacrificed and examined 14 days later. In some experiments, bronchoalveolar lavage fluid (BALF) was collected by intratracheal perfusion. After euthanizing the mice, a small incision was made in the trachea and the alveolar spaces were lavaged with 1 ml of dPBS. Cell and supernatant isolated from bronchoalveolar lavage fluid was used for flow cytometry analysis and Luminex assay.

Collagen-Induced Arthritis (CIA) and Treatment

Arthritis was induced in 8 to 10 week-old DBA/1J mice following immunization with collagen and complete Freund's adjuvant (CFA) (Chondrex, USA). Complete Freund's adjuvant was prepared by mixing heat-inactivated mycobacterial strain H37RA in incomplete Freund's adjuvant (4 mg/mi). Lyophilized bovine type II collagen (Chondrex, USA) was dissolved overnight in acetic acid at 2 mg/ml. Complete Freund's adjuvant and collagen were mixed at a ratio of 1:1 to form an emulsion. 100 µg of collagen, which was then injected intradermally at the base of the tail. Mice were scored for arthritis weekly from day 30 after immunization. 50 ng/ml of CXCL5 was given twice/week to CIA mice for 3 consecutive weeks, to around day 40 to 50 post-induction, when mice started to show the arthritis symptoms. Mice treated with dPBS, bone marrow-derived mesenchymal stem cells (BM-MSCs; 5-10×10$^6$ cells/kg, single injection) and Prednisolone (Pred) (1 mg/kg/day for first 10 days, 0.5 mg/kg/day for the second 10 days) were used as positive and standard controls, respectively. Injection volume was normalized to the body weight of the mice. Mice were monitored for another 3 weeks post-treatment and then sacrificed for further analysis. Peripheral blood (PB) was collected on day 15 and day 42 post-treatment. Isolated blood cells and plasma were used for flow cytometry analysis and Luminex assay.

Bleomycin-Induced Scleroderma and Treatment

Skin fibrosis was induced in 6 to 8-week-old DBA/2J mice by subcutaneous injection of bleomycin (0.5 mg/mi) into defined areas of 1 cm$^2$ on the lower back every other day, for 21 days. After a 3-week bleomycin challenge, another 3-week treatment was followed. 50 ng/ml of CXCL5 was given twice/week for 3 consecutive weeks. Mice treated with dPBS, bone marrow-derived mesenchymal stem cells (BM-MSCs; 5-10×10$_6$ cells/kg, single injection) and Prednisolone (Pred) (1 mg/kg/day for first 10 days, 0.5 mg/kg/day for the second 10 days) were used as positive and standard controls. Mice were sacrificed on day 21 post-treatment and the injected skin and peripheral blood were processed for further analysis.

Diffuse Alveolar Haemorrhage (DAH) Clinical and Histological Scoring

Mice body weight and survival were monitored daily. The prevalence of lung bleeding was evaluated on bronchoalveolar lavage fluid by red blood cell (RBC) count. For healthy mice or mice without bleeding, the bronchoalveolar lavage fluid red blood cell count ranged from 0 to 0.05×10$^9$ cells/lung with clear appearance. If there was mild bleeding, the red blood cell count went up to 0.05 to 0.4×10$^9$ cells/lung with rare red dot-like appearance; if there was moderate bleeding, the red blood count went up to 0.4 to 0.6×10$^9$ cells/lung with increased red dot-like appearance; if there was severe bleeding, the red blood cell count even further went up more than 0.6×10$^9$ cells/lung with completely deep red appearance. At day 14, histological evaluation was performed on mouse lung with Hematoxylin and Eosin (H&E) staining.

Collagen-Induced Arthritis (CIA) Clinical and Histological Scoring

Clinical scoring of CIA was performed as follows: 0=no swelling or redness of paws or digits; 1=swelling and redness in one to two digits; 2=swelling and redness over ankle or three or more digits or midfoot; 3=swelling and redness over ankle and midfoot or digits and midfoot; 4=swelling and redness over entire foot or ankylosis as showed in Table 8 below. The disease activity index (DAI) was the sum score of four paws.

TABLE 8

Clinical scoring of CIA

| Paw score | Clinical observations |
|---|---|
| 0 | Normal paw. |
| 1 | One toe inflamed and swollen. |
| 2 | More than one toe, but not entire paw, inflamed and swollen, or mild swelling of entire paw. |
| 3 | Entire paw inflamed and swollen. |
| 4 | Very inflamed and swollen paw or ankylosed paw. If the paw is ankylosed, the mouse cannot grip the wire top of the cage. |

Mouse paws were used for histology scoring. The paraffin-embedded tissue was sectioned in an axis longitudinal to the tibia. Three sections from the centre of each paw were stained with hematoxylin & eosin (H&E), and scored by two independent blinded observers. Inflammatory infiltrate, synovitis (synovial hyperplasia), cartilage destruction and bone involvement were each scored on a scale of 0 to 3. 0=no change, 1=mild, 2=moderate and 3=severe.

Scleroderma Histological Scoring

Lesioned skin areas were excised, fixed in 10% formalin, and embedded in paraffin. Sections (5 μm thick) were stained with hematoxylin & eosin (H&E). The dermal thickness was analyzed at 100-fold magnification by measuring the distance between the epidermal-dermal junction and the dermal-subcutaneous fat junction at four sites from the lesioned skin of each mouse. Dermal leukocyte infiltration was counted on randomly-taken photos with High Power Field (HPF) (400×). Five photos were taken for each mouse. The average cell number of these five photos was used for counting the leukocyte infiltration. Two independent examiners performed the evaluation.

Luminex Assay

Following the manufacturer's protocol, the levels of cytokines/chemokines in mouse peripheral blood (PB) and bronchoalveolar lavage fluid (BALF) were measured using a Bio-plex Pro Mouse Cytokine 23-plex kit (Bio-rad). The immunoglobulin levels in peripheral blood and bronchoalveolar lavage fluid were measured with Mouse Immunoglobulin Isotyping Magnetic Bead Panel kit (Millipore). The cytokine plates were read on the Milliplex Analyzer (Millipore) with Luminex xPONENT software.

Flow Cytometry Analysis

Cells isolated from mice peripheral blood and/or bronchoalveolar lavage fluid were subjected to flow cytometric analysis using CyAN (Beckman coulter) with Summit software. The following flow antibody panels were used for mouse cells phenotyping: (1) CD45-PE (30F11) (Biolegend), CD19-BB515 (1D3), CD3-PE-Cy7 (17A2) (Biolegend), CD4-APC-Cy7 (GK1.5), CD8-V510 (53-6.7) (Biolegend), CD49b-APC (DX5); (2) CD45-PE (30F11) (Biolegend), Ly6G-PE-Cy7 (1A8), CD11b-APC (M1/70), Siglec F-APC-Cy7 (E50-2440); (3) CD45-PE (30F11) (Biolegend), CD25-BV421 (PC61), FoxP3-PE-CF594 (MF23), IFN-γ-PE-Cy7 (XMG1.2), IL-17A-BV510 (TC11-18H10.1) (Biolegend). All antibodies were purchased from BD Biosciences unless otherwise specified.

For intracellular staining, cells were stimulated with 50 ng/ml of phorbol myristate acetate (PMA) (Sigma-Aldrich), 1 μg/ml of ionomycin (Sigma-Aldrich) and blocked with 1× brefeldin-A (BD Bioscience) at 37° C. After overnight incubation, activated cells were fixed and permeabilized with fixation/permeabilization solution (Miltenyi Biotec) for 30 to 45 minutes and stained with intracellular antibodies for 30 minutes for flow cytometry analysis.

Statistical Analysis

Student T-test was applied. $p<0.05$ was considered statistically significant. For multiple comparisons, the p-value was adjusted with Bonferroni's correction. The generalized estimating equation (GEE) model was used in measurement of biological trends.

Results

MSCs Modulate Allogenic Immune Reactions Through Paracrine Factors

Conditioned medium from a 24 h, pure BM-MSC culture was able to reduce cell-mediated cytotoxicity to 83.9±8.1% in in an in vitro GVHD model-MLR (FIG. 1). Cytotoxicity was further reduced when the BM-MSC was co-cultured with the MLs in transwell inserts; suggesting that the BM-MSC secretome might be partially regulated by the MLs. The degree of reduction in cytotoxicity is influenced by the physical distance between the two cell types. It was reduced to 62.2±3.2% at 0.9 mm and 47.5±6.5% at 0.5 mm. The maximum reduction occurred when the cells were in physical direct contact (27.9±3.6%). These results indicate that the immunosuppressive effect of MSCs is partly or wholly paracrine in nature and is negatively correlated to the separation between the MLs and MSCs.

MSC—Secreted Paracrine Factors were Elucidated by Cytokine Antibody Array

Figure 2:
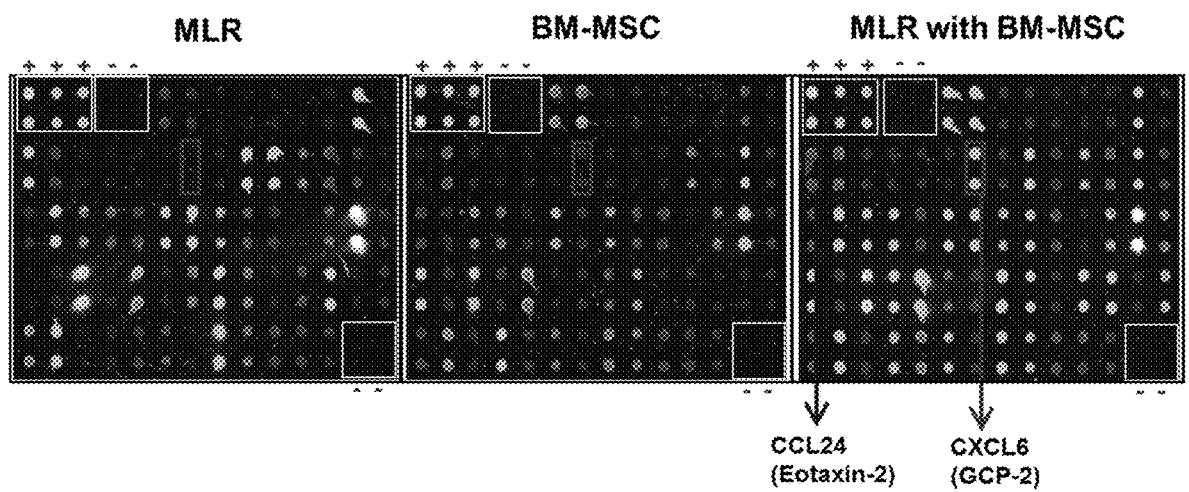
FIG. 2 shows images of a cytokine antibody array assay, whereby supernatant from cultures of MLR, BM-MSCs and MLR with BM-MSCs was collected and applied on Raybio RAYBIO human cytokine antibody array G series 1000 (containing 120 kinds of cytokines antibody) according to the manufacturer's instructions. Incubated slides were scanned and analysed by Axon Genepix 6.1. Positive and negative control wells were marked by white boxes, while wells with more than 3-fold change in protein expression level were marked by grey box (upregulated) and black box (downregulated).

Factors that presented in the BM-MSC/ML co-culture and in single cultures were identified using a cytokine antibody array (FIG. 2). With a selection criterion of at least a three-fold change in cytokine expression levels, five upregulated proteins were identified, namely CCL20, CCL8, CXCL5, OPG and CXCL6, as well as three downregulated proteins, IL-1β, CCL1 and CCL24 (Table 2). In order to ascertain that relevant factors were not missed by the arbitrary three-fold cut-off, 2 factors with a fold-change between 2 and 3 were randomly chosen (CCL7 and M-CSF) and added to the subsequent validation experiments.

Optimal Working Concentration of Immunosuppression Relevant Factors was Determined For further studies to identify critical factors amongst the 10 candidates, the working concentration of each upregulated factors and antibody against downregulated factors had to be established. Dose response curves of cytotoxicity repression in MLR were generated and the lowest concentration to general maximum repression was selected as the working concentration (FIG. 3). PGE2 and IL-10 were reported to be effective in modulating cell proliferation and cytotoxicity on CD4+ helper T cells, CD8$^+$ cytotoxic T cells and nature killer cells; hence they were included as control molecules. The optimal in vitro working concentrations were: 50 ng/ml of CCL20, 10 ng/ml of CXCL6, 50 ng/ml of CCL7, 10 ng/ml of CCL8, 10 ng/ml of OPG, 10 ng/ml of IL-10, 50 ng/ml of CXCL5, 2 μM of PGE2 and 2 μg/ml of anti-CCL1, 1 μg/ml of anti-IL-1β, 1 μg/ml of anti-M-CSF, 2 μg/ml of anti-CCL24 antibody respectively Among these twelve factors, anti-CCL1 antibody affected the highest level of cytotoxicity repression (42.7±4.1%). But it was still significantly higher than the 22.7±2.8% from MLR with direct contact between BM-MSC and ML ($p<0.001$). This indicated that inhibition or promotion of any single factor from the list could not fully mimic the immunosuppressive effect of MSCs. This means that, while single factors were shown to be effective, they are not considered to be as effective as the combinations, when comparing the resulting immunosuppressive effect. Having said that, it is also noted, as mentioned previously in this application, that the severity of the disease to be treated has an effect on the efficacy of the treatment chosen. Hence, without being bound by theory, it is thought that MSC modulated immunosuppression through a combination of factors, of which the optimal combinations were identified and validated using by factorial design.

Optimal Combination of Immunosuppression Relevant Factors were Determined by FD

Figure 4:
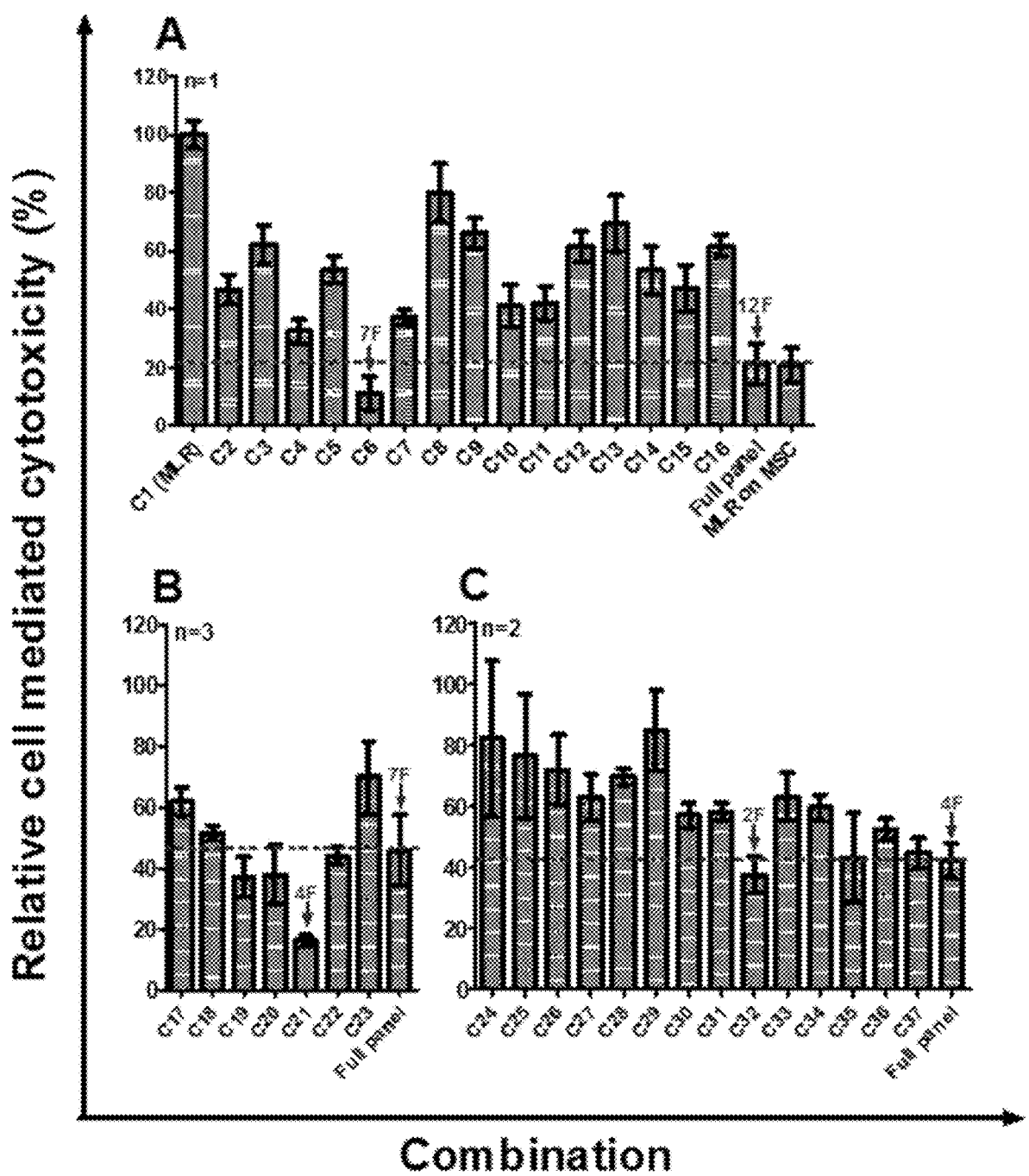
FIG. 4 shows column graphs depicting data of the efficacy of the combination of determined factors used in optimal soluble factor cocktails, which was determined by serial factorial design experiments (FDs). (A) The full panel of 12 factors were screened in a $2^{12}$ factional FD (n=1). Condition-6 (C6) containing 7 factors was more effective than full panel control and MSC physical contact in repressing cell mediated cytotoxicity ($p<0.05$). (B) A second $2^7$ fractional FD identified C6 with 4 factors was even more effective than full panel control in repressing cell mediated cytotoxicity (n=3, p<0.05). (C) These 4 factors were further tested in a $2^4$ full FD (n=2). C10 containing two factors-CXCL5 and anti-CCL24 antibody exhibited equivalent effect in repressing cell mediated cytotoxicity as compared to 4 factor full panel control. Results were expressed as mean±S.E. when n≥2. Results were expressed as mean±S.D. when n<2.

Factorial design is an efficient method for determining the effects of multiple variables on a single response. It can reduce the number of experiments by studying multiple factors simultaneously. Here, a $2^{12}$ fractional FD was used to determine the optimal combination and relative importance of 12 factors of interest (Table 3). The relative cell-mediated cytotoxicity of $2^{12}$ fractional FD was showed in FIG. 4A. The optimal combination was C6, which comprised seven factors: CCL20, CXCL6, OPG, IL-10 and CXCL5 protein as well as anti-CCL1 and anti-CCL24 antibodies, which reduced the relative cell-mediated cytotoxicity to 11.1±5.8%. It was even more effective than the full panel control (21.1±6.9%) and the BM-MSC co-culture with direct contact (20.7±6.0%) ($p<0.05$).

From variance analysis, the relative importance of these twelve factors in immune suppression was determined. anti-CCL24 ($F=11.09$)>IL-10 ($F=4.38$)>OPG ($F=2.92$)>CXCL5 ($F=2.62$)>anti-IL-1β ($F=2.52$)>CXCL6 ($F=2.14$)>anti-M-CSF ($F=2.09$)>anti-CCL1 ($F=1.89$)>CCL20 ($F=0.48$)>PGE2 ($F=0.12$)>CCL7 ($F=0.10$)>CCL8 ($F=0.09$) ($p<0.05$, $F_{stastic\ cut-off}=10.10$). There was significant impact on immunosuppression when F value was more than 10.10. Hence, only anti-CCL24 antibody significantly affected cell mediated cytotoxicity as compared to others.

In addition, anti-M-CSF ($7^{th}$) and CCL7 ($11^{th}$) were not included in C21 and had F statistics that were below the cut-off of 10.10. This indicated that the selection of candidate factors was sufficiently stringent.

In order to eliminate unnecessary factors in C6 ($2^{12}$ FD), the seven factors were subjected to another round of fractional FD experiment ($2^7$) (Table 4). The relative cell-mediated cytotoxicity of $2^7$ fractional FD was shown in FIG. 4B. The optimal combination was C21, which consisted of four factors: CXCL5, OPG protein and anti-CCL1, anti-CCL24 antibodies. It could reduce the relative cell-mediated cytotoxicity to 16.1±2.1% (n=3), which is superior to 45.8±14.3% in the full panel control.

These four factors were further analysed in a full FD (Table 5). The relative cell-mediated cytotoxicity was shown in FIG. 4C. The optimal combination was C32, which consisted of only two factors: CXCL5 and anti-CCL24 antibody. It could suppress the relative cell-mediated cytotoxicity to 37.7±6.2%, which is comparable to 44.7±4.9% in the full panel control C38. Thus, through serial FDs, a two factor (2F)-cocktail comprising CXCL5 and anti-CCL24 antibody was finally established.

Safe Administration Dose, Side Effect on Neutrophil and Red Blood Cell (RBC) Count as Well as Toxicity Test Before validating the immunosuppressive effect of the 2F cocktail in mice, the safety dose of each factor needs to be established.

Figure 5:
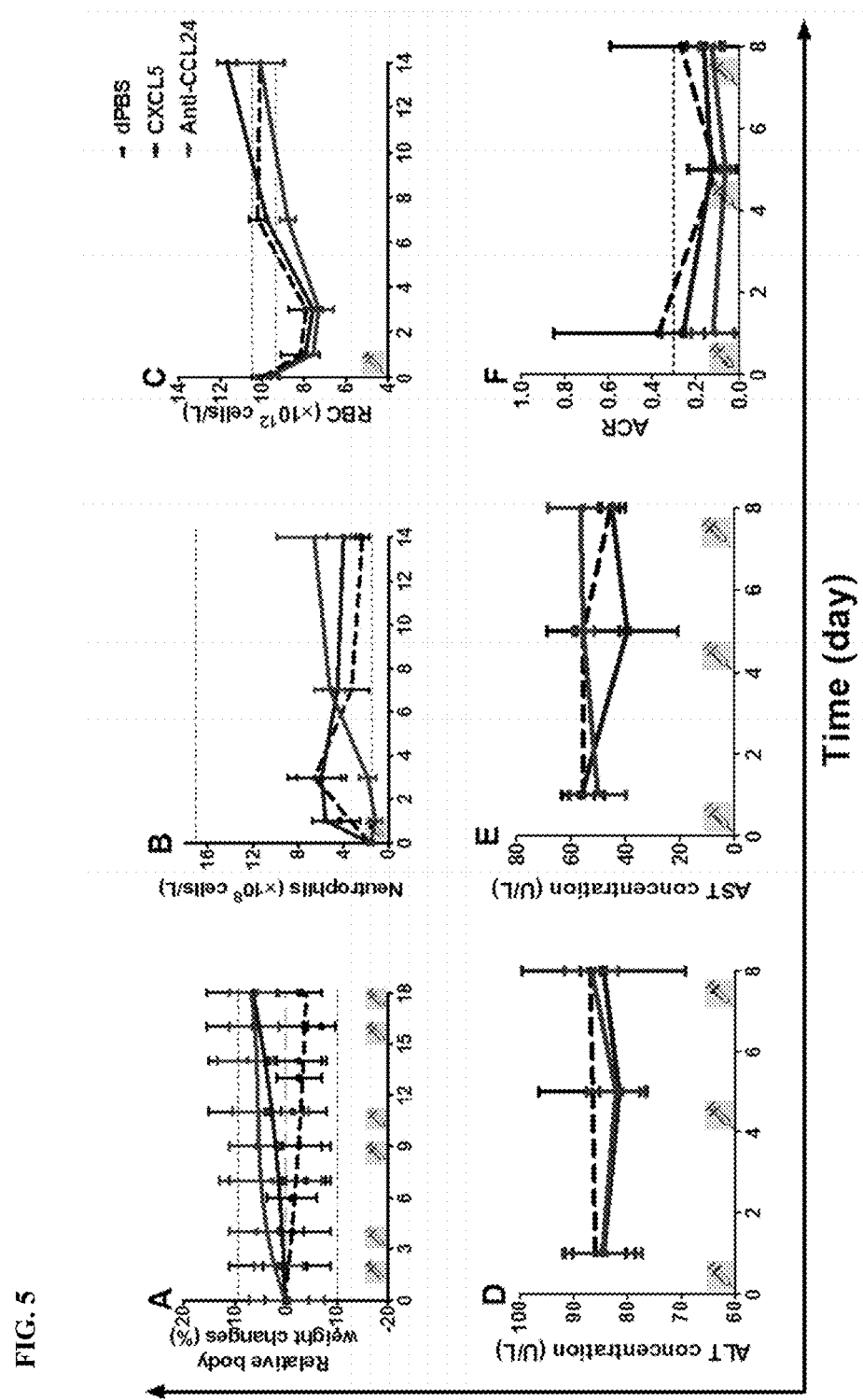
FIG. 5 shows line graphs depicting the relative weight change, side effect on neutrophil and red blood cell count and toxicity in liver and kidney when mice were treated with CXCL5 and anti-CCL24 antibody. (A) Body weight changes. NSG mice were treated with CXCL5 and anti-CCL24 antibody twice weekly with gradually increasing dose (3 mice were used in each group). (B & C) Side effect on neutrophil and red blood cell count. ICR mice treated with dPBS, CXCL5 and anti-CCL24 antibody were bled and a blood count was performed on day 1, day 3, day 7 and day 14 post-treatment (4 male mice were used for each group). (D & E & F) Liver and kidney toxicity. ICR mice were treated with dPBS, CXCL5 and anti-CCL24 antibody on day 0, day 4 and day 7. Mice peripheral blood by cheek bleeding and urine were harvested on day 1, day 5 and day 8. Alanine transaminase (ALT) and aspartate transaminase (AST or SGOT) concentration in plasma were determined by ALT and AST activity assay kit. Both alanine transaminase and aspartate transaminase are enzyme associated with the liver and are therefore used as clinical marker for liver health. Albumin creatinine ratio (ACR) in urine was determined by Mouse Albumin ELISA kit and Jaffe's reaction using Creatinine Colorimetric Assay kit (3 female ICR mice were used for each group).

CXCL5 and anti-CCL24 antibody were administered to 8 to 10 week old healthy NSG mice (Table 6). The survival and body weight changes were monitored for 18 days (FIG. 5A). The body weight stably maintained when mice were treated with CXCL5 and anti-CCL24 antibody, which was higher than mice treated with dPBS. All the mice survived to the end of the experiment (18 days). Mice injected with either of the factors (at all doses) did not show abnormal clinical symptoms during the experiment. Overall, administration of the 6 μg/ml of anti-CCL24 and 200 ng/ml of CXCL5 twice per week was well-tolerated and was deemed safe to use for subsequent in vivo studies. Overall, administration of the 6 μg/ml of anti-CCL24 and 200 ng/ml of CXCL5 twice per week was well-tolerated and was deemed safe to use for subsequent in vivo studies.

The side effect on neutrophils and RBC count were evaluated in male ICR mice. Administration of CXCL5 or anti-CCL24 antibody did not alter neutrophil and RBC count, it still kept them in normal range and there was no significant difference between mice treated with single factor and dPBS (FIGS. 5B and 5C).

The toxicity of these two factors was also tested in female ICR mice. Administration of these two factors did not show any toxicity to mice liver and kidney. There was no significant difference in ALT, AST expression level in liver and ACR in kidney between mice treated with single factor and dPBS (FIGS. 5D, 5E and 5F).

2F Cocktail Treatment Exhibited Tremendous Immunosuppressive Capacity in Severe GVHD In order to validate the efficacy of the 2F cocktail in immunosuppression, four doses were administered to mice after the onset of GVHD on Day-10, Day-14, Day-17 and Day-21 post-transplant (PT).

Figure 6:
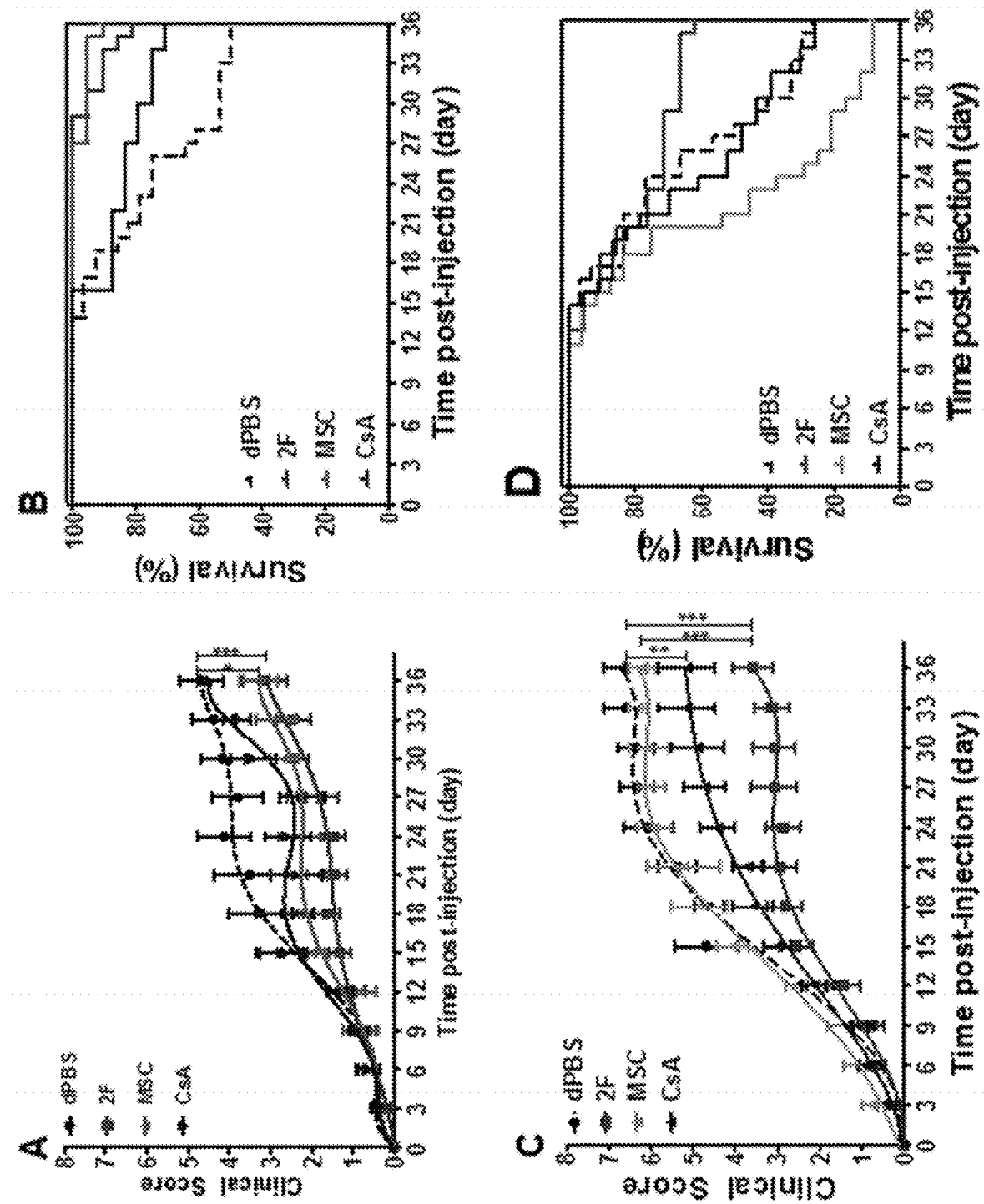
FIG. 6 shows line graphs depicting data showing that the 2F cocktail treatment (anti-CCL24 antibody and CXCL5) ameliorated GVHD symptoms and prolonged survival. (A) Clinical scores and (B) Survival curve with mice in moderate GVHD (n=5; $N_{dPBS}$=28 mice, $N_{2F}$=21 mice, $N_{MSC}$=21 mice, $N_{CsA}$=23 mice). (C) Clinical scores and (D) Survival curve with mice in severe GVHD model (n=5; $N_{dPBS}$=30 mice, $N_{2F}$=21 mice, $N_{MSC}$=24 mice, $N_{CsA}$=23 mice). Results were expressed as mean±SE. The overall trend difference between different treatments was compared by means of generalized estimating equation (GEE) model (*p<0.05; p<0.005; *p<0.001).

In moderate GVHD, the 2F cocktail improved 36-day survival from 61.1% with moderate symptoms to 88.9% with mild symptoms (dPBS: 11/18 mice; 2F: 16/18 mice, ($p<0.05$)). This was comparable to BM-MSCs (88.9%, 16/18 mice) and CsA (83.3%, 14/17 mice), a conventional clinical immunosuppressant (FIGS. 6A and 6B, Table 7). However, in severe GVHD, the 2F cocktail improved 36-day survival from 19.0% with severe symptoms to 61.9% with mild symptoms (dPBS: 4/21 mice; 2F: 13/21 mice, (p<0.01)). This was significantly better than BM-MSC (8.3%, 2/24 mice (p<0.001)) and CsA (26.1%, 6/23 mice (p<0.05)) (FIGS. 6C and 6D).

Figure 7:
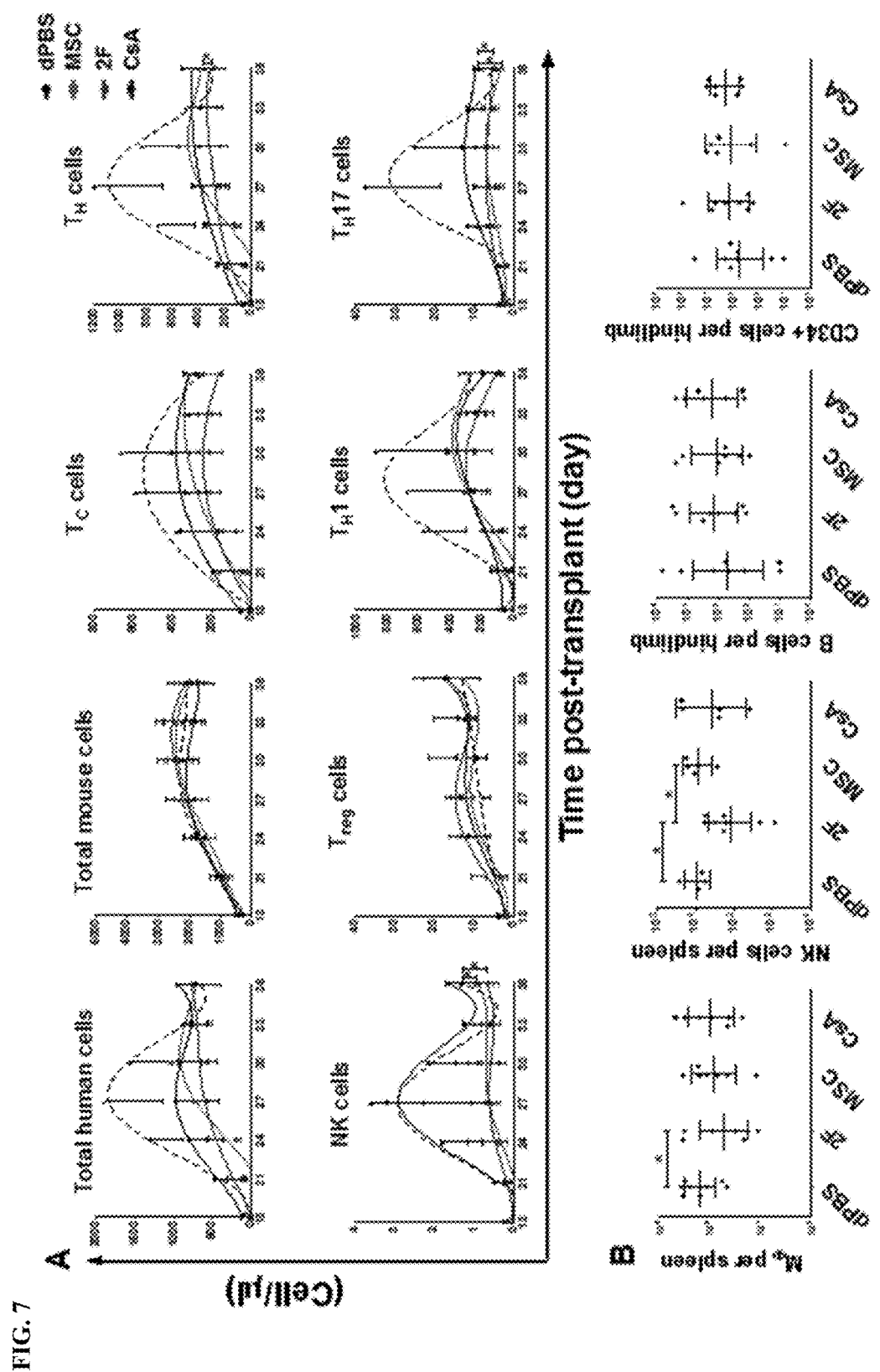
FIG. 7 shows line and scatter plots of data showing that the 2F cocktail (anti-CCL24 antibody and CXCL5) suppresses the proliferation and differentiation of effector cells, but not affect HSCs reconstitution. (A) Effector cell population changes in peripheral blood are shown as line graphs. 30-40μl of mouse peripheral blood was harvested from the tail every 3 days from Day-18 onwards until Day-36 PT. Effector cell population changes was monitored by flow cytometry. Results were expressed as mean±S.E. (n=5). (B) Cell population changes in spleen and bone marrow at Day-40 PT shown as scatter plots. Results were expressed as mean with 95% CI.
Figure 8:
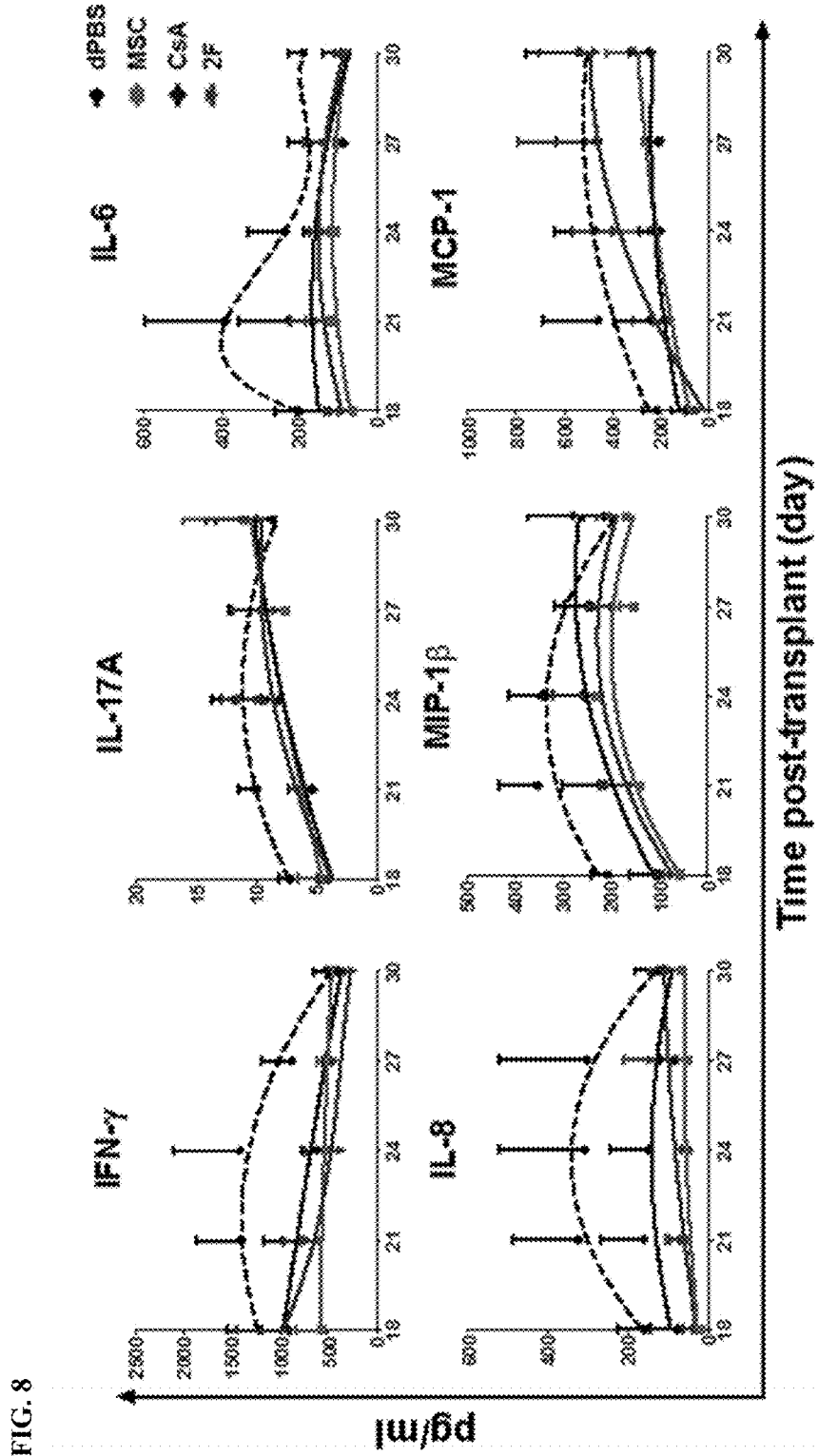
FIG. 8 shows line graphs depicting data showing that the 2F cocktail (anti-CCL24 antibody and CXCL5) was superior to MSCs and CsA in suppression of human pro-inflammatory cytokines. Plasma isolated from mouse peripheral blood was used for protein assay by Luminex with a 17-plex human cytokine kit. Results were expressed as mean±SD. The profile of different treatments was compared by means of a generalized estimating equation (GEE) model (*, p<0.0167; **, p<0.0033, for multiple comparisons).

The 2F Cocktail Ameliorated GVHD Through Suppressing the Proliferation and Differentiation of Multiple Effector Cells In moderate GVHD, the 2F cocktail treatment reduced the proliferation and differentiation of helper T cells (especially for Th1 and Th17 cells) and NK cells in the circulation, and macrophages in the spleen, but did not reduce CTLs and B cells and increase regulatory T cells (Tregs) (FIG. 7). Concurrently, it also reduced pro-inflammatory cytokine IFN-γ, IL-6, IL-8, IL-17A, MIP-1β and MCP-1 secretion in the circulation (FIG. 8). These 2F-elicited changes did not affect the reconstitution of $CD34^+$ human hematopoietic stem/progenitor cells (HSCs/HPCs) in the bone marrow.

Anti-CCL24 and CXCL5 Affect Immunosuppression in a Concerted Manner

Figure 9:
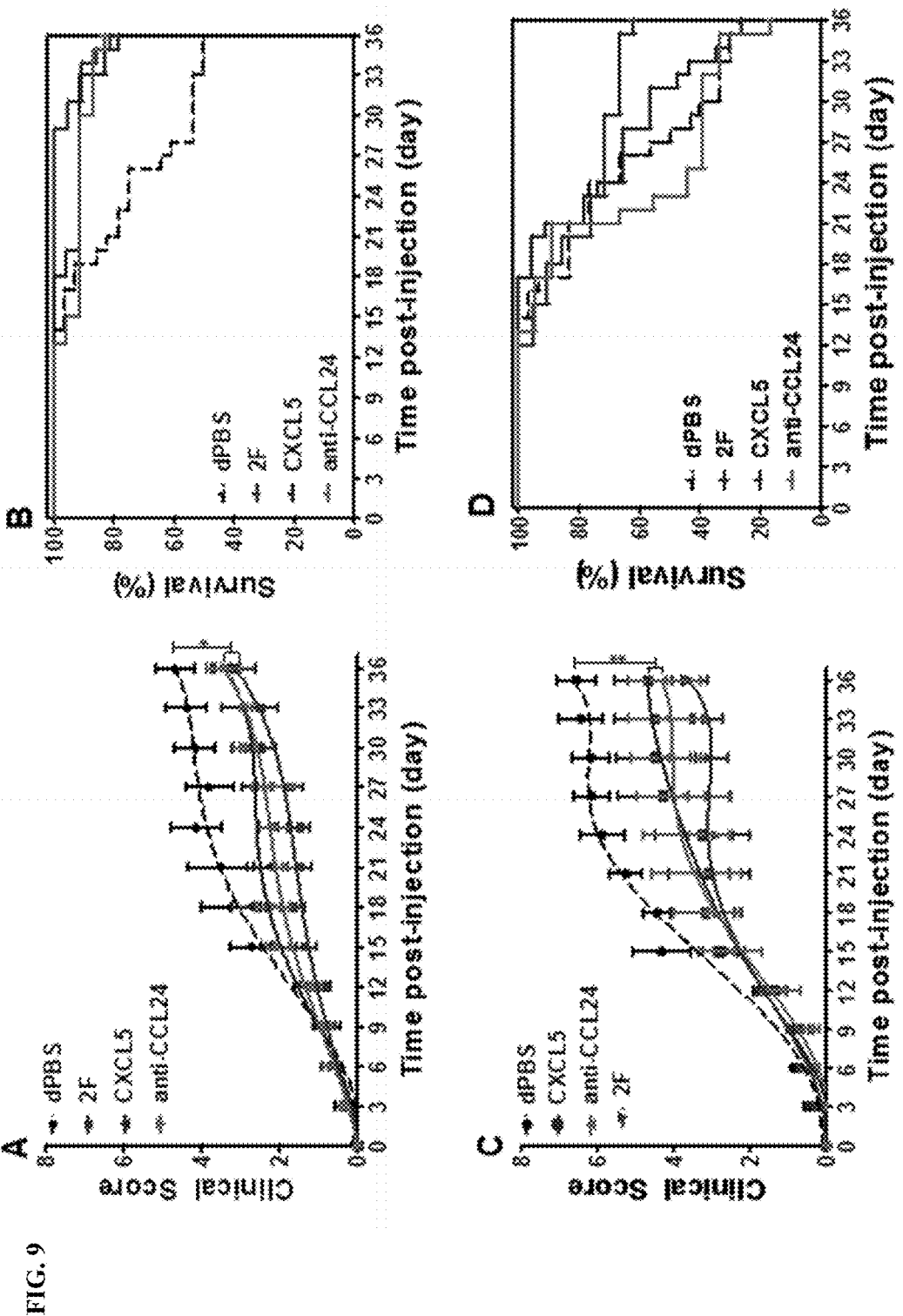
FIG. 9 shows line graphs and Kaplan-Meier curves depicting data that showing a Synergistic effect observed in severe GVHD model. (A) Clinical scores and (B) Kaplan-Meier survival curve of mice with moderate GVHD (n=5; $N_{dPBS}$=28 mice, $N_{2F}$=21 mice, $N_{CXCL5}$=23 mice, $N_{anti-CCL24}$=23 mice). (C) Clinical scores and (D) Kaplan-Meier survival curve of mice with severe GVHD (n=5; $N_{dPBS}$=30 mice, $N_{2F}$=21 mice, $N_{CXCL5}$=23 mice, $N_{anti-CCL24}$=18 mice). Results were expressed as mean±SE. The overall trend difference between different treatments was compared by means of generalized estimating equation (GEE) model (*p<0.05; p<0.005; p<0.001).
Figure 10:
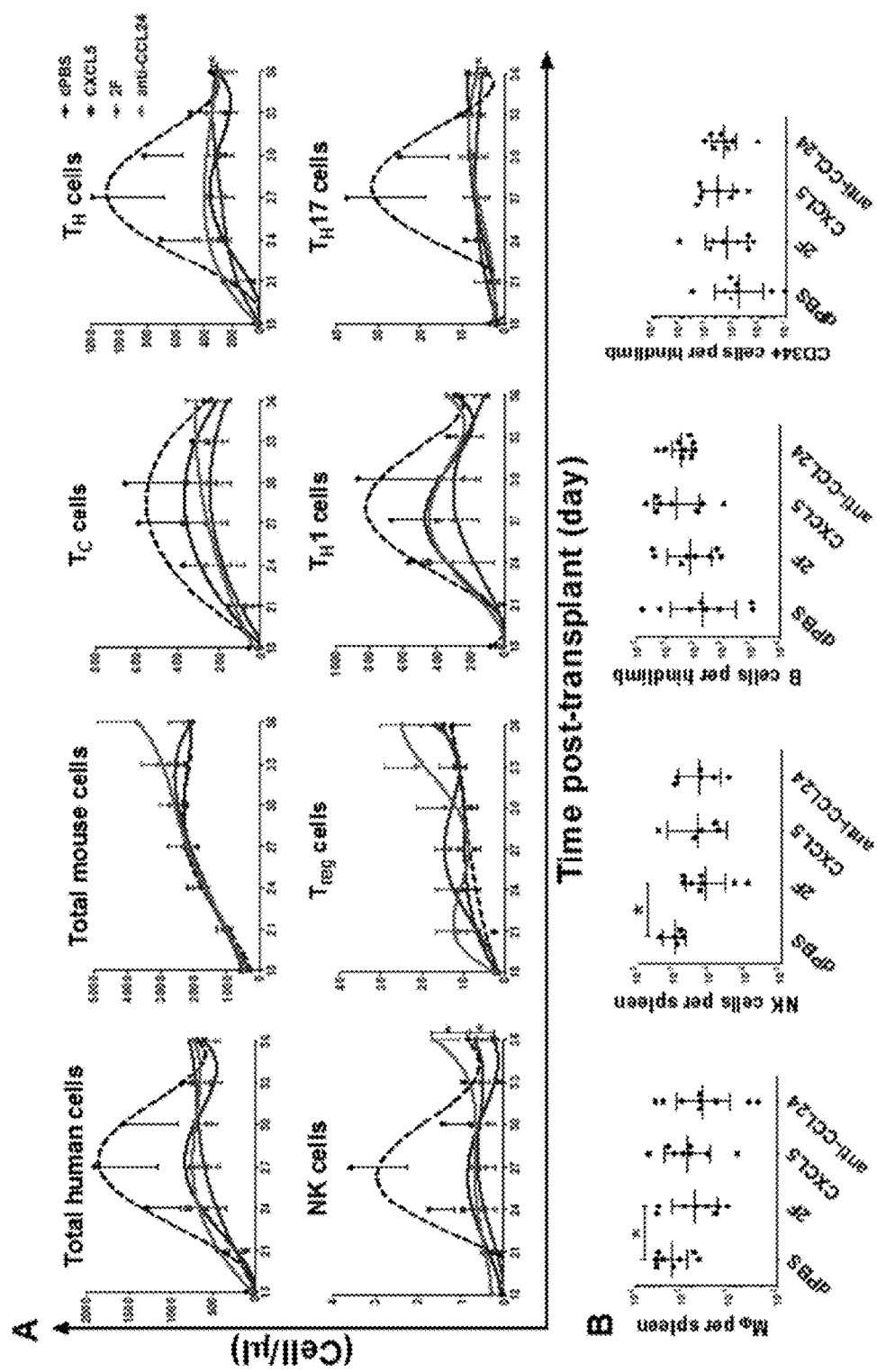
FIG. 10 shows data indicating that a single factor was comparable to 2F cocktail in suppression of human effector cells proliferation and differentiation. (A) shows line graphs showing data that effector cell population changes in peripheral blood. 30-40 ul of mouse peripheral blood was harvested from the tail every 3 days from Day-18 onwards until Day-36PT. Effector cell population changes was monitored by flow cytometry. Results were expressed as mean±S.E. (n=5). (B) shows scatter plots of data points indicating cell population changes in spleen and bone marrow at Day-40 PT. Results were expressed as mean with 95% CI (confidence interval).
Figure 11:
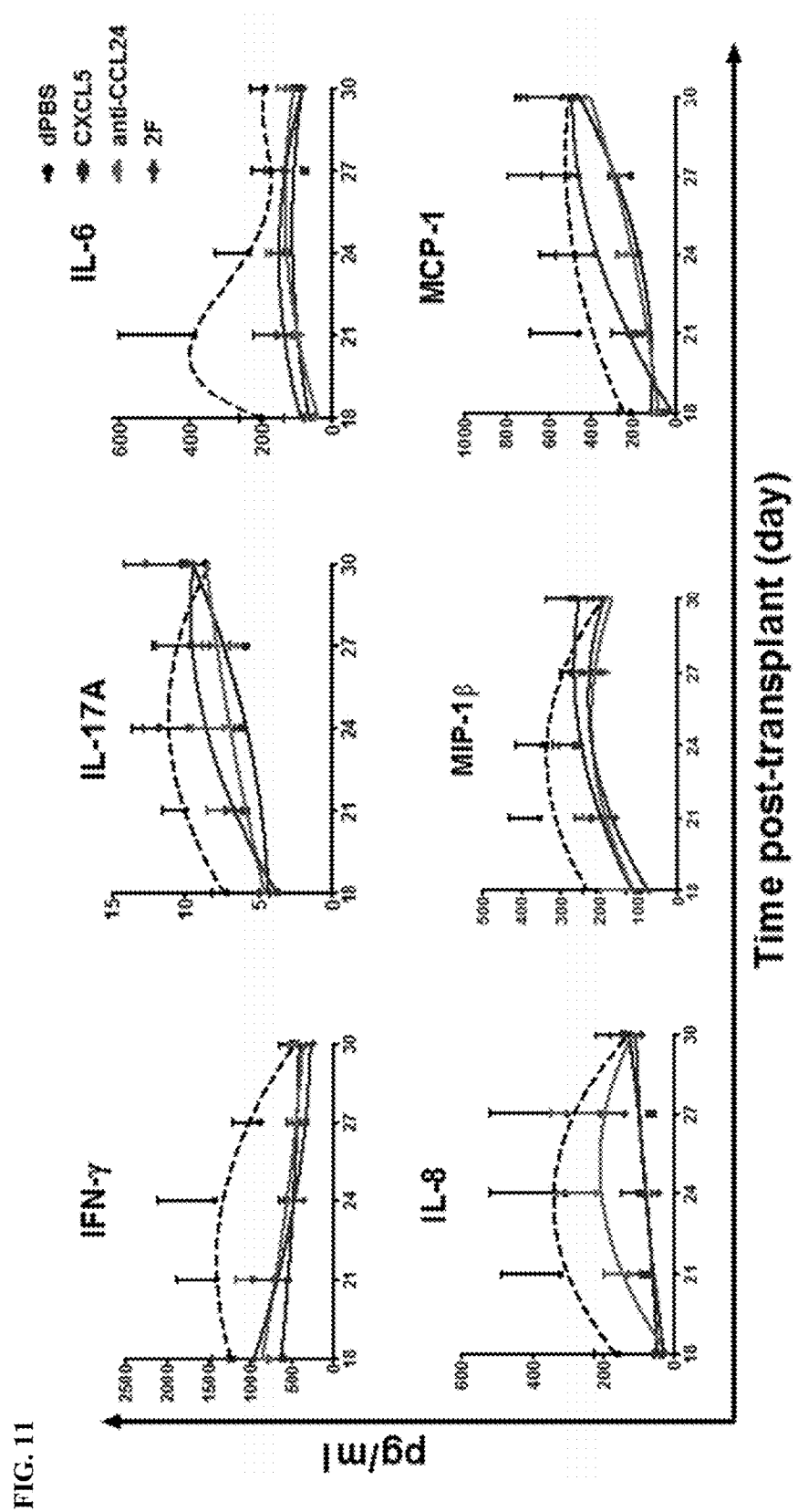
FIG. 11 provides data in the form of line curves, showing that either one of the components of the 2F cocktail was sufficient to suppress human pro-inflammatory cytokines. Plasma isolated from mouse peripheral blood was used for protein assay by Luminex with a 17-plex human cytokine kit. Results were expressed as mean±SD. The profile of different treatments was compared by means of a generalized estimating equation (GEE) model (*, p<0.0167; **, p<0.0033, for multiple comparisons).

In moderate GVHD, anti-CCL24 antibody or CXCL5 could effectively mimic the immunosuppressive effect of the 2F cocktail. It maintained mice 36-day survival at 78.3% (CXCL5: 18/23 mice) and 82.6% (anti-CCL24: 19/23 mice) with mild symptoms, while the 2F cocktail treatment maintained survival at 81.0% (17/21 mice) (FIGS. 9A and 9B). However, in severe GVHD, single factor lost its immunosuppressive capacity. Survival dropped to 26.1% (6/23 mice) and 16.7% (3/18 mice) with moderate symptoms when mice were treated with CXCL5 or anti-CCL24 antibody (FIGS. 9C and 9D). The results were significantly lower than in mice treated with the 2F cocktail (61.9%, 13/21 mice) (p<0.05). Cell population assay demonstrated that CXCL5 or anti-CCL24 antibody alone gave suboptimal immunosuppression effect on circulating CTLs, Th1 cells, splenic macrophages and NK cells (FIGS. 10, A and B). This suggested that the two factors exhibit a concerted effect in severe GVHD. This is consistent with our in vitro observation that MSCs modulated immune reaction through multiple factors rather than through a single factor. It was also supported by the protein assay as CXCL5 was solely comparable to the 2F cocktail in the suppression of pro-inflammatory cytokines IFN-γ, IL-6, IL-8, and MIP-1β; while anti-CCL24 antibody was solely comparable in the suppression of IFN-γ, IL-6 and MIP-1β (FIG. 11).

The 2FC Treatment Attenuated SLE Symptoms and Prolonged the Mice Survival

The 2FC treatment attenuated SLE symptoms and prolonged the mice survival GVHD occurs when the graft rejects the host, whereas autoimmune disease is a condition arising from an abnormal immune response to a normal body part. The underlying principle is about alloimmunity in GVHD and autoimmunity in autoimmune disease. To some extent, they are sharing the same pathogenesis. Because of the profound immunosuppressive capacity in GVHD and the pathogenesis similarity, we intend to validate the pre-clinical efficacy of the 2FC in autoimmune diseases.

Figure 12:
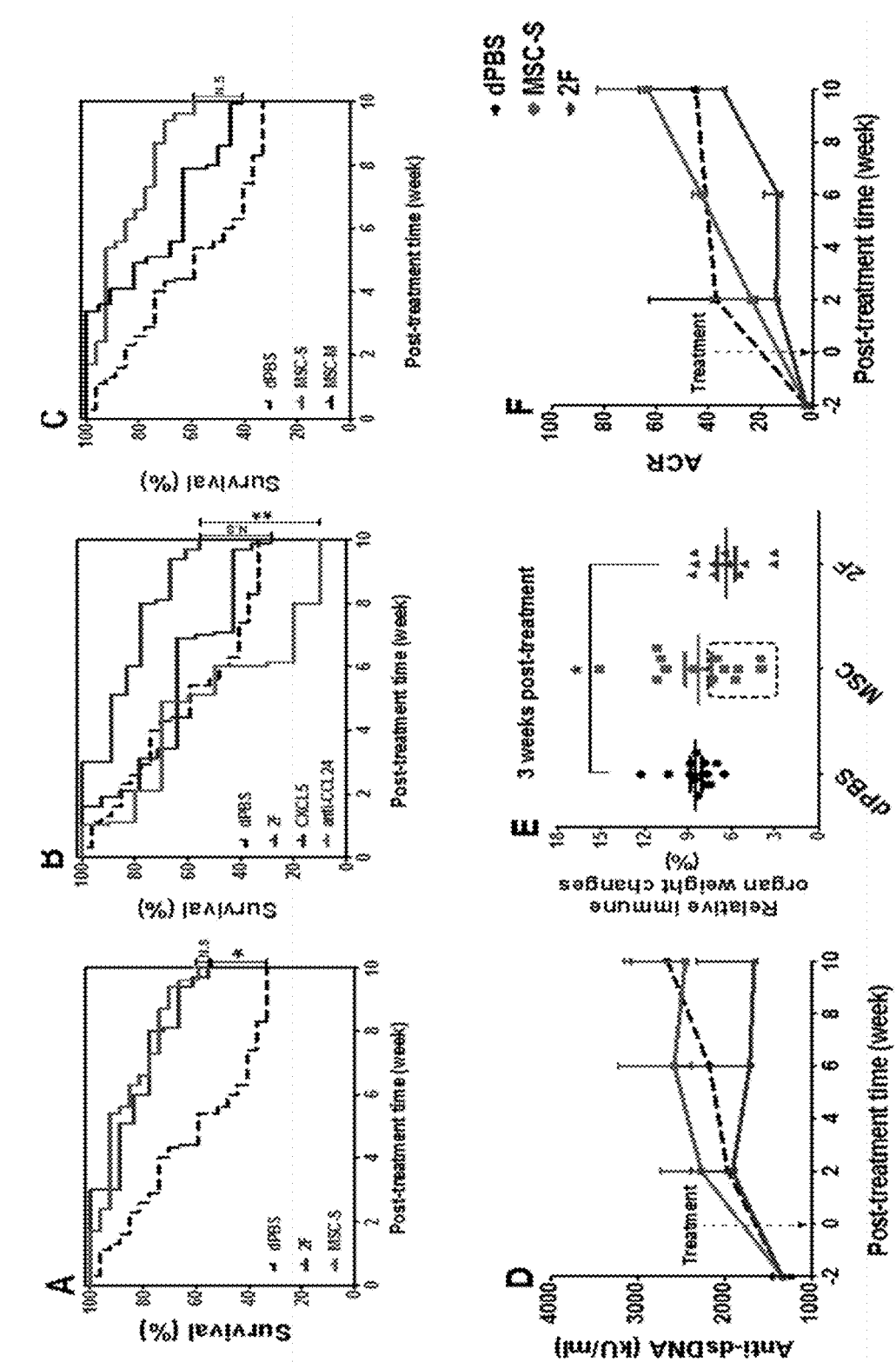
FIG. 12 provides data showing that the 2F cocktail treatment attenuated SLE symptoms and prolonged survival. (A) shows Kaplan-Meier survival curves in mice treated with standard mesenchymal stromal cell treatment (MSC) or 2F cocktail (n=4; $N_{dPBS}$=29 mice, $N_{2F}$=18 mice, $N_{MSC}$=18 mice). (B) shows Kaplan-Meier survival curves in mice treated with 2F cocktail or single factor ($N_{dPBS}$=29 mice, $N_{2F}$=18 mice, $N_{CXCL5}$=14 mice, $N_{anti-CCL24}$=10 mice). (C) shows Kaplan-Meier survival curves in mice treated with single or multiple MSC injection ($N_{dPBS}$=29 mice, $N_{MSC-S}$=18 mice, $N_{MSC-M}$=23 mice). From (A) to (C), the significance is calculated by log-rank test as *p<0.05; p<0.01; *p<0.001; N.S means no significant difference. (D) shows line graphs depicting data showing the plasma autoantibody concentration. Results were expressed as mean±SD. (E) shows dot plots depicting data showing the lymphoproliferation reduction in $Fas^{lpr}$ mice (*p<0.05). (F) shows line graphs depicting data showing the urine albumin-to-creatinine ratio in $Fas^{lpr}$ mice. Results were expressed as mean±SD. (G) shows lymphocyte infiltration in kidney by haematoxylin and eosin (H&E) staining. (H) to (J) The average number of mesenteric lymph node, spleen and thymic effector cells in $Fas^{lpr}$ mice after BM-MSCs and 2FC treatment. Results were expressed by scatter plot with mean value (*p<0.05; p<0.01; *p<0.001).
Figure 12:
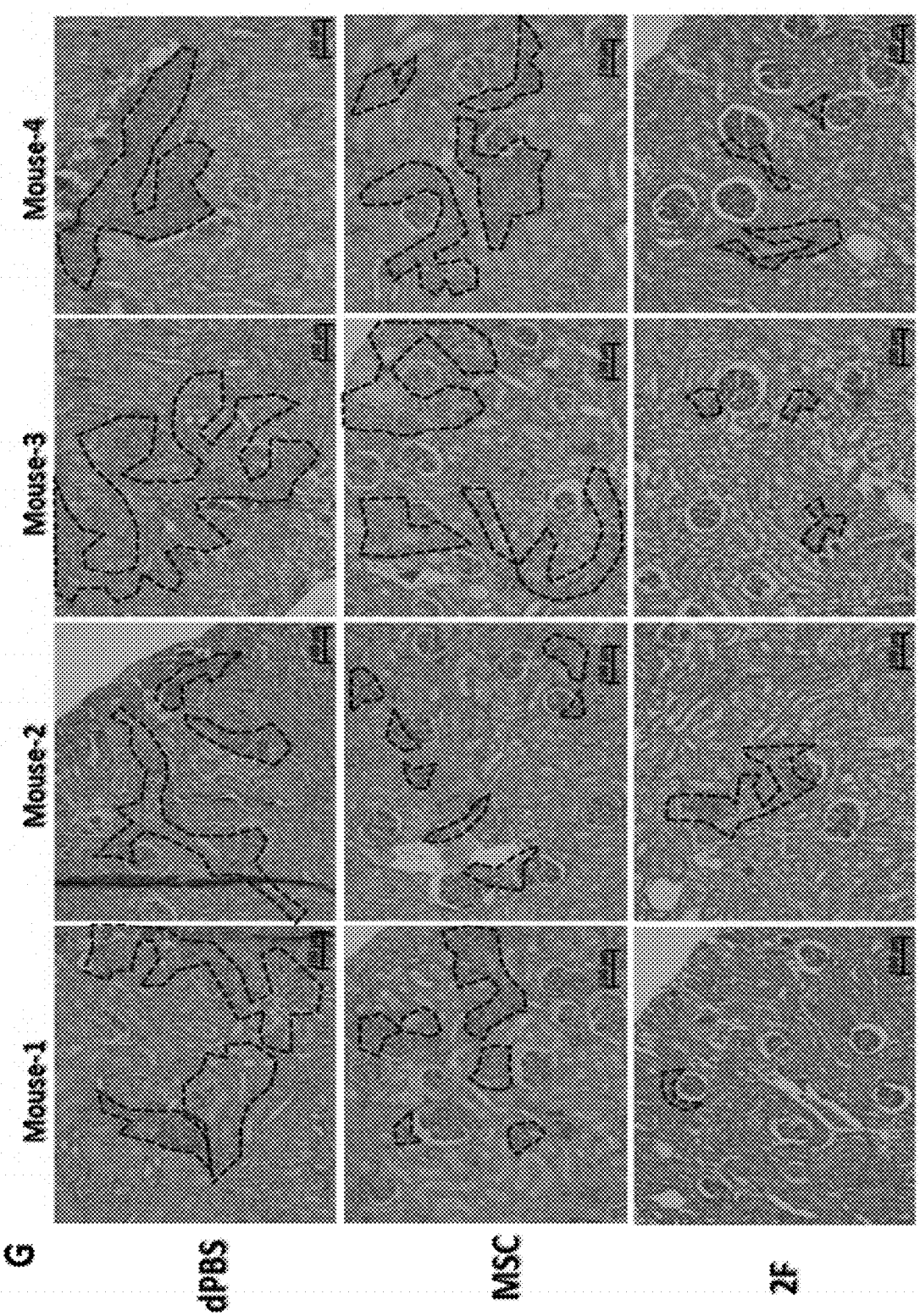
Figure 12:
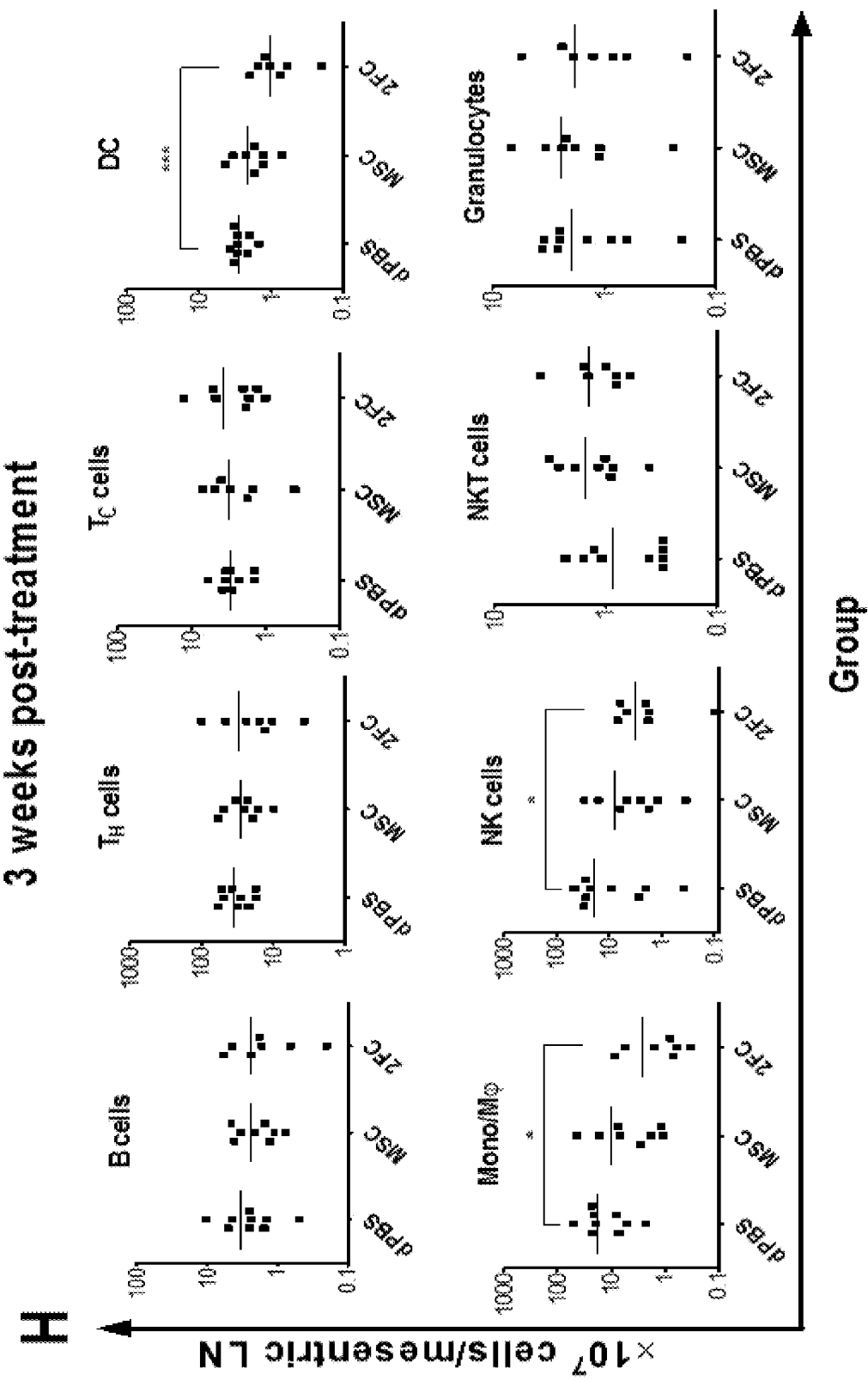
Figure 12:
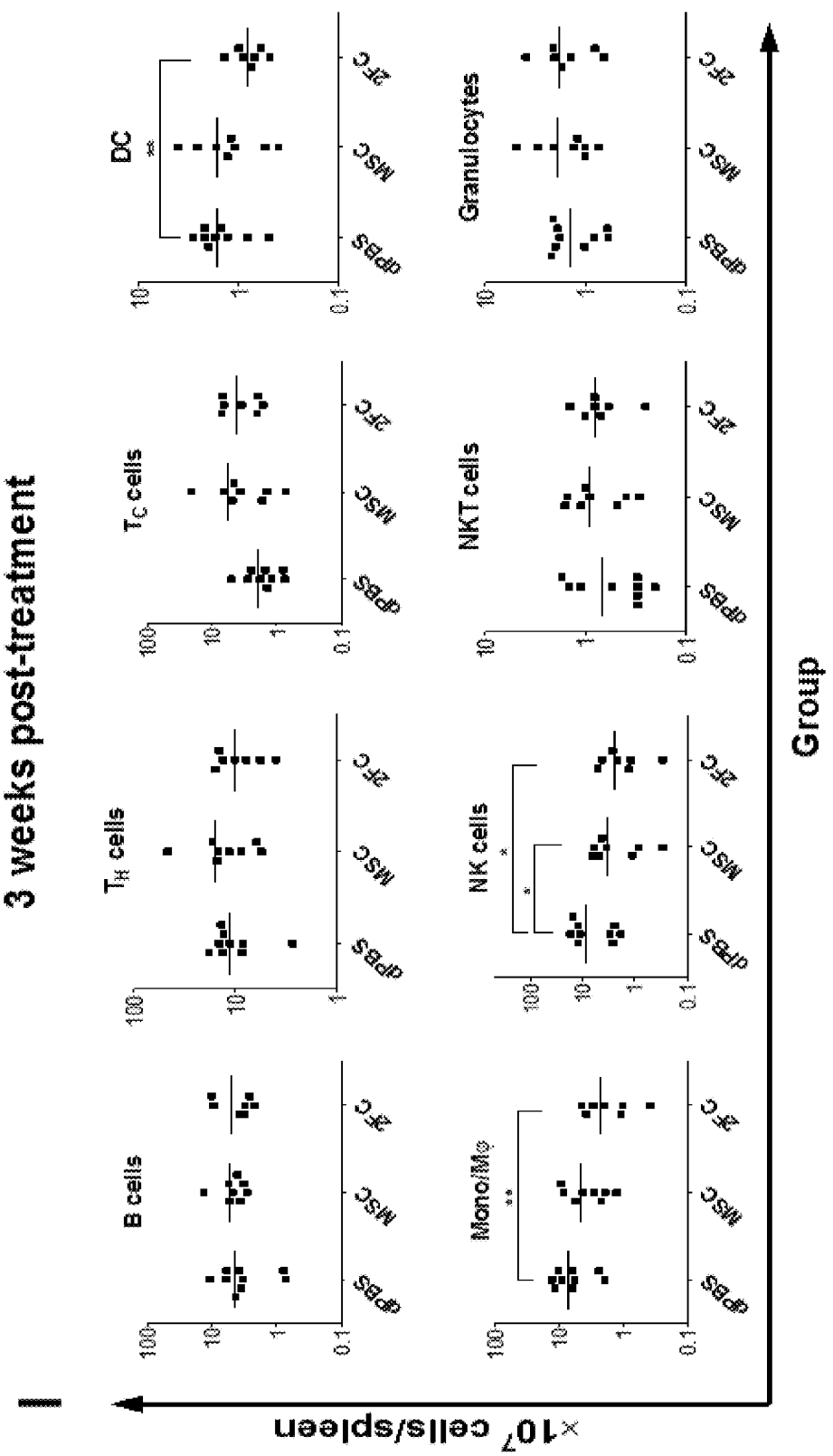
Figure 12:
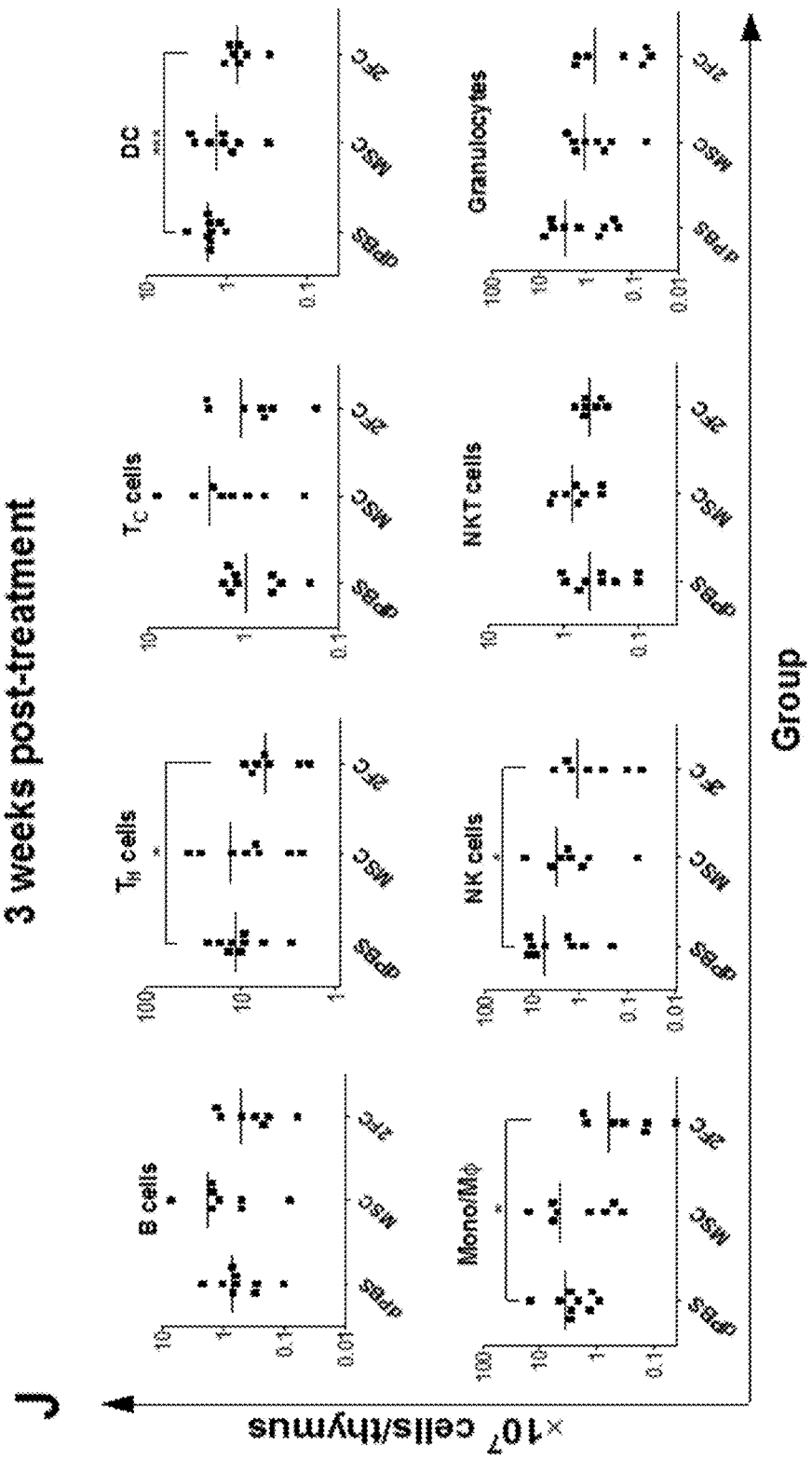

In SLE model, $Fas^{lpr}$ mice 10 weeks post-treatment survival was significantly improved from 33.3% (dPBS: 9/27 mice) to 55.6% (2FC: 10/18 mice, p<0.05), which was comparable to BM-MSCs treatment (59.3%, 16/27 mice) (FIG. 12, A). It was better than single factor CXCL5 (28.6%, 4/14 mice) or anti-CCL24 antibody (10%, 1/10 mice) treatment (FIG. 12, B, p<0.05). This result suggests that CXCL5 concerted with anti-CCL24 antibody to exert its immunosuppression function. In addition, single BM-MSC treatment was better than multiple BM-MSC (monthly) treatment (39.1%, 9/23 mice) even the significance was not achieved (FIG. 12, C). For autoantibody secretion including IgA, IgG and IgM, the 2FC treatment reduced its increasing rate. However, this phenomenon was not observed in BM-MSCs treatment (FIG. 12, D). The lymphoproliferation was reduced as the weight of mesenteric lymph node, spleen and thymus relative to its own body weight was reduced from 8.4% to 6.3% when mice were treated with the 2FC for 3 weeks (p<0.05). While this effect was only observed in part of $Fas^{lpr}$ mice when mice were treated with BM-MSCs (FIG. 12, E). Mice kidney function was improved as the 2FC treatment continuously slowed down the ACR increment during 10 weeks treatment period, while BM-MSCs treatment could only provide the short term protection for 4-5 weeks and then lost its kidney protection function (FIG. 12, F). This phenomenon was consistent with histological observation (FIG. 12, G). The massive lymphocytes infiltration was significantly reduced in mice treated with the 2FC, while just reduced in some mice those treated with BM-MSCs. The proliferation of effector cells, such as dendritic cells (DCs), monocytes/macrophages and natural killer cells (NK cells) were significantly suppressed in mesenteric lymph nodes (LN), thymus and spleen by the 2FC treatment (FIGS. 12, H and I). Beyond that, helper T cells were also suppressed significantly in thymus (FIG. 12, J). These effects were more potent than those observed with BM-MSCs treatment.

As a person skilled in the art will appreciate, the data and information provided in the sections below was generated using mouse models to simulate or emulate diseased states. For example, bleomycin-induced scleroderma was shown as a murine model for (human) systemic sclerosis. In the same line, collagen-induced arthritis is a murine model for the study of (human) rheumatoid arthritis.

Quantitative Classification of Diffuse Alveolar Haemorrhage (DAH) Mouse Model

Figure 13:
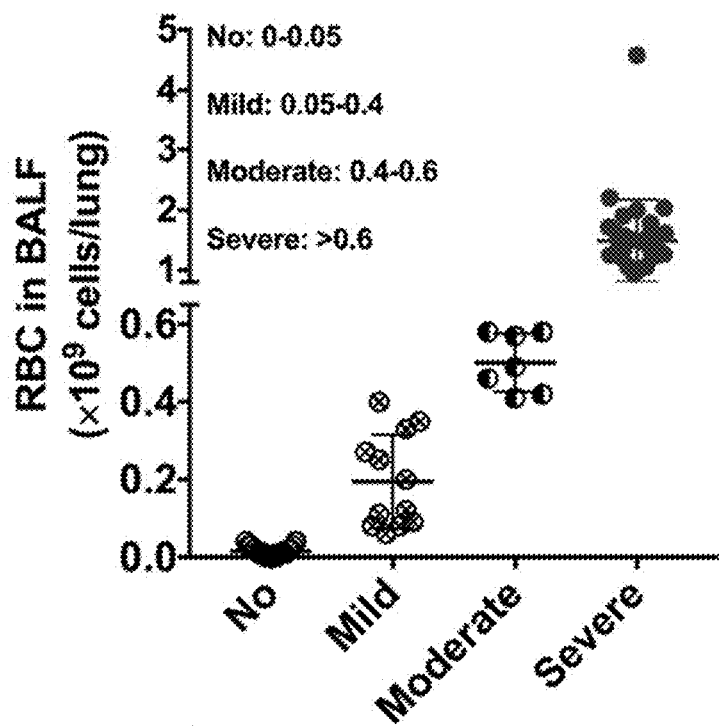
FIG. 13 shows information as to the classification of disease severity in the diffuse alveolar haemorrhage (DAH) mouse model. (A) shows a box plot showing the correlation of murine red blood cell (RBC) count in bronchoalveolar lavage fluid (BALF). (B) shows micrograph images of the gross appearance and histopathological (100× magnification) changes in the lungs of pristane-induced mice. (C) shows a line graph plotting the changes in body weight. (D) shows mice survival post-pristane induction.
Figure 13:
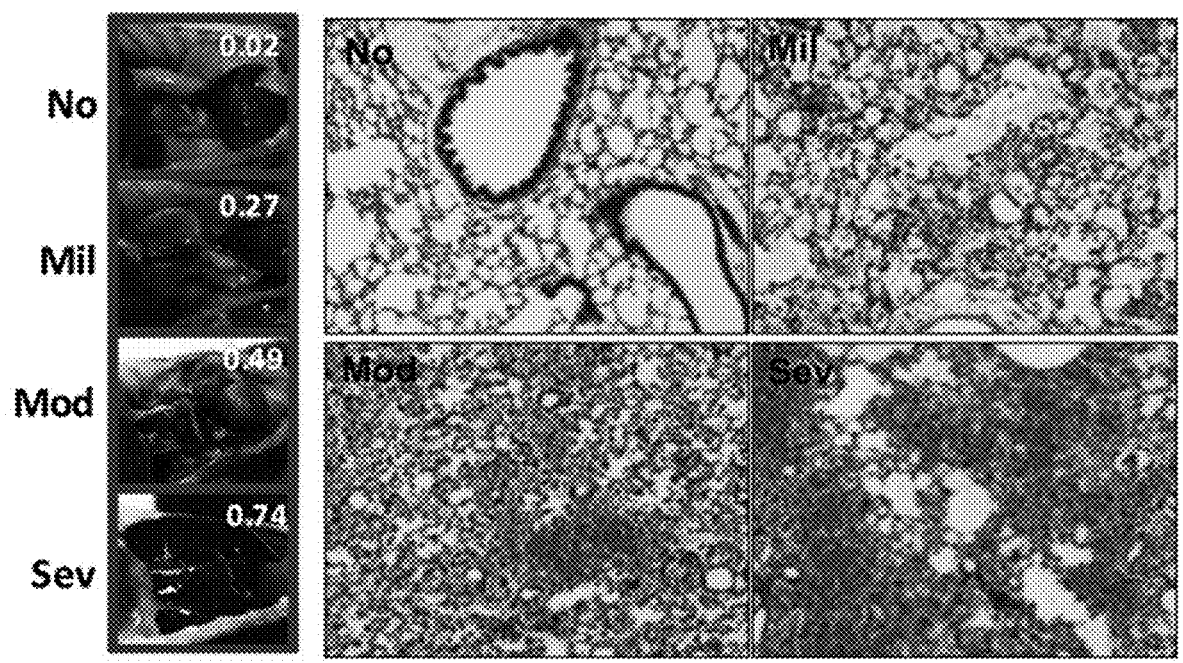
Figure 13:
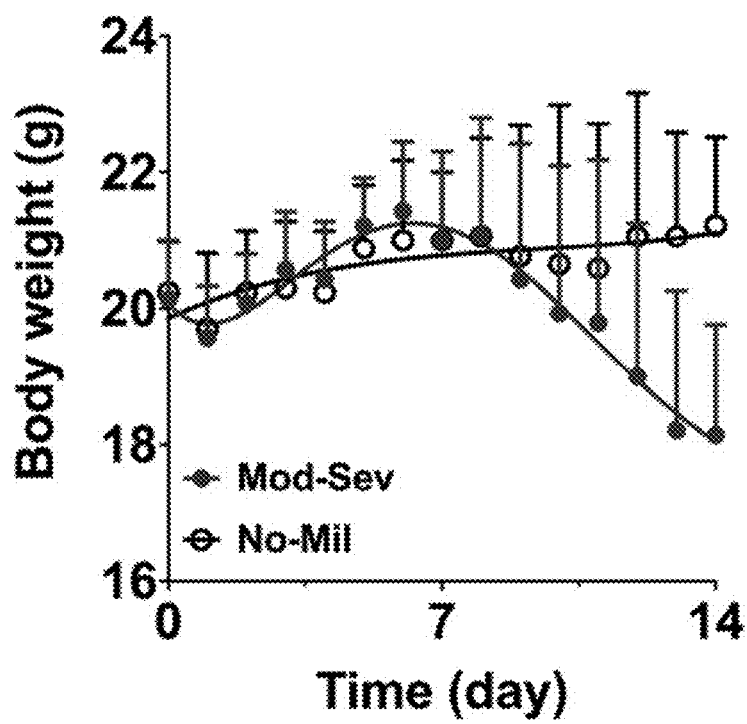
Figure 13:
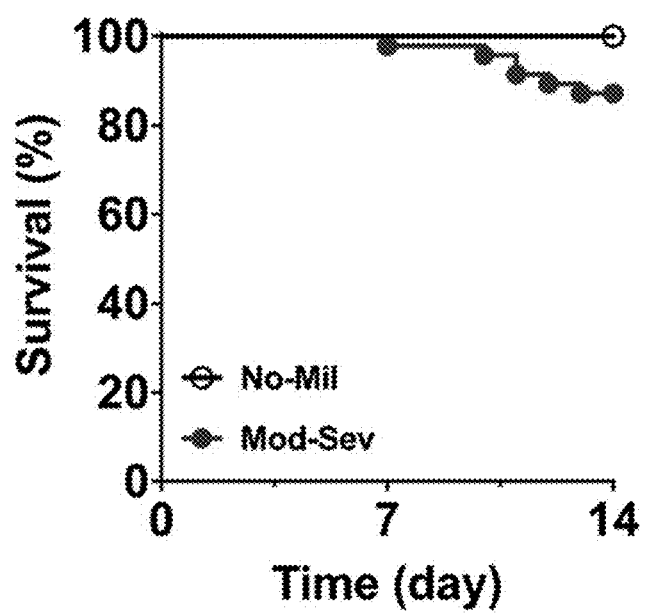

Contrary to previous reports on partial or complete bleeding, the prevalence of diffuse alveolar haemorrhage as provided herein was classified quantitatively by red blood cell (RBC) count in bronchoalveolar lavage fluid (BALF) (FIGS. 13A and 13B). With this quantitative classification, a good positive linear correlation was formed between red blood cell count and bleeding severity, resulting in an accurate and simple classification. The mice maintained their bodyweight and survived, if they did not develop, or only developed a mild degree, of diffuse alveolar haemorrhage. However, some mice started to lose body weight around seven days after pristane-induction and died gradually, if they developed a moderate to severe degree of diffuse alveolar haemorrhage (FIGS. 13C and 13D).

Effector Cells Change Upon Lung Inflammation

Figure 14:
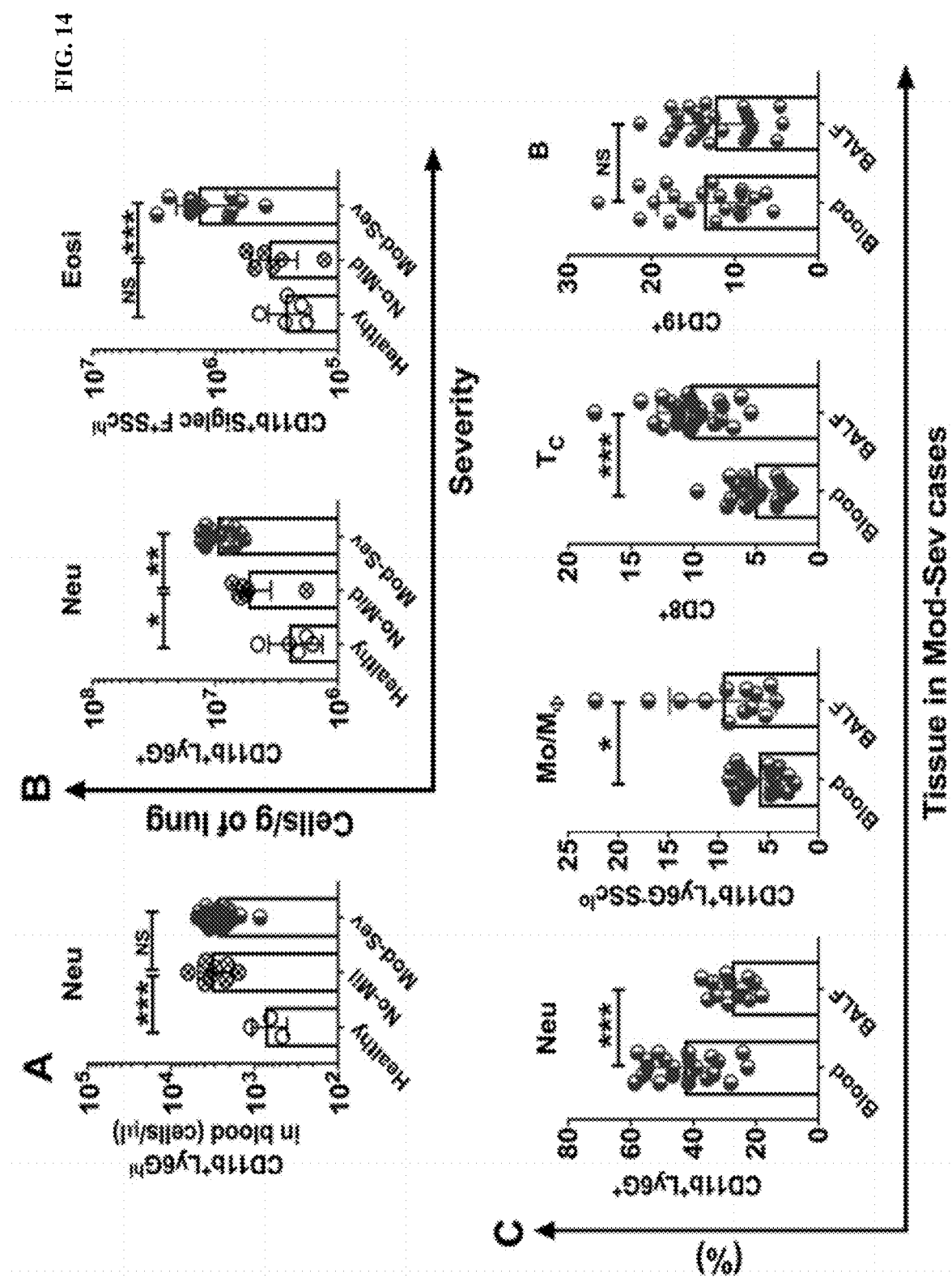
FIG. 14 shows effector cell changes in blood and lung. (A) is a column graph showing the absolute count of neutrophils in blood. (B) shows column graphs illustrating the absolute count of neutrophils and eosinophils, respectively, in lung tissue. (C) shows column graphs depicting the relative count of neutrophils (neu), monocytes (Mo), macrophages ($M_\Phi$), cytotoxic T lymphocytes (CTLs; $T_c$) and B cells (B) in blood and bronchoalveolar lavage fluid (BALF), in moderate to severe case of diffuse alveolar haemorrhage (DAH). For t-test: *-$p<0.05$; -$p<0.01$; *-$p<0.001$. For multiple comparison (Bonferroni test): *-$p<0.025$; -$p<0.005$; *-$p<0.0005$ when n=2.

Upon pristane-induction, neutrophils significantly increased in blood, irrespective of whether a clear, mild or moderate to severe degree of lung bleeding was present, compared to healthy mice (FIG. 14A). These increased neutrophils, together with eosinophils, were shown to have further migrated to lung tissue (FIG. 14B). There was no difference in terms of effector cell influx between healthy mice and mice without bleeding or bearing mild level of diffuse alveolar hemorrhage. A significantly high number of effector cells including T cells, B cells, neutrophils, eosinophils, monocytes and natural killer cells was shown to have flooded into lung tissue, if the disease severity developed to moderate to severe degree (data not shown). Based on this observation, it was thought that if there was no any specific chemotactic attraction, the proportion of each effector cell type, which flooded into lung tissue, should be same as the proportion of blood in moderate to severe cases. However, a high proportion of monocytes and cytotoxic T lymphocytes (CTLs), not including neutrophils and B cells, was observed to be attracted and accumulated in bronchoalveolar lavage fluid (FIG. 14C).

The Potential Pathogenic Role of Neutrophil and Monocyte/Macrophage

Cytokines are critical coordinators of the immune response necessary for resolving bacterial and viral assaults on the immune system. The chemokine CXCL1/KC plays a pivotal role in the host immune response by recruiting and activating neutrophils for microbial killing at the tissue site. CXCL1 exists reversibly as monomers and dimers, and mediates its function by binding glycosaminoglycans (GAG) and CXCR2 receptor. It may play a role in inflammation and exerts its effects on endothelial cells in an autocrine fashion. IL-12 is produced primarily by monocytes, macrophages, dendritic cells (DCs), and B cells. The major functions of IL-12 include induction of IFN-r production from natural killer (NK) cells and T cells, enhancement of cytotoxicity of natural killer cells and cytotoxic T lymphocytes (CTLs), and differentiation of naïve T cells into $T_H1$ effectors, suggesting a key role for IL-12 in the development of cell-mediated immunity.

Figure 15:
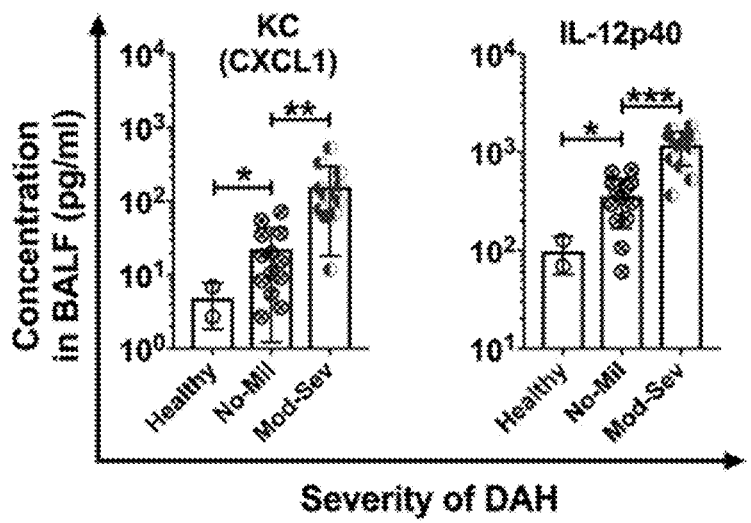
FIG. 15 shows column graphs depicting neutrophil and monocyte/macrophage-related cytokines. The concentration of secreted-cytokines in bronchoalveolar lavage fluid (BALF) is plotted against the severity of diffuse alveolar haemorrhage (DAH). All lungs were perfused with 1 ml of dPBS after sacrificing. The concentration of cytokines in bronchoalveolar lavage fluid (BALF) was measured using a Luminex kit. For multiple t-test comparison: *-$p<0.025$; -$p<0.005$; *-$p<0.0005$ when n=2.

Both of CXCL1 and IL-12p40 were observed significantly increased in bronchoalveolar lavage fluid and positively correlated with the severity of bleeding (FIG. 15). This result indicated that the potentially pathogenic role of neutrophil and monocyte/macrophage in the development of diffuse alveolar hemorrhage.

Helper T Cells are not Involved in the Pathogenesis of Diffuse Alveolar Haemorrhage (DAH)

Figure 16:
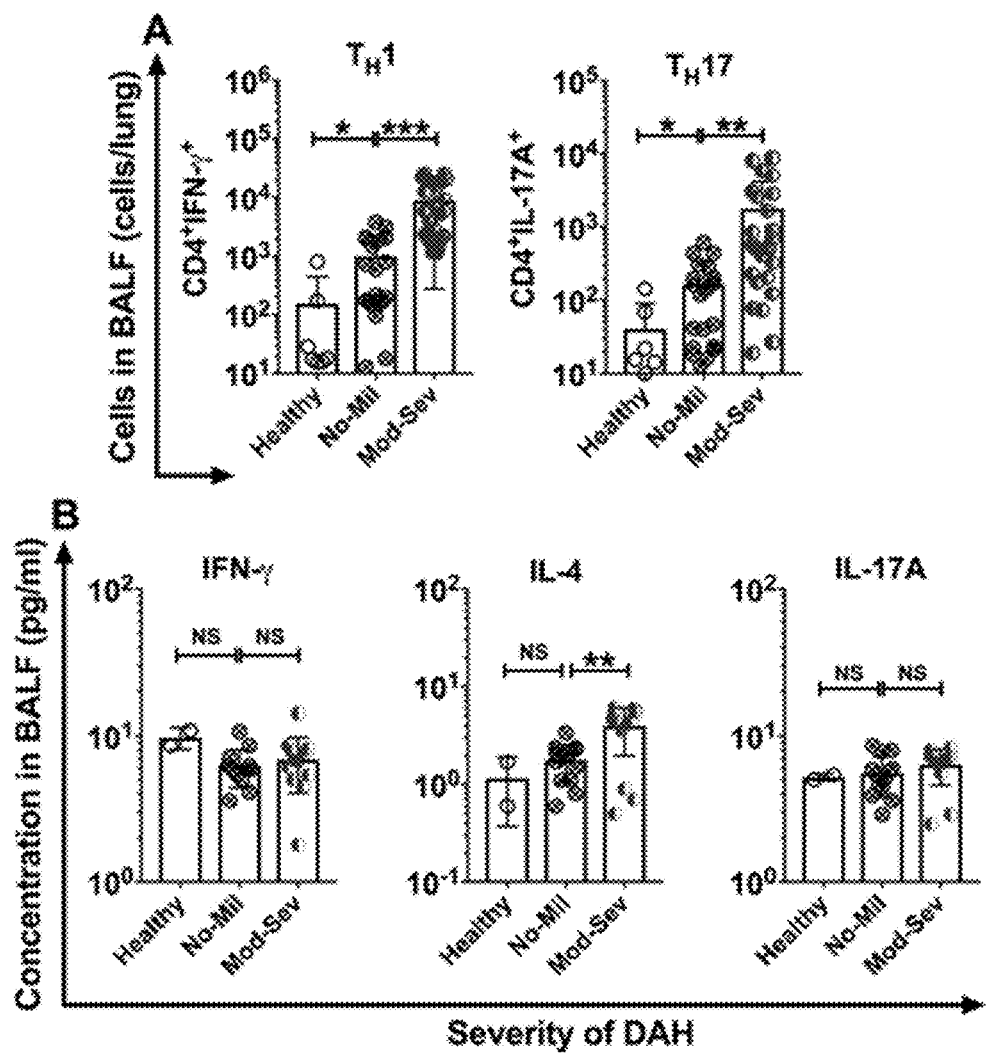
FIG. 16 shows column graphs illustrating helper T cell changes and cytokine secretion. (A) shows column graphs of the number of $T_H1$ and $T_H17$ cells in bronchoalveolar lavage fluid (BALF). (B) shows column graphs of the concentration of secreted-cytokines in bronchoalveolar lavage fluid (BALF). All lungs were perfused with 1 ml of dPBS after sacrificing. The concentration of cytokines in bronchoalveolar lavage fluid (BALF) was measured using a Luminex kit. For multiple t-test comparison: *-$p<0.025$; -$p<0.005$; *-$p<0.0005$ when n=2.

$T_H1$ and $T_H17$ cells were significantly increased in bronchoalveolar lavage fluid when inflammation happened (FIG. 16A), but the expression of their secreted cytokines IFN-r and IL 17A was not changed, no matter how severe the bleeding was (FIG. 16B). This result indicated that helper T cells were not activated and pathogenically involved in the development of diffuse alveolar hemorrhage. In addition, although a high amount of IL-4 was detected in severe cases of bleeding, no $T_H2$ cells were in bronchoalveolar lavage fluid. This result indicated that this IL-4 might secret by the significantly increased neutrophils in bronchoalveolar lavage fluid.

B Cells Mediate Diffuse Alveolar Haemorrhage (DAH) Via IgM and IgA

Figure 17:
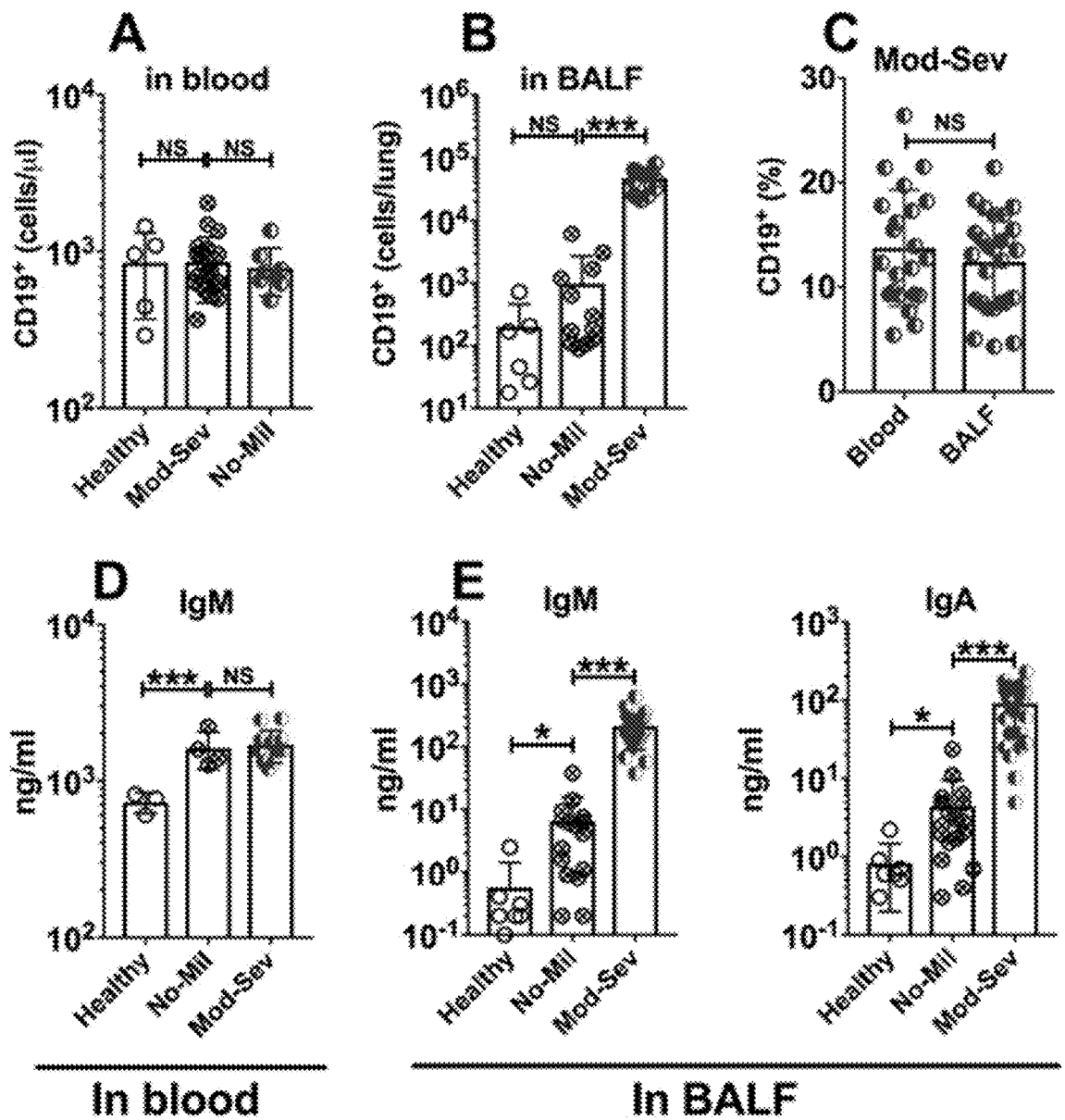
FIG. 17 shows column graphs depicting B cell changes and antibody secretion. (A) and (B) are column graphs showing the changes in B cells in (A) blood and (B) bronchoalveolar lavage fluid (BALF), respectively, before and after pristane-induction. (C) is a column graph showing the relative change in B cells in blood and bronchoalveolar lavage fluid (BALF) in moderate to severe case of DAH. (D) and (E) are column graphs showing IgM and IgA secretion in blood and bronchoalveolar lavage fluid (BALF), respectively, before and after pristane-induction. For multiple t-test comparison: *-$p<0.025$; -$p<0.005$; *-$p<0.0005$ when n=2.

The number of B cells in blood was not changed upon inflammation, but the secretion of IgM was increased (FIGS. 17A and 17D). Similarly, in bronchoalveolar lavage fluid, there was no difference on number of B cells between healthy and mild mouse, but the secretion of IgM and IgA were increased (FIGS. 17B and 17E). Despite the accumulation of B cells in moderate and severe case of diffuse alveolar hemorrhage, the proportion of B cells in blood and bronchoalveolar lavage fluid was not changed (FIG. 17C). This result indicated that B cells were only naturally flooded in, rather than chemotactically recruited to, the inflamed lung.

Figure 18:
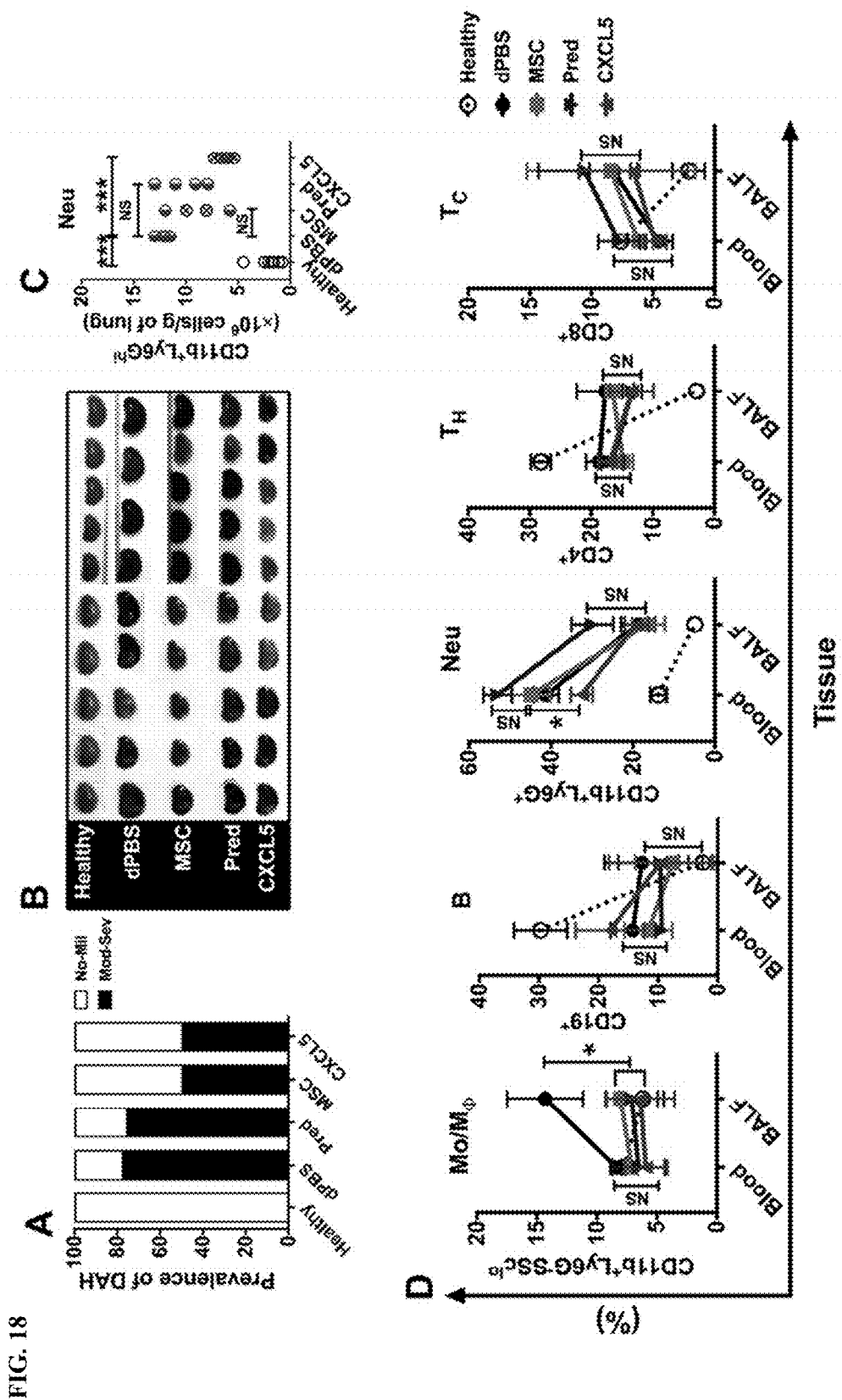
FIG. 18 shows treatment effect and targeting cells. (A) and (B) show a histogram depicting the prevalence of diffuse alveolar haemorrhage (DAH), and images showing the gross appearance of an inflamed lung, respectively. (C) shows the results of treatment and the effect of said treatment on pulmonary infiltration of neutrophils. (D) Treatment effect on effector cell proportion changes in blood and bronchoalveolar lavage fluid (BALF). For multiple t-test comparison: *-$p<0.025$; -$p<0.005$; *-$p<0.0005$ when n=2.

CXCL5 Ameliorates Diffuse Alveolar Haemorrhage (DAH) Via Concordant Effect of Suppressing Pulmonary Neutrophils Infiltration and Reducing the Accumulation of Macrophages and B Cells With standard treatment, the prevalence of moderate to severe diffuse alveolar haemorrhage was reduced from 77.8% (14/18 mice, dPBS) to 76.5% (13/17 mice, prednisolone) via a reduction in the accumulation of macrophages in bronchoalveolar lavage fluid (FIGS. 18A, 18B and 18D). This effect could be further extended to 50.0% (9/18 mice) by mesenchymal stem cell (MSC) treatment (FIGS. 18A, 18B and 18D) by reducing the accumulation of macrophages and B cells in bronchoalveolar lavage fluid. Similar to mesenchymal stem cell treatment, CXCL5 treatment reduced the prevalence of DAH to 50.0% (7/14 mice) (FIGS. 18A and 18B) via concordant effect of suppressing pulmonary neutrophils infiltration (FIG. 18C), reducing the accumulation of macrophages and B cells in bronchoalveolar lavage fluid and proliferation of neutrophils in blood (FIG. 18D). These treatments did not appear to have an effect on T cells, although the proportion of cytotoxic T lymphocytes (CTLs) was increased in bronchoalveolar lavage fluid (FIG. 14C).

Effector Cell Changes and Cytokine Secretion in Collagen-Induced Arthritis (CIA)

Figure 19:
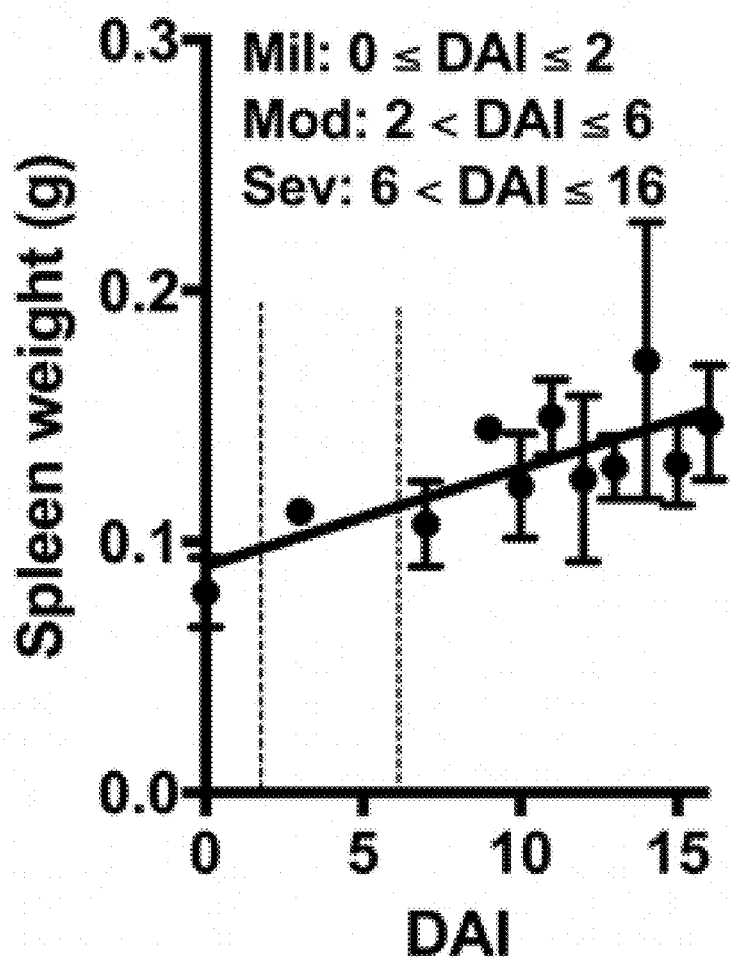
FIG. 19 shows a scatter plot depicting the correlation of disease activity index (DAI) and spleen weight. Disease severity was classified into mild, moderate and severe three categories, respectively, when the disease activity index (DAI) was less than 2 (mild), between 2 to 6 (moderate), and higher than 6 (severe).
Figure 20:
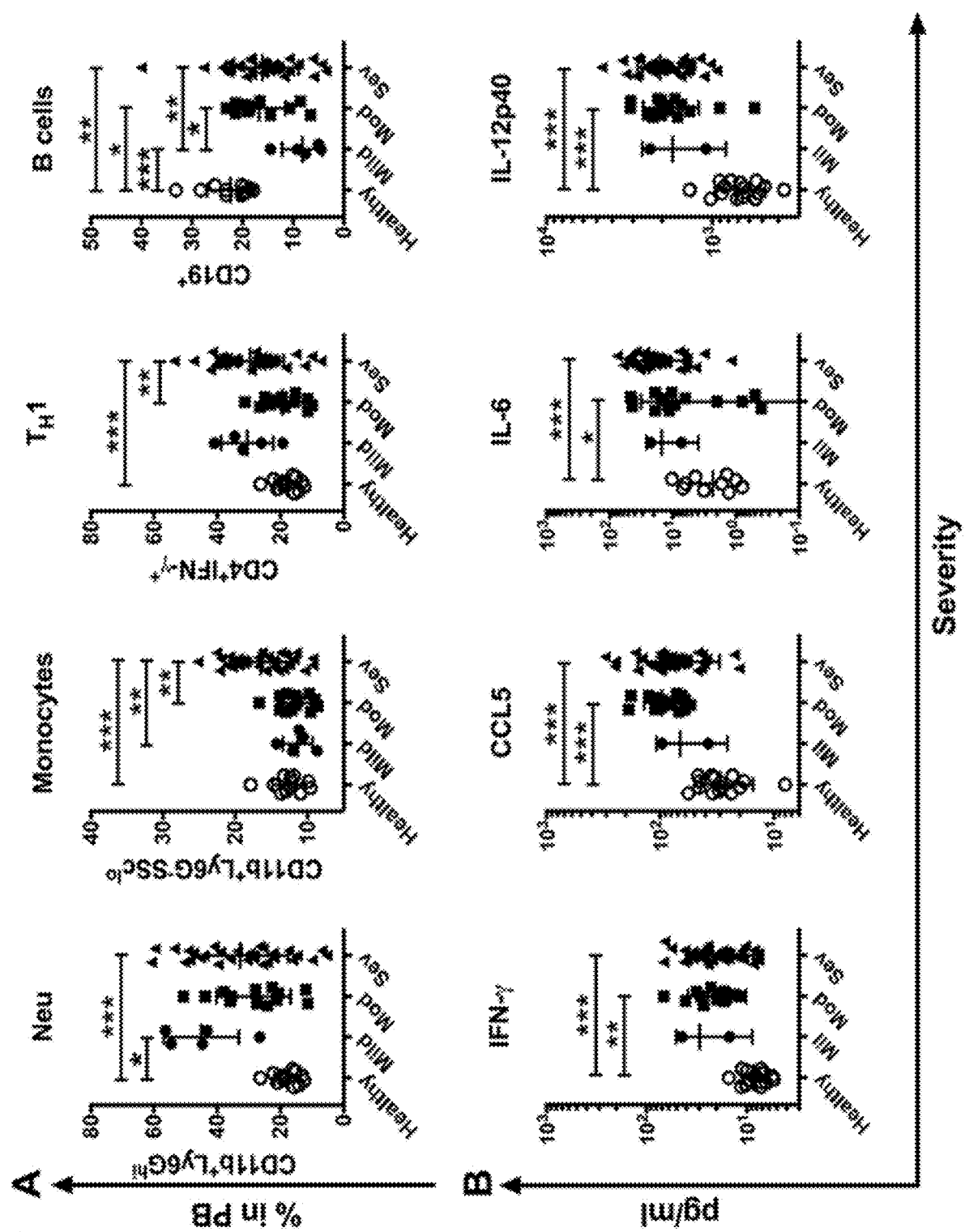
FIG. 20 shows box plots depicting effector cell changes and cytokine secretion. (A) shows box plots illustrating the relative changes of effector cells in peripheral blood (PB). Neu—neutrophils. (B) shows column graphs illustrating cytokine secretion in plasma. For multiple t-test comparison: *-$p<0.01$; -$p<0.002$; *-$p<0.0002$ when n=5.

Upon 40 to 50 days post-collagen induction, the DBA/1J mice developed different degrees of arthritis with swollen toes and ankles. Based on the clinical observation, the paw was scored to 0 to 4, with a maximal total sum of 16 (Table 8). The disease severity was classified into mild, moderate and severe three categories, whereby the total sum of disease activity index (DAI) was less than 2, between 2 to 6 and beyond 6, respectively. There was a strong linear correlation between DAI and spleen size (FIG. 19). Due to inflammation, the proportion of circulating neutrophils, monocytes and $T_H1$ cells was significantly increased in severe cases, while B cells were decreased in the same (FIG. 20A). Concordantly, IFN-γ, CCL5, IL-6, IL-12, T cell- and monocyte-related cytokines were also significantly elevated in blood (FIG. 20B). Both the elevated effector cells and cytokines contributed to the development of collagen-induced arthritis (CIA).

CXCL5 Mimics Mesenchymal Stem Cells (MSCs) to Ameliorate Collagen-Induced Arthritis (CIA)

Figure 21:
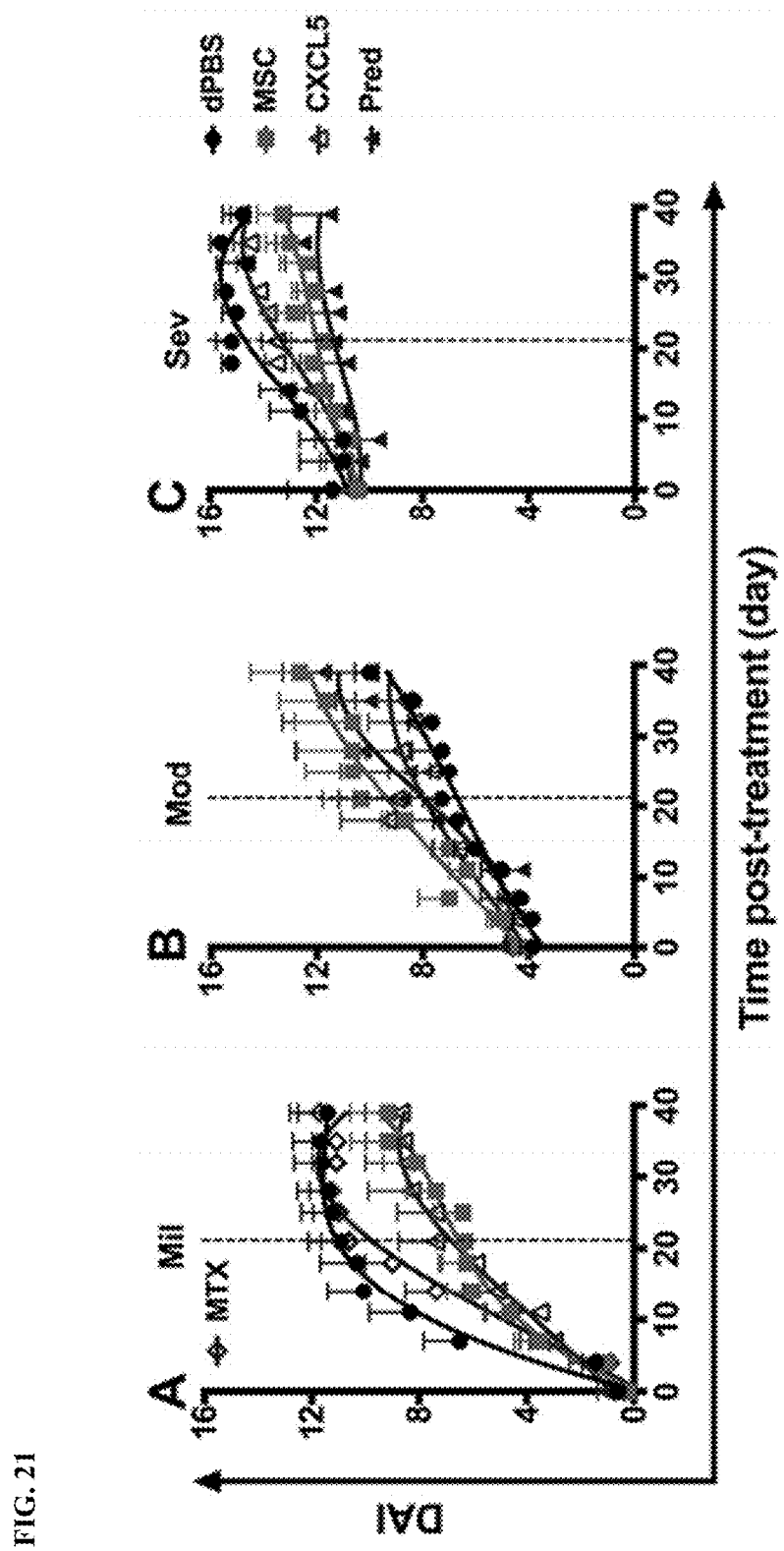
FIG. 21 shows data illustrating the effect of treatment on collagen-induced arthritis (CIA). The treatment was started on (A) mild, (B) moderate and (C) severe collagen-induced arthritis (CIA). MTX—methotrexate; MSC—mesenchymal stem cell; Pred—prednisolone. For multiple t-test comparison: *-$p<0.017$; -$p<0.0033$; *-$p<0.00033$ when n=3-5.

When treatment was started on mice with mild arthritis, CXCL5 and mesenchymal stem cells were able to slow down the development of arthritis and eventually kept the disease activity index (DAI) at 8.7±4.2 (CXCL5) and 9.2±5.1 (MSCs) compared to a control 11.4±3.8 (dPBS) (FIG. 21A, p<0.05). This effect was not observed in treatment using methotrexate (MTX; 11.5±2.8). When treatment started on mice with moderate or severe arthritis, no effect on symptom relief was apparent (FIGS. 21B and 21C). These results indicated that treatment of early onset disease was shown to improve disease outcome, compared to treatment of the disease at a later stage.

Figure 22:
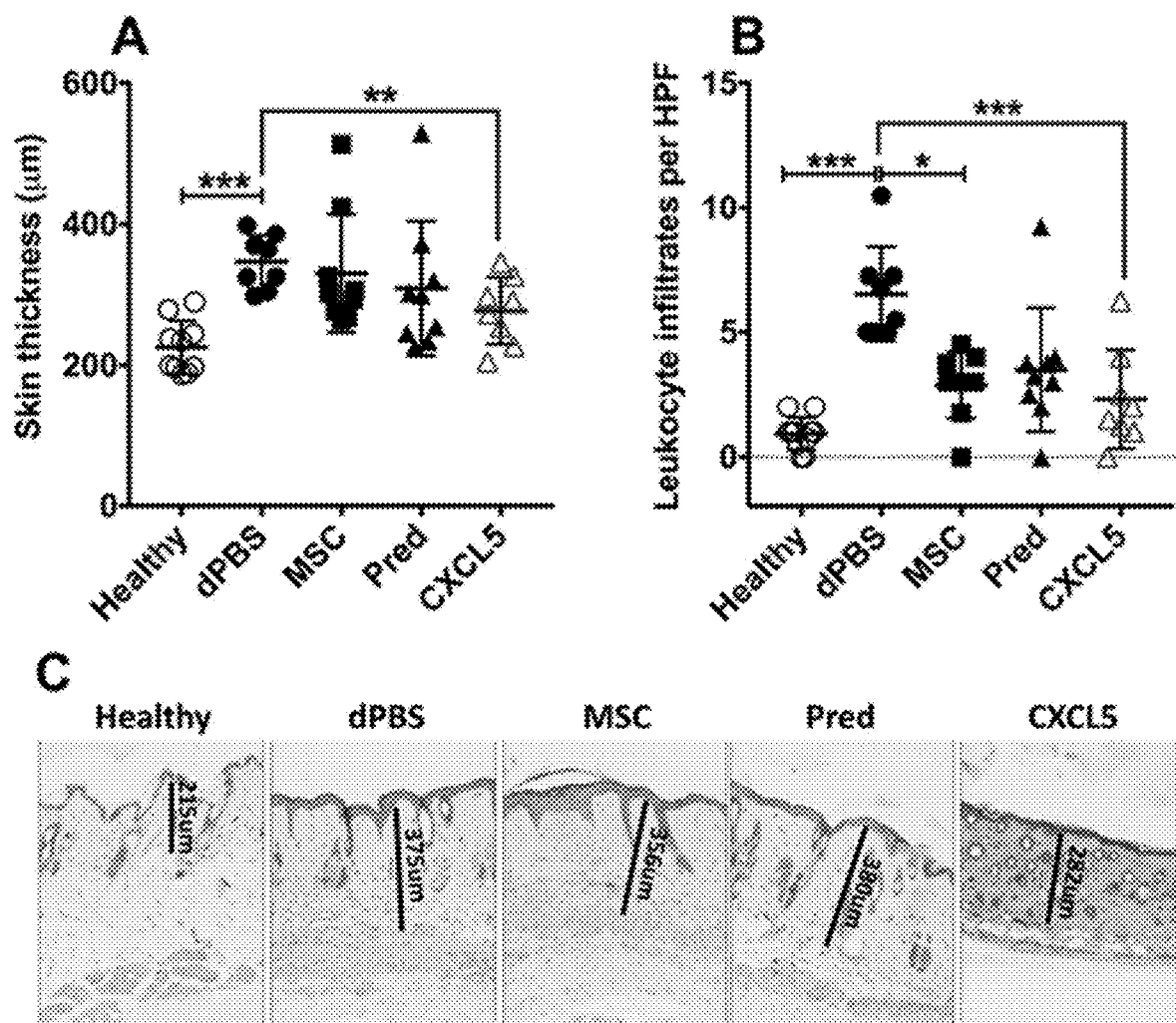
FIG. 22 shows micrograph images showing the effect of treatment on systemic sclerosis (SSc). (A) shows a box plot illustrating skin thickness of DBA/2J mice. (B) shows a box plot of leukocyte infiltration in the dermis. The number of infiltrated leukocytes was counted on randomly-taken photos with High Power Field (HPF; magnification 400×). Five photos were taken for each mouse. The average number from these five photos was used for each mouse. (C) shows micrograph images of representative hematoxylin & eosin (H&E) staining slides. MSC—mesenchymal stem cell; Pred—prednisolone. For multiple t-test comparison: *-$p<0.0125$; -$p<0.0025$; *-$p<0.00025$ when n=4.

CXCL5 Shows Improved Treatment Results Compared to Mesenchymal Stem Cell (MSC) and Prednisolone Treatment for Reducing Skin Thickness in Systemic Sclerosis by Suppressing Proliferation of Monocytes and $T_H1$ cells Mouse systemic sclerosis was induced via a 3-week bleomycin subcutaneous injection regime as outlined above. Post-treatment with bleomycin, mouse skin thickness was increased from 225.4±37.4 μm (healthy) to 346.1±37.9 μm (dPBS) (FIGS. 22A and 22C). It is noted that only a portion of the bleomycin-treated mice responded to the standard therapy using prednisolone or bone marrow-derived mesenchymal stem cell (BM-MSCs) therapy. Skin thickness was reduced to 309.0±95.3 μm (prednisolone) and 330.2±84.2 μm (BM-MSC). Treatment with CXCL5 chemokine was shown to reduce the skin thickness to 277.2±47.6 μm (FIGS. 22A and 22C). Without being bound by theory, it is thought that this is achieved by suppressing the proliferation of monocytes and $T_H1$ cells in peripheral blood (PB) (FIG.

Figure 23:
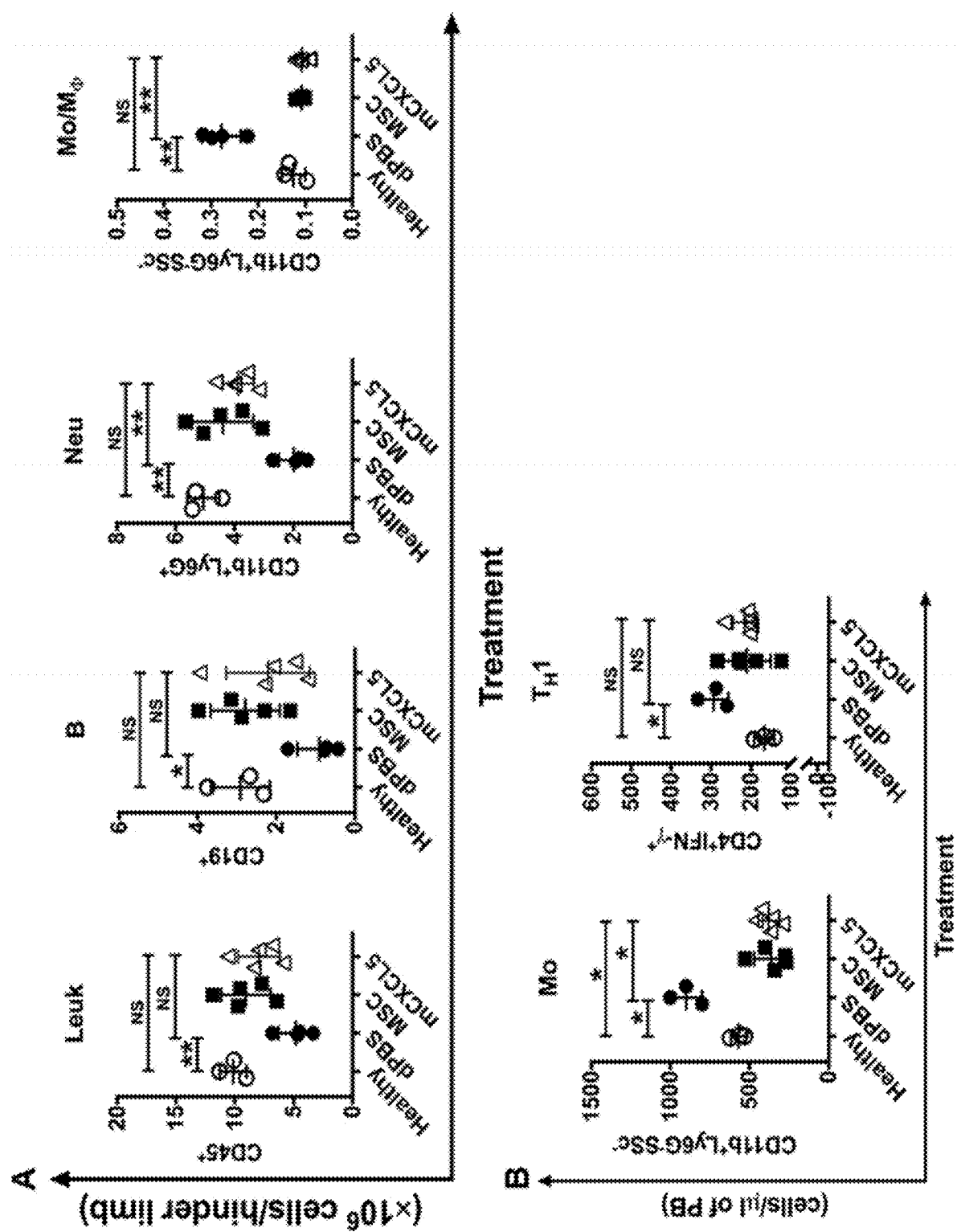
FIG. 23 shows results indicating that CXCL5 suppresses the proliferation of monocyte and $T_H1$ cells in systemic sclerosis (SSc). Effector cell number changes are shown in box plots for (A) Bone marrow (BM) and (B) peripheral blood (PB), respectively. Leu—leukocytes; B—B cells; Neu—neutrophils; monocytes—Mo; macrophages—$M_\Phi$. For multiple t-test comparison: *-$p<0.0167$; -$p<0.0033$; *-$p<0.00033$ when n=3.
Figure 24:
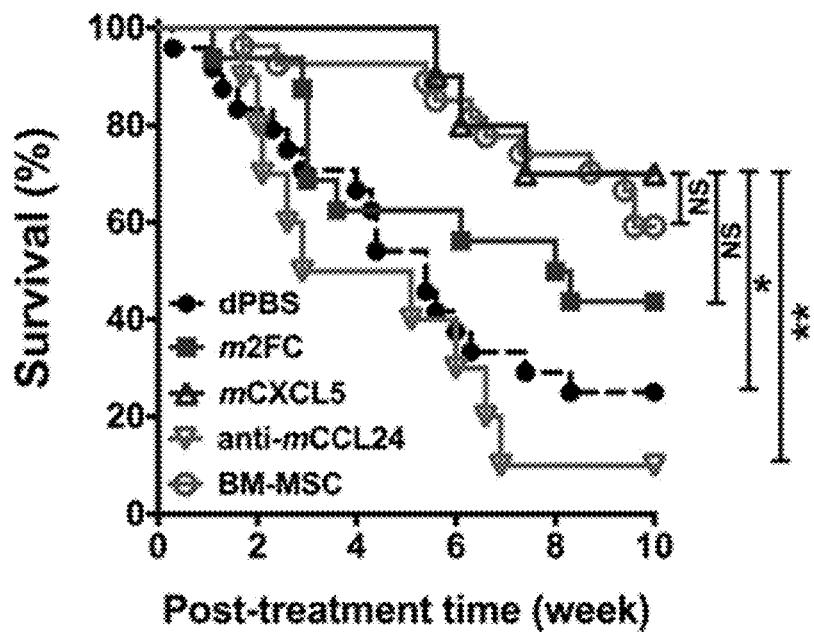
FIG. 24 shows data indicating that CXCL5 suppresses the proliferation of neutrophils, $T_H17$ cells and monocytes/macrophages in mouse systemic lupus erythematosus (SLE). (A) shows survival curves of $Fas^{lpr}$ mice (10 to 27 mice per group). (B) shows box plots illustrating effector cell changes in the spleen. Neu—neutrophils; monocytes—Mo; macrophages—$M_\Phi$. Results were expressed as mean±SD. For multiple t-test comparison: *-$p<0.025$; -$p<0.005$; *-$p<0.0005$ when n=2.
Figure 24:
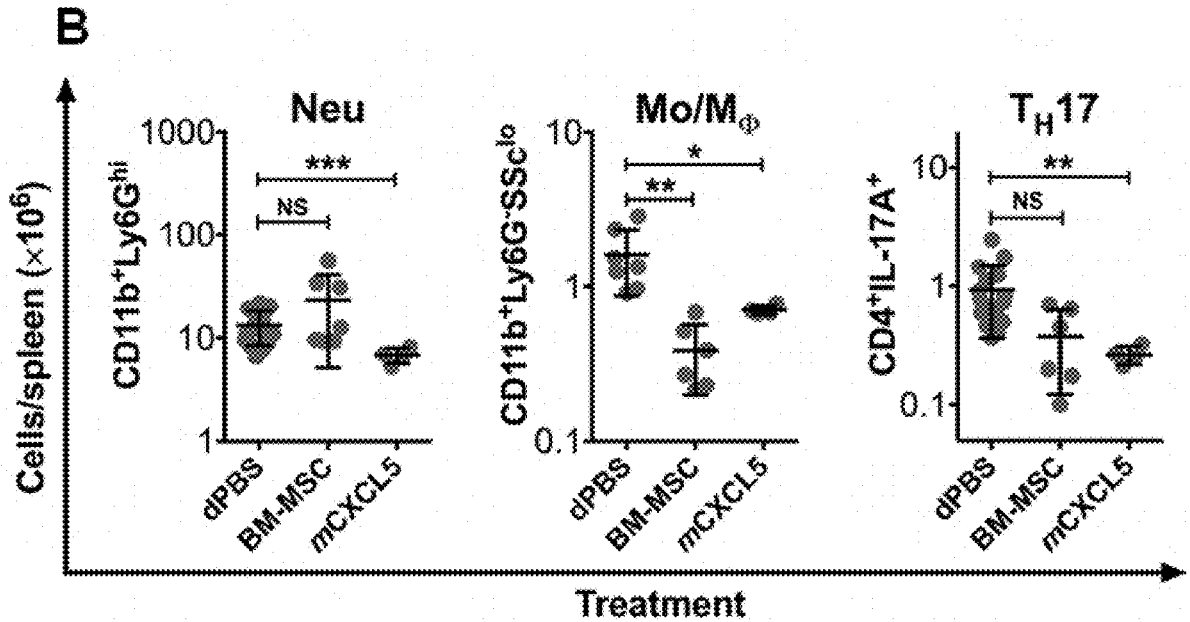

23B). The treatment was also thought to maintain the normal hematopoiesis in bone marrow (BM) after CXCL5 treatment as the number of leukocytes, B cells, neutrophils and monocytes/macrophages are equivalent to healthy control (FIG. 23A). At the same time, the leukocyte infiltration in the skin was also reduced from 6.5±1.9 cells/HPF (dPBS) to 2.3±2.0 cells/HPF (CXCL5) (FIG. 22B). Although mesenchymal stem cell therapy was also shown to reduce the skin leukocyte infiltration (2.9±1.3 cells/HPF, MSC), two out of nine mice did not respond to mesenchymal stem cell treatment.

mCXCL5 Attenuates Systemic Lupus Erythematosus (SLE) by Suppressing Neutrophils, $T_H17$ and monocytes/macrophages It had been previously demonstrated that there is immunosuppressive potential in a pre-clinical model of systemic lupus erythematosus (SLE) using a human source of CXCL5 and anti-CCL24. Upon switching to murine source of reagents, it was also shown that mCXCL5 (murine CXCL5) alone was effective in suppressing symptoms and prolonging survival in up to 70% of the mice tested. (7/10 mice), showing improved results compared to treatment with anti-mCCL24 alone (an antibody against murine CCL24; 10%, 1/10 mice) and equivalent to mesenchymal stem cell therapy (59.3%, 16/27 mice) (FIG. 24A). Mechanism studies have revealed that mCXCL5 mimics the effects of mesenchymal stem cells to attenuate systemic lupus erythematosus by suppressing the proliferation of $T_H17$, and monocytes/macrophages (FIG. 24B). Beyond that, mCXCL5 was also shown to reduce the proliferation of neutrophils in spleen (FIG. 24B).

Tables

TABLE 2

List of regulated proteins

| Cytokine | Relative expression (fold change) $\frac{MLR \text{ on } MSC}{MLR + MSC - CM}$ |
|---|---|
| MIP-3-alpha (CCL20) | 29.79 ± 34.05 |
| MCP-3 (CCL8) | 4.93 ± 5.22 |
| ENA-78 (CXCL5) | 4.77 ± 1.90 |
| OPG | 4.21 ± 1.21 |
| GCP-2 (CXCL6) | 3.52 ± 5.53 |
| IL-1beta | 0.33 ± 0.23 |
| I-309 (CCL1) | 0.31 ± 0.25 |
| Eotaxin-2 (CCL24) | 0.17 ± 0.09 |

Results were expressed as mean ± S.E., n = 3

TABLE 3

Experimental condition in $2^{12}$ fractional FD

| Factor Condition | PGE2 | CCL20 | CXCL6 | CCL8 | CCL7 | OPG | IL-10 | CXCL5 | anti-CCL1 | anti-IL1b | anti-M-CSF | anti-CCL24 |
|---|---|---|---|---|---|---|---|---|---|---|---|---|
| C1 (MLR) | 1 | 1 | 1 | 1 | 1 | 1 | 1 | 1 | 1 | 1 | 1 | 1 |
| C2 | 1 | 1 | 1 | 1 | 1 | 1 | 1 | 2 (50 ng/ml) | 2 (2 µg/ml) | 2 (1 µg/ml) | 2 (1 µg/ml) | 2 (2 µg/ml) |
| C3 | 1 | 1 | 1 | 2 (10 ng/ml) | 2 (50 ng/ml) | 2 (10 ng/ml) | 2 (10 ng/ml) | 1 | 1 | 1 | 1 | 2 (2 µg/ml) |
| C4 | 1 | 1 | 1 | 2 (10 ng/ml) | 2 (50 ng/ml) | 2 (10 ng/ml) | 2 (10 ng/ml) | 2 (50 ng/ml) | 2 (2 µg/ml) | 2 (1 µg/ml) | 2 (1 µg/ml) | 1 |
| C5 | 1 | 2 (50 ng/ml) | 2 (10 ng/ml) | 1 | 1 | 2 (10 ng/ml) | 2 (10 ng/ml) | 1 | 1 | 2 (1 µg/ml) | 2 (1 µg/ml) | 1 |
| C6 | 1 | 2 (50 ng/ml) | 2 (10 ng/ml) | 1 | 1 | 2 (10 ng/ml) | 2 (10 ng/ml) | 2 (50 ng/ml) | 2 (2 µg/ml) | 1 | 1 | 2 (2 µg/ml)) |
| C7 | 1 | 2 (50 ng/ml) | 2 (10 ng/ml) | 2 (10 ng/ml) | 2 (50 ng/ml) | 1 | 1 | 1 | 1 | 2 (1 µg/ml) | 2 (1 µg/ml) | 2 (2 µg/ml) |
| C8 | 1 | 2 (50 ng/ml) | 2 (10 ng/ml) | 2 (10 ng/ml) | 2 (50 ng/ml) | 1 | 1 | 2 (50 ng/ml) | 2 (2 ng/ml) | 1 | 1 | 1 |
| C9 | 2 (2 µM) | 1 | 2 (10 ng/ml) | 1 | 2 (50 ng/ml) | 1 | 2 (10 ng/ml) | 1 | 2 (2 µg/ml) | 1 | 2 (1 µg/ml) | 1 |
| C10 | 2 (2 µM) | 1 | 2 (10 ng/ml) | 1 | 2 (50 ng/ml) | 1 | 2 (10 ng/ml) | 2 (50 ng/ml) | 1 | 2 (1 µg/ml) | 1 | 2 (2 µg/ml) |
| C11 | 2 (2 µM) | 1 | 2 (10 ng/ml) | 2 (10 ng/ml) | 1 | 2 (10 ng/ml) | 1 | 1 | 2 (2 µg/ml) | 1 | 2 (1 µg/ml) | 2 (2 µg/ml) |
| C12 | 2 (2 µM) | 1 | 2 (10 ng/ml) | 2 (10 ng/ml) | 1 | 2 (10 ng/ml) | 1 | 2 (50 ng/ml) | 1 | 2 (1 µg/ml) | 1 | 1 |
| C13 | 2 (2 µM) | 2 (50 ng/ml) | 1 | 1 | 2 (50 ng/ml) | 2 (10 ng/ml) | 1 | 1 | 2 (2 µg/ml) | 2 (1 µg/ml) | 1 | 1 |
| C14 | 2 (2 µM) | 2 (50 ng/ml) | 1 | 1 | 2 (50 ng/ml) | 2 (10 ng/ml) | 1 | 2 (50 ng/ml) | 1 | 1 | 2 (1 µg/ml) | 2 (2 µg/ml) |
| C15 | 2 (2 µM) | 2 (50 ng/ml) | 1 | 2 (10 ng/ml) | 1 | 1 | 2 (10 ng/ml) | 1 | 2 (2 µg/ml) | 2 (1 µg/ml) | 1 | 2 (2 µg/ml) |
| C16 | 2 (2 µM) | 2 (50 ng/ml) | 1 | 2 (10 ng/ml) | 1 | 1 | 2 (10 ng/ml) | 2 (50 ng/ml) | 1 | 1 | 2 (1 µg/ml) | 1 |
| Full panel | 2 (2 µM) | 2 (50 ng/ml) | 2 (10 ng/ml) | 2 (10 ng/ml) | 2 (50 ng/ml) | 2 (10 ng/ml) | 2 (10 ng/ml) | 2 (50 ng/ml) | 2 (2 µg/m) | 2 (1 µg/ml) | 2 (1 ug/ml) | 2 (2 µg/ml) |
| MLR on MSC | 1 | 1 | 1 | 1 | 1 | 1 | 1 | 1 | 1 | 1 | 1 | 1 |

"1" indicates that the substance is not present;
"2" indicates that the substance is present.

TABLE 4

Experimental condition in $2^7$ fractional FD

| Factor Condition | anti-CCL24 | IL-10 | OPG | CXCL5 | CXCL6 | anti-CCL1 | CCL20 |
|---|---|---|---|---|---|---|---|
| C1 (MLR) | 1 | 1 | 1 | 1 | 1 | 1 | 1 |
| C17 | 1 | 1 | 1 | 2 (50 ng/ml) | 2 (10 ng/ml) | 2 (2 μg/ml) | 2 (50 ng/ml) |
| C18 | 1 | 2 (10 ng/ml) | 2 (10 ng/ml) | 1 | 1 | 2 (2 μg/ml) | 2 (50 ng/ml) |
| C19 | 1 | 2 (10 ng/ml) | 2 (10 ng/ml) | 2 (50 ng/ml) | 2 (10 ng/ml) | 1 | 1 |
| C20 | 2 (2 ug/ml) | 1 | 2 (10 ng/ml) | 1 | 2 (10 ng/ml) | 1 | 2 (50 ng/ml) |
| C21 | 2 (2 ug/ml) | 1 | 2 (10 ng/ml) | 2 (50 ng/ml) | 1 | 2 (2 μg/ml) | 1 |
| C22 | 2 (2 ug/ml) | 2 (10 ng/ml) | 1 | 1 | 2 (10 ng/ml) | 2 (2 μg/ml) | 1 |
| C23 | 2 (2 ug/ml) | 2 (10 ng/ml) | 1 | 2 (50 ng/ml) | 1 | 1 | 2 (50 ng/ml) |
| Full panel | 2 (2 ug/ml) | 2 (10 ng/ml) | 2 (10 ng/ml) | 2 (50 ng/ml) | 2 (10 ng/ml) | 2 (2 μg/ml) | 2 (50 ng/ml) |

"1" indicates that the substance is not present;
"2" indicates that the substance is present.

TABLE 5

Experimental condition in $2^4$ full FD

| Condition | anti-CCL1 | anti-CCL24 | OPG | CXCL5 |
|---|---|---|---|---|
| C1 (MLR) | 1 | 1 | 1 | 1 |
| C24 | 2 (2 ug/ml) | 1 | 1 | 1 |
| C25 | 1 | 2 (2 ug/ml) | 1 | 1 |
| C26 | 1 | 1 | 2 (10 ng/ml) | 1 |
| C27 | 1 | 1 | 1 | 2 (50 ng/ml) |
| C28 | 2 (2 ug/ml) | 2 (2 ug/ml) | 1 | 1 |
| C29 | 2 (2 ug/ml) | 1 | 2 (10 ng/ml) | 1 |
| C30 | 2 (2 ug/ml) | 1 | 1 | 2 (50 ng/ml) |
| C31 | 1 | 2 (2 ug/ml) | 2 (10 ng/ml) | 1 |
| C32 | 1 | 2 (2 ug/ml) | 1 | 2 (50 ng/ml) |
| C33 | 1 | 1 | 2 (10 ng/ml) | 2 (50 ng/ml) |
| C34 | 2 (2 ug/ml) | 2 (2 ug/ml) | 2 (10 ng/ml) | 1 |
| C35 | 2 (2 ug/ml) | 2 (2 ug/ml) | 1 | 2 (50 ng/ml) |
| C36 | 2 (2 ug/ml) | 1 | 2 (10 ng/ml) | 2 (50 ng/ml) |
| C37 | 1 | 2 (2 ug/ml) | 2 (10 ng/ml) | 2 (50 ng/ml) |
| C38-Full panel | 2 (2 ug/ml) | 2 (2 ug/ml) | 2 (10 ng/ml) | 2 (50 ng/ml) |

"1" indicates that the substance is not present;
"2" indicates that the substance is present.

TABLE 6

Dosage for MTD study

| Soluble factor | Week-1 | Week-2 | Week-3 | Week-4 |
|---|---|---|---|---|
| dPBS | 100 μl/mouse | 100 μl/mouse | 100 μl/mouse | 100 μl/mouse |
| anti-CCL24 | 1 μg/ml | 2 μg/ml | 6 μg/ml | |
| CXCL5 | 10 ng/ml | 50 ng/ml | 100 ng/ml | 200 ng/ml |

TABLE 7

Histological score in NSG mice

| | dPBS | 2FC | MSC | CsA | CXCL5 | Anti-CCL24 |
|---|---|---|---|---|---|---|
| Skin | | | | | | |
| Vacuolar change | mild | none | none | none | none | none |
| spongiosis | mild | none | none | none | none | none |
| Lymphocytic satelitosis number of cells | >10 (severe) | <5 (mild) | >5 (mod) | >5 (mod) | <5 (mild) | <5 (mild) |

TABLE 7-continued

Histological score in NSG mice

|  | dPBS | 2FC | MSC | CsA | CXCL5 | Anti-CCL24 |
|---|---|---|---|---|---|---|
| Small intestine | | | | | | |
| Apoptosis | mild to entire crypt loss (moderate) | 2/hpf (mild) | 4/hpf (mild) | 2/hpf(mild) | 1/hpf (mild) | 1/hpf(mild) |
| Lymphocytic inflammation | nil | mild | mild | mild | mild | mild to none |
| Intraepithelial lymphocytosis | nil | 2/50 epithelial cells (mild) | 4/50 epithelial cells(mod) | 3/50 epithelial cells (mod) | 2/50 epithelial cells(mild) | 1/50 epithelial cells (mild) |
| Kidney | | | | | | |
| Interstitial inflammation | severe | mild | mod | mild | mild | mod |
| Tubulitis | mod | mild | mod | mild | mild | mod |
| Arterial changes | mild (1 vessel) | none | none | none | none | none |
| Σscore | 13 | 6 | 10 | 8 | 6 | 8 |

Overall score and severity: Mild, 0-9; moderate, 10-18; Severe, 19-27.
Mod: moderate;
hpf: high power field.

The invention claimed is:

1. A method of treating diffuse alveolar haemorrhage, systemic lupus erythematosus (SLE), systemic sclerosis, scleroderma, systemic vasculitis, vasculitis and/or rheumatoid arthritis, the method comprising administration to a subject a pharmaceutical composition consisting of CXCL5 (ENA-78) and one or more pharmaceutically acceptable excipients.

2. The method of claim 1, wherein the pharmaceutical composition results in a decrease in a concentration of one or more of circulating pro-inflammatory cytokines selected from the group consisting of IFN-γ, IL-6, IL-17A, IL-8, MIP-1β, and MCP-1 in the subject.

3. The method of claim 1, wherein the pharmaceutical composition results in an increase or a decrease in a concentration of at least one mesenchymal stromal cell-derived protein in the subject, which results in an immunosuppressive effect, wherein the mesenchymal stromal cell-derived protein is selected from the group consisting of PGE2 (prostaglandin E2), OPG, CCL7, CCL8, IL-10, CCL20, CXCL5, CXCL6, M-CSF, IL-1β, CCL-1, and CCL24.

4. A method of modulating the immune system, the method comprising administration of a pharmaceutical composition to a subject, wherein the pharmaceutical composition consists of CXCL5 (ENA-78) and one or more pharmaceutically acceptable excipients.

5. The method of claim 4, wherein the pharmaceutical composition results in a decrease in a concentration of one or more of circulating pro-inflammatory cytokines selected from the group consisting of IFN-γ, IL-6, IL-17A, IL-8, MIP-1β, and MCP-1 in the subject.

6. The method of claim 4, wherein the pharmaceutical composition results an increase or a decrease in a concentration of at least one mesenchymal stromal cell-derived protein in a subject, which results in an immunosuppressive effect, wherein the mesenchymal stromal cell-derived protein is selected from the group consisting of PGE2 (prostaglandin E2), OPG, CCL7, CCL8, IL-10, CCL20, CXCL5, CXCL6, M-CSF, IL-1β, CCL-1, and CCL24.

* * * * *

UNITED STATES PATENT AND TRADEMARK OFFICE
CERTIFICATE OF CORRECTION

PATENT NO. : 11,246,910 B2
APPLICATION NO. : 16/282461
DATED : February 15, 2022
INVENTOR(S) : Fan et al.

It is certified that error appears in the above-identified patent and that said Letters Patent is hereby corrected as shown below:

On the Title Page

Item (57), Line 1, "The present disclosure describes a method of treating immunological disorders, for example alloimmune and autoimmune diseases, using a pharmaceutical composition comprising at least one mesenchymal stromal cell-derived protein Further disclosed herein is the use of the pharmaceutical composition for immunomodulation." should be -- The present disclosure describes a pharmaceutical composition comprising at least one antibody and at least one mesenchymal stromal cell-derived protein. Disclosed herein is also the use of said pharmaceutical composition for treating immunological diseases, for example alloimmune and autoimmune diseases. Further disclosed herein is the use of the pharmaceutical composition for immunomodulation. --.

In the Claims

At Column 46, Line 34, "results an" should be -- results in an --.

Signed and Sealed this
Sixth Day of September, 2022

Katherine Kelly Vidal
*Director of the United States Patent and Trademark Office*